(12) United States Patent
Lenhert et al.

(10) Patent No.: US 9,995,732 B2
(45) Date of Patent: *Jun. 12, 2018

(54) EVAPORATIVE EDGE LITHOGRAPHY OF A LIPOSOMAL DRUG MICROARRAY FOR CELL MIGRATION ASSAYS

(71) Applicant: FLORIDA STATE UNIVERSITY RESEARCH FOUNDATION, Tallahassee, FL (US)

(72) Inventors: Steven Lenhert, Tallahassee, FL (US); Nicholas Vafai, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 496 days.

This patent is subject to a terminal disclaimer.

(21) Appl. No.: 14/178,325

(22) Filed: Feb. 12, 2014

(65) Prior Publication Data

US 2014/0162905 A1 Jun. 12, 2014

Related U.S. Application Data

(63) Continuation-in-part of application No. PCT/IB2013/055762, filed on Jul. 12, 2013.

(60) Provisional application No. 61/841,980, filed on Jul. 2, 2013, provisional application No. 61/671,214, filed on Jul. 13, 2012.

(51) Int. Cl.
| | |
|---|---|
| *C40B 50/00* | (2006.01) |
| *C40B 50/08* | (2006.01) |
| *G01N 33/50* | (2006.01) |
| *G01N 33/543* | (2006.01) |
| *C40B 40/00* | (2006.01) |

(52) U.S. Cl.
CPC ... *G01N 33/5029* (2013.01); *G01N 33/54366* (2013.01); *G01N 2405/00* (2013.01)

(58) Field of Classification Search
CPC .................................................... G01N 33/50
USPC ............................................................ 506/14
See application file for complete search history.

(56) References Cited

U.S. PATENT DOCUMENTS

| | | | |
|---|---|---|---|
| 6,548,263 B1 | 4/2003 | Kapur et al. | |
| 7,531,366 B2 | 5/2009 | Abbott et al. | |
| 8,642,516 B2* | 2/2014 | Koepsel ............... | G01N 33/553 506/13 |
| 2007/0004046 A1 | 1/2007 | Abbott et al. | |
| 2007/0059765 A1 | 3/2007 | Wang et al. | |

(Continued)

FOREIGN PATENT DOCUMENTS

| | | |
|---|---|---|
| WO | 2005015792 A2 | 2/2005 |
| WO | 2006078952 A1 | 7/2006 |

(Continued)

OTHER PUBLICATIONS

Nafday et al., Multifunctional Lipid Multilayer Stamping, Small, 2012, 8(7), 1021-1028.*

(Continued)

*Primary Examiner* — Amy M Bunker
(74) *Attorney, Agent, or Firm* — Fox Rothschild LLP

(57) ABSTRACT

Lipid multilayer structures are formed by evaporating a solvent from each of a plurality of lipid solutions thereby form the lipid multilayer structures. Each lipid solution comprises the solvent and one or more lipids. Each lipid multilayer structure is a microstructure comprising one or more lipids.

8 Claims, 42 Drawing Sheets

(56) References Cited

U.S. PATENT DOCUMENTS

| | | | |
|---|---|---|---|
| 2007/0178534 | A1 | 8/2007 | Murphy et al. |
| 2009/0181172 | A1 | 7/2009 | Parpia et al. |
| 2010/0009344 | A1 | 1/2010 | Israel et al. |
| 2010/0221815 | A1 | 9/2010 | Abbott et al. |
| 2012/0070885 | A1 | 3/2012 | Lenhert |
| 2012/0075441 | A1 | 3/2012 | Lenhert |
| 2012/0098974 | A1 | 4/2012 | Lenhert et al. |
| 2012/0231489 | A1 | 9/2012 | Lenhert |
| 2012/0258292 | A1 | 10/2012 | Lenhert et al. |
| 2013/0137599 | A1 | 5/2013 | Lenhert et al. |
| 2014/0051602 | A1 | 2/2014 | Lenhert |

FOREIGN PATENT DOCUMENTS

| | | | | |
|---|---|---|---|---|
| WO | WO 2011017487 | A2 * | 2/2011 | ............ B41M 3/006 |
| WO | 2014013456 | A2 | 1/2014 | |

OTHER PUBLICATIONS

Marty et al., Structural Analysis of DNA Complexation With Cationic Lipids, Nucleic Acids Research, 2009, 37(3), 849-857.*

Lenhert et al., Lipid Multilayer Gratings, Nature Nanotechnology Letters, 2010, 5, 275-279.*

Sanjana et al., A Fast Flexible Ink-Jet Printing Method for Patterning Dissociated Neurons in Culture, Journal of Neuroscience Methods, 2004, 136, 151-163.*

Yamazaki et al., Cell Membrane Array Fabrication and Assay Technology, BMC Biotechnology, 2005, 5(18), 1-11. (Year: 2005).*

Diguet et al., Preparation of Phospholipid Multilayer Patterns of Controlled Size and Thickness by Capillary Assembly on a Microstructures Substrate, Small, 2009, 5(14), 1661-1666. (Year: 2009).*

Harris, D.J., et al., "Marangoni Effects on Evaporative Lithographic Patterning of Colloidal Films," vol. 15, Issue 24(8), 4 pages, Langmuir 2008.

International Search Report and Written Opinion dated Oct. 27, 2014 in corresponding International Application No. PCT/IB2014/062802.

International Preliminary Report on Patentability received in PCT Application No. PCT/IB2013/055762 dated Jan. 22, 2015.

Lenhert, S., Meier, M. B., Meyer, U., Chi, L. F. and Wiesmann, H. P., "Osteoblast alignment, elongation and migration on grooved polystyrene surfaces patterned by Langmuir-Blogdett lithography," Biomaterials, 26, 563-570 (2005).

Shin, K. D., Lee, M. Y., Shin, D. S., Lee, S., Son, K. H., Koh, S. Paik, Y. K., Kwon B. M. and Han, D. C., "Blocking tumor cell migration and invasion with biphenyl isoxazole derivative KRIBB3, a synthetic molecule that inhibits Hsp27 phosphorylation," Journal of Biological Chemistry., 280, 41439-41448 (2005).

Gough, W., Hulkower, K. I., Lynch, R., McGlynn, P., Uhlik, M., Yan, L. and Lee, J. A, "A quantitative, facile, and high-throughput image-based cell migration method is a robust alternative to the scratch assay," Journal of Biomolecular Screening, 16, 155-163 (2011).

Attoub, S., Hassan, A. H., Vanhoecke, B., Iratni, R., Takahashi, T. Gaben, A.-M., Bracke, M., Awad, S., John, A., Kamalboor, H. A., Al Sultan, M. A., Al Sultan, M. A. Arafat, K. Gespach, C. and Petroianu, G., "Inhibition of cell survival, invasion, tumor growth and histone desctylase activity by the dietary flavonoid luteolin in human epitholioid cancer cells," European Journal of Pharmacology, 651, 18-25 (2011).

Chung, S., Sudo, R., Mack, P. J., Wan, C. R., Vickerman, V. and Kamm, R. D., "Cell migration into scaffolds under co-culture conditions in a microfluidic platform," Lab on a Chip, 9, 269-275 (2009).

Conant, C. G., Nevill, J. T., Schwartz, M. and Ionescu-Zanetti, C., "Wound healing assays in well-plate coupled microfluidic devices with controlled parallel flow," Journal of the Association for Laboratory Automation, 15, 52-57 (2010).

Huang, X. W., Li, L., Tu, Q., Wang, J. C., Liu, W. M., Wang, X. Q., Ren, L. and Wang, J. Y., "On-chip cell migration assay for quantifying the effect of ethanol on MCF7 human breast cancer cells," Microfluid Nanofluid, 10, 1333-1341 (2011).

Poujade, M., Grasland-Mongrain, E., Hertzog, A , Jouanneau, J., Chavrier, P., Ladoux, B., Buguin, A. and Silberzan, P. "Collective migration of an epithelial monolayer in response to a model wound," Proceedings of the National Academy of Sciences of the United States of America, 104, 15988-15993 (2007).

Wang, L, Zhu, J., Deng, C., Xing, W. L. and Cheng, J., "An automatic and quantitative on-chip cell migration assay using self-assembled monolayers combined with real-time cellular impedance sensing," Lab on a Chip, 8, 872-878 (2008).

Kim, B. J. and Wu, M. M., "Microfluidics for mammalian cell chemotaxis," Annals of Biomedical Engineering, 40, 1316-1327 (2012).

Liu, T. J. Lin, B C. and Qin, J. H., "Carcinoma-associated fibroblasts promoted tumor spheroid invasion on a microfluidic 3D co-culture device," Lab on a Chip, 10, 1671-1677 (2010).

Wang, Z., Kim, M.-C., Marquez, M. and Thorsen, T., "High-density microfludic arrays for cell cytotoxicvity analysis," Lab on a Chip, 7, 740-745 (2007).

Kwak, Y. H., Hong, S. M. and Park, S. S., "A single cell tracking system in real-time," Cellular Immunology, 265, 44-49 (2010).

Puliafito, A., Hufnagel, L., Neveu, P., Streichan, S., Sigal, A., Fygenson, D. K. and Shraiman, B. I. "Collective and single cell behavior in epithelial contact inhibition," Proceedings of the National Academy Sciences of the United States of America, 109, 739-744 (2012).

Adanja I., Megalizzi, V., Debeir, O., and Decaestecker, C. "A new method to address unmet needs for extracting individual cell migration features from a large number of cells embedded in 3D volumes," PLoS One, 6 (2011).

Diaz-Mochon, J. J., Tourniaire, and Bradley, M., "Microarray platforms for enzymatic and cell-based assays," Chemical Society Reviews, 36, 449-457 (2007).

Yarrow, J. C., Totsukawa, G., Charras, G. T. and Mitchison, T. J. "Screening for cell migration inhibitors via automated microscopy reveals a Rho-kinase inhibitor," Chemistry & Biology, 12, 385-395 (2005).

Szoka F., and Papahadjopoulos, D., "Comparative Properties and Methods of Preparation of Lipid Vesicles (Liposomes)," Annu. Rev. Biophys. Bio 9, 467-508 (1980).

Tourniaire, G. , Collins, J., Campbell, S., Mizomoto, H. Ogawa, S., Thaburet, J. F. and Bradley, M. "Polymer microarrays for cellular adhesion," Chemical Communications, 2118-2120 (2006).

Balakin, K V., Savchuk, N. P. and Tetko, I. V., "In silico approaches of aqueous and DMSO solubility of drug-like compounds: trends, problems and solutions," Current Medicinal Chemistry, 13, 223-241 (2006).

Moran-Mirabal, et al., "Micrometer-sized supported lipid bilayer arrays for bacterial toxin binding studies through total Internal reflection fluorescence microscopy," Biophys. J. 89, 296-305 (2005).

Deng, Y. et al., "Fluidic and air-stavle supported lipid bilayer and cell-mimicking microarrays," J. Am. Chem. Soc. 130, 6267-71 (2008).

Heller, M.J., "DNA microarray technology: devices, systems, and applications," Annu. Rev. Biomed, Eng. 4 129-53 (2002).

Majd, S. and Mayer, M., "Generating arrays with high content and minimal consumption of functional membrane proteins," Journal of American Chemical Society, 130, 16060-16064 (2008).

Diguet, A. Le Berre, M. Chen, Y. and Baigl, D., "Preparation of phospholipid multilayer patterns of controlled size and thickness by capillary assumbly on a microstructured substrate," Small, 5, 1661-1666 (2009).

Brinker, C. J., Lu, Y. F., Sellinger, A. and Fan, H. Y., "Evaporation-induced self-assembly: Nanostructures made easy," Advanced Materials, 11, 579-+(1999).

Yuan, B., Xing, L. L., Zhang, Y. D., Lu, Y., Mai, Z. H. and Li, M., "Self-assembly of highly oriented lamellar nanoparticle-phospholipid nanocomposites on solid surfaces," Journal of American Chemical Society, 129, 11332-+(2007).

(56) References Cited

OTHER PUBLICATIONS

Groves, J. T., Mahal, L K and Bertozzi, C. R. Langmuir, "Control of cell adhesion and growth with micropatterned supported lipid membranes," 17, 5129-5133 (2001).
Tang, F. and Hughes, J. A., "Synthesis of a single-tailed cationic lipid and investigation of its transfection," Journal of Controlled Release, 62, 345-358 (1999).
Fayad, W., Rickardson, L., Haglund, C., Olofsson, M. Fl, D'Arcy, P., Larsson, R., Linder, S. and Fryknas, M., "Identification of agents that induce apoptosis oif multicellular tumour spheroids: enrichment for mitotic inhibitors with hydrophobic properties," Chemical Biology and Drug Design, 78, 547-557 (2011).
J.-W. Zhu, H. Nagasawa, F. Nagura, S. B. Mohamad, Y. Uto, K. Ohkura and H. Hon, "Elucidation of Strict Structural Requirements of Brefeldin A as an Inducer of Differentiations and Apoptosis," Bioorg. Med. Chem., 8, 455-463 (2000).
"Evaporative Edge Lithography (EEL) of a Liposomal Drug Microarray for Cell Migration Assays," U.S. Appl. No. 61/841,980, filed Jul. 2, 2013.
"Scalable Liposome Microarray Screening," Application No. PCT/IB2013/05572, filed Jul. 12, 2013.
"Surface Supported Liposome Nanoarrays as Biomimetic Sensors," Application No. PCT/IB2013/055884, filed Jul. 17, 2013.
Barbulovic-Nad et al., "Bio-Microarray Fabrication Techniques—a Review, Critical Reviews in Biotechnology", vol. 26, No. 4, pp. 237-259, 2006.
Renault, et al., "Fabricating Microarrays of Functional Proteins Using Affinity Contact Printing", Angewandte Chemie., vol. 114, Issue 13, pp. 2426-2429, 2002.
van Horssen, R. and ten Hagen, T. L M., "Crossing barriers: The new dimension of 2D cell migration assays," Journal of Celular Physiology., 226, 288-290 (2011).
Howbrook, D. N., van der Valk, A. M., O'Shaughnessy, M. C., Sarker, D. K., Baker, S. C., and Lloyd, A. W., "Developments in microarray technologies," Drug Discov. Today 15, 648-51 (2003).
Eteshola, E., and Leckband, D., "Development and characterization of an ELISA assay in PDMS microfluidic channels," Sens. Actuator B—Chem. 72, 129-33 (2001).
Piner, R. D., Zhu, J., Xu, F., Hong, S. H., and Mirkin, C. A., "Dip-pen" nanolithography, Science 283, 661-63 (1999).
Salaita, K, Wang, Y. H., Fragala, J., Vega, R. k, Liu, C., Mirkin, C. A. "Massively parallel dip-pen nanolithography with 55000-pen two-dimensional arrays," Angew. Chem. Int. Ed. 45, 7220-23 (2006).
Kusi-Appiah, A., Vafai, N., Cranfill, P. J., Davidson, M. W. & Lenhert, S., "Lipid multilayer microarrays for in vitro liposomal drug delivery and screening," Biomaterials 33(16) 4187-94 (2012).
Jang, J. W., Smetana, A., and Stiles, P., "Multi-ink pattern generation by dip-pen nanolithography," Scanning 32, 24-29 (2010).
Torchilin, V. P., "Recent advances with liposomes as pharmaceutical carriers," Nat. Rev. Drug Discov. 4, 145-60 (2005).
Szymanski, P., Markowicz, M. and Mikiciuk-Olasik, E. "Adaptation of High-Throughput Screening in Drug Discovery—Toxicological Screening Tests," International Journal of Molecular Sciences 13, 427-452 (2012.
Sampieri, K. and Fodde, R., "Cancer stem cells and metastasis," Seminars in Cancer Biology., 22, 187-193 (2012).
Brabletz, T., Jung, A., Spaderna, S., Hlubek F., and Kirchner, T., "Opinion: migrating cancer stem cells—an integrated concept of malignant tumour progression." Nature Reviews Cancer, 5, 744-749 (2005).
Eilken, H. M. and Adams, R. H., "Dynamics of endothelial cell behavior in sprouting angiogenesis," Current Opinion in Cell Biology, 22, 617-625 (2010).
Grifficen, A. W. and Molema, G., "Anti-angiogenesis: making the tumor vulnerable to the immune system," Pharmacoogy Review., 52, 237-268 (2000).
Aman, A. and Piotrowski, T. "Cell migration during morphogenesis," Developmental Biology, 341, 20-33 (2010).

Weijer, C. J. "Collective cell migration in development," Journal of Cell Science., 122, 3215-3223 (2009).
Liang, C. C., Park, A. Y. and Guan, J. L., "In vitro scratch assay: a convenient and inexpensive method for analysis of cell imgration invitro," Nature Protocols., 2, 329-333 (2007).
Valster, A., Tran, N. L., Nakada, M., Berens, M E., Chan A. Y. and Symons, M., "Cell migration and invasion assays," Methods, 37, 208-215 (2005).
Barenholz, Y., Gibbes, D., Litman, B. J., Goll, J., Thompson, T. E., and Carlson, F. D., "A simple method for the preparation of homogeneous phospholipid vesicles," Biochemistry 16, 2806-10 (1977).
Gustafsson, J., Arvidson, G., Karlsson, G., and Almgren, M. "Complexes between cationic liposomes and DNA visualized by Cryo-Tem," BBA-Biomembranes 1235, 305-12 (1995).
Kwon, C. H., Wheeldon, I., Kachouie, N. N., Lee, S. H., Bae, H., Sant, S., Fukuda, J., Kang, J. W., Khademhosseini, "Drug-eluting microarrays for cell-based screening of chemical-induced apoptosis," Anal. Chem. 83, 4118-25 (2011).
Malam, Y., Loizidou, M., and Seifalian, A. M., "Liposomes and nanoparticles: nanosized vehicles for drug delivery in cancer," Trends Pharmacol. Sci. 30, 592-99 (2009).
Porter, C. J. H., Trevaskis, N. L., and Charman, W. N., "Lipids and lipid-based formulations:optimizing the oral delivery of lipophilic drugs," Nat. Rev. Drug Discov. 6, 231-48 (2007).
Torchilin, V. P., "Micellar nanocarriers: pharmaceutical perspectives," Pharm. Res. 24, 1-16 (2007).
Koren, E., and Torchilin, V. P., "Drug carriers for vascular drug delivery," IUBMB Life 63, 586-95 (2011).
Gregoriadis, G., "Engineering liposomes for drug delivery: progress and problems," Trends in Biotechnology 13, 527-37 (1995).
Kusi-Appiah, A. E., Vafai, N., Cranfill, P. J., Davidson, M. W., and Lenhert, S., "Lipid multilayer microarrays for in vitro lipomosomal drug delivery and screening," Biomaterials 33, 4187-94 (2012).
Majd, S, and Mayer, M., "Hydrogel stamping of arrays of supported lipid bilayers with various lipid compositions for the screening of drug-membrane and protein-membrane interactions," Angew. Chem. Int. Ed. 44, 6697-6700 (2005).
Yamazaki, V., Sirenko, O., Schafer, R. J., Nguyen, L., Gutsmann, T., Brade, L., and Groves, J. T., "Cell membrane array fabrication and assay technology," BMC Biotechnology 2005, doi:10.1186/1472-6750-5-18 (2005).
Lenhert, S., Brinkmann, F., Laue, T., Walheim, S., Vannahme, C., Klinkhammer, S., Xu, M., Sekula, S., Mappes, T., Schimmel, T., and Fuchs, H., "Lipid multilayer gratings," Nat. Nanotechnol. 5, 275-79 (2010).
Lenhert, S., Sun, P., Wang, Y. H., Fuchs, H., and Mirkin, C. A., "Massively parallel dip-pen nanolithography of heterogeneous supported phospholipid multilayer patterns," Small 3, 71-75 (2007).
Sekula, S., Fuchs, J., Weg-Remers, S., Nagel, P., Schuppler, S., Fragala, J., Theilacker, N., Franzreb, M., Wingren, C., Ellmark, P., Borrebaeck, C. A. K., Mirkin, C. A., Fuchs, H., and Lenhert, S., "Multiplexed lipid dip-pen nanolithography on subcellular scales for the templating of functional proteins and cell culture," Small 4, 1785-93 (2008).
Nafday, O. A., and Lenhert, S. "High-throughput optical quality control of lipid multilayers fabricated by dip-pen nanolithography," Nanotechnology 22, doi:225301 (2011).
Perino-Gallice, L., Fragneto, G., Mennicker, U., Salditt, T., and Rieutord, F., "Dewetting of solid-supported multilamellar lipid layers," Eur. Phys. J. E 8, 275-82 (2002).
Mathieu, M. Schunk, D., Franzka, S., Mayer, C., and Hartmann, N., "Temporal stability of photothermally fabricated micropatterns in supported phospholipid multilayers," J. Vac. Sci. Technol. A 28, 953-57 (2010).
Perl, A., Reinhoudt, D. N., and Huskens, J., "Microcontact printing: limitations and achievements," Adv. Mater. 21, 2257-68 (2009).
Nafday, O. A., Lowry, T. W., and Lenhert, S., "Multifunctional lipid multilayer stamping," Small 8, 1021-28 (2012).
Braunschweig, A. B., Huo, F. W., and Mirkin, C. A., "Molecular printing," Nat. Chem. 1, 353-58 (2009).
Salaita, K., Wang, Y. H., and Mirkin, C. A., "Applications of dip-pen nanolithography," Nat. Nanotechnol. 2, 145-55 (2007).

(56) References Cited

OTHER PUBLICATIONS

Ginger, D. S., Zhang, H., and Mirkin, C. A., "The evolution of dip-pen nanolithography," Angew. Chem. Int. Ed. 43, 30-45 (2004).
Zhang, M., Bullen, D., Chung, S. W., Hong, S., Ryu, K. S., Fanm Z. F., and Mirkin, C. A., and Liu, C., "A MEMS nanoplotter with high density parallel dip-pen nanolithography probe arrays," Nanotechnology 13, 212-17 (2002).
Xia, Y. N., and Whitesides, G. M., "Soft lithography," Annu. Rev. Mater. Sci. 28, 153-84 (1998).
Huo, F., Zheng, Z, Zheng, G, Giam, L., Zhang, H., and Mirkin, C. A., "Polymer pen lithography," Science 321 1658-60 (2008).
Chou, S. Y., Krauss, P. R., and Renstrom, P. J., "Imprint lithography with 25-nanometer resolution," Science 272, 85-87 (1996).
Lenhert, S., Mirkin C. A., and Fuchs, H., "In situ lipid dip-pen nanolithography under water," Scanning 32, 15-23 (2010).
Mendez-Vilas, A., Jodar-Reyes, A. B., and Gonzalez-Martin, M. L., "Ultrasmall liquid droplets on solid surfaces: production, imaging, and relevance for current wetting research," Small 5, 1366-90 (2009).
Witte, M. B. and Barbul, A., "General principles of wound healing," The Surgical Clinics of North America., 77, 509-+(1997).
Barbulovic-Nad, et al., "Bio-microarray fabrication techniques—a review", Critical Reviews in Biotechnology, vol. 26. No. 4, pp. 237-259, (2006).
Renalt, et al., "Fabricating Microarrays of Functional Protein Using Affinity Contact Printing," Angewandte Chemie, vol. 114, Issue 13, pp. 2426-2429, (2002).
Bailey, S. N., Sabatini D. M. and Stockwell, B. R., "Microarrays of small molecules embedded in biodegradable polymers for use in mammalian cell-based screens," Proceedings of the National Academy Sciences of the United States of America, 101, 16144-16149 (2004).
Jacob, S. W. and Herschler, R. "Pharmacology of DMSO," Cryobiology, 23, 14-27 (1986).
Grein, T. A., Freimark, D., Weber, C., Hudel, K., Wallrapp, C. and Czermak, P., "Alternatives to dimethylsulfoxide for serum-free cryopreservation of human mesenchymal stem cells," International Journal of Artificial Organs, 2010, 33, 370-380.
International Search Report & Written Opinion dated Mar. 5, 2014 in corresponding PCT/IB2013/055762.
Anderson, et al., "A Role for Lipid Shells in Targeting Proteins to Vaveolae, Rafts, and Other Lipid Domains," Science, vol. 296, Jun. 7, 2002, pp. 1821-1825.
Ausserre, D., et al., "Surface Enhanced Ellipsometric Contrast (SEEC) Basic Theory andA/4 Multilayered Solutions," Optics Excpress, vol. 15, No. 13, Jun. 25, 2007, pp. 8329-8339.
Benahmed, A., et al., "Period and Height Control During the Microcontact Printing of Alkoxysilane for Optical Gratings," J. Micro/Nanolith, MEMS MOEMS 6(2), (Apr.-Jun. 2007) pp. 023007-1-023007-5.
Bietsch, A., et al., "Conformal Contact and Pattern Stability of Stamps Used for Soft Lithography," Journal of Applied Physics, vol. 88, No. 7, Oct. 1, 2000, pp. 4310-4318.
Dennis, E.A., et al., "Role of Phospholipases in Generating Lipid Second Messengers in Signal Transduction," FASEB Journal, vol. 5, Apr. 1991, pp. 2068,2077.
Devries, J.J., "Nuclear Magnetic Resonance Measurements on a Macroscopially Ordered Smectic Liquid Crystalline Phase," Nature Publishing Group, vol. 221, Mar. 22, 1969, pp. 1139-1140.
Eggeling, C., et al., "Direct Observation of the Nanoscale Dynamics of Membrane Lipids in a Living Cell," Nature, vol. 457, No. 26, Feb. 2009, pp. 1159-1163.
Guo, L.J., et al., "Nanoimprint Lithography: Methods and Material Requirements," Advanced Materials, vol. 19, 2007, pp. 495-513.
Gupta, K., et al., "Lab-on-a-Chip Devices as an Emerging Platform for Stem Cell Biology," Lab Chip, vol. 10, 2010, pp. 2019-2031.
Haaheim, J., et al., "Dip Pen Nanolithography: A 'Desktop Nanofab' Approach Using High-Throughout Flexible Nanopatterning," Scanning vol. 30, 2008, pp. 137-150.
Hamadi, F., et al., "Effect on pH on Surface Energy of Glass and Teflon and Theoretical Prediction of *Staphylococcus aureus* Adhesion," Materials Science and Engineering, 2009, pp. 1302-1305.
Hovis, J.S., et al., "Patterning and Composiiton Arrays of Supported Lipid Bilayers by Microcontact Printing," Langmuir, vol. 17, 2001, pp. 3400-3405.
Izumi, J., et al., "Changes in Reflectin Protein Phosphorylation are Associated with Dynamic Iridescence in Squid," Journal of The Royal Scoeity, Interface, 2010, pp. 549-560.
Kane, R.S., et al., "Patterning Proteins and Cells Using Soft Lithography," Biomaterials, vol. 20, 1999, pp. 2363-2376.
Kidambi, S., et al., "Tunable Resistive m-dPEG Acid Patterns on Polyelectrolyte Multilayers at Physiological Conditions: Template for Directed Deposition of Biomacromolecules," Langmuir, vol. 24, 2008, pp. 224-230.
Kramer, R.M., et al., "The Self-Organizing Properties of Squid Reflectin Protein," Nature Materials, vol. 6, Jul. 2007, pp. 533-538.
Lalo H., et al., "Microscale Multiple Biomolecules Printing in One Step Using a PDMS Macrostamp," Microelectronic Engineering, vol. 86, 2009, pp. 1428-1430.
LeBerre, M., et al., "From Convective Assembly to Landau Levich Deposition of Multilayered Phospholipid Films of Controlled Thickness," Langumuir, vol. 25, No. 5, 2009, pp. 2554-2557.
Lenhert, S., et al., "Capillary-Induced Contact Guidance," Langmuir, vol. 23, 2007, pp. 10216-10223.
Li, B., "Patterning Colloidal metal Nanoparticles for Controlled Growth of Carbon Nanotubes," Advanced Materials, vol. 20, 2008, pp. 4873-4878.
Li, B., "Nanoscale-Controlled Enzymatic Degradation of Poly (L-lactic acid) Films Using Dip-Pen Nanolithography,: "Small, vol. 7, No. 2, 2001, pp. 226-229.
Linder V., et al., "Rapid Prototyping of 2D Structures with Feature Sizes Larger than 8 um," Anal. Chem., vol. 75, 2003, pp. 2522-2527.
Lv, X., et al., "Variations in Lipid Yields and Compositions of Marine Microalgae During Cell Growth and Respiration, and Within Intracellular Structures," Journal of Experimental Maine Biology and Ecology, vol. 391, 2010, pp. 73-83.
Mathger, L.M., et al., "Mechanisms and Behavioural Functions of Structural Coloration in Cephalopods," Journal of the Royal Society, Interface, 2009, pp. S149-S163.
Maxfield, F.R., et al., "Role of Cholesterol and Lipid Organization in Disease," Nature, vol. 438, Dec. 1, 2005, pop. 612-621.
Mennicke, U., et al., "Preparation of Solid-Supported Lipid Bilayers by Spin-Coating," Langmuir, vol. 18, 2002, pp. 8172-8177.
Michel, B., et al., "Printing Meets Lithography: Soft Approaches to High-Resolution Patterning," IBM J. Res. & Dev., vol. 45, No. 5, Sep. 2001, pp. 697-719.
Mrksich M. et al., "Patterning of Self-Assembled Monolayers Using Microcontact Printing: A New Technology for Biosensors?" Trends Biotechnology, vol. 13, 1995, pp. 228-235.
Nafday, O.A., et al., "Site-Specific Dual Ink Dip Pen Nanolithography," Scanning, vol. 32, 2009, pp. 122-126.
Peterson, E.J., et al., "Effect of Environmental Conditions on Dip-Pen Nanolithography of Mercaptohexadecanoic Acid," Journal of Physics Chem. B., vol. 108, 2004, pp. 15206-15210.
Pompeo, G., et al., "AFM Characterization of Solid-Supported Lipid Multilayers Prepared by Spin-Coating," Biochimica et Biophysica Acta 1712, 2005, pp. 29-36.
Qin, D., et al. "Soft Lithography for Micro- and Nanoscale Patterning," Nature Protocols, vol. 5, No. 3, 2010, pp. 191-502.
Saha, S.K., "Characterization of the Dip Pen Nanolithography Process for Nanomanufacturing," Fournal of Manufacturing Science and Engineering, vol. 133, Aug. 2011, pp. 041005-1-041005-9.
Scheib, M., et al., "Fluorescence Excitation on Monolithically Integrated All-Polymer Chips," Journal of Biomedical Optics, vol. 15(4), Jul.-Aug. 2010, pp. 041517-1-041517-5.
Scheres, L., et al., "Micro- and Nanopatterning of Functional Organic Monolayers on Oxide-Free Filicon by Laser-Induced Photothermal Desorption," Small, vol. 6, No. 17, 2010, pp. 1918-1926.

(56) References Cited

OTHER PUBLICATIONS

Sharp, K.G., "Effect of Stamp Deformation on the Quality of Microcontact Printing: Theory and Experiment," Langmuir, vol. 20, 2004, pp. 6430-6438.
Shen, Q., et al., "Control and Implementation of a Real-Time Liquid Spotting System for Microarray Applications," IEEE Transactions on Industrial Electronics, vol. 55, No. 9, Sep. 2008, pp. 3266-3272.
Shi, J., et al., "Microcontact Printing and Lithographic Patterning of Electrospun Nanofibers," Langmuir, vol. 25(11), 2009, pp. 6015-6018.
Strobel, M., et al., "Plasma Fluorination of Polyolefins," Journal of Polymer Science: Part A: Polymer Chemistry, vol. 25, 1987, pp. 1295-1307.
Sweetlove, L.J., et al., "The Mitochondrion: An Integration Point of Cellular Metabolism and signalling," Critical Reviews in Plant Sciences, vol. 26, No. 1, 2007, pp. 17-43.
Tavares, L., et al., "Efficient Roll-On Transfer Technique for Well-Aligned Organic Nanofibers," Small, vol. 7, No. 17, 2011, pp. 2460-2463.
Ten Grotenhuis, E., "Scanning Force microscopy of Cholesterol Multilayers Prepared With the Spin-Coating Technique," Colloids and Surfaces B: Biointerfaces, vol. 6, 2009, pp. 209-218.
Trapp, M., et al., "Hydration Dependent Studies of Highly aligned Multilayer Lipid Membranes by Neutrol Scattering," The Journal of Chemical Physics, 133, 2010, pp. 164505-1-164505-7.
Wang, Y., et al., "A Self-Correcting Inking Strategy for Cantilever Arrays Addressed by an Inkjet Printer and Used for Dip-Pen Nanolithography," Small, vol. 4, No. 10, 2008, pp. 1666-1670.
Yang, S.Y., et al., "Stimuli-Responsive Hybrid Coatings of olyelectrolyte Multilayers and Nano-Patterned Polymer Brushes," Macromolecular Rapid Communications, vol. 29, 2009, pp. 729-736.
Zhang, H., et al., "High-Throughput Dip-Pen-Nanolithography-Based Fabrication of Si Nanostructures," Small, vol. 3, No. 1, 2007, pp. 81-85.
Zheng, Z., et al., Topographically Flat, Chemically Patterned PDMS Stamps Made by Dip-Pen Nanolithography,: Angew. Chem. Int. Ed., vol. 47, 2008, pp. 9951-9954.
Santhanam, V., "Microcontact Printing of Uniform Nanoparticle Arrays," Nano Letters, vol. 4, No. 1, 2004, pp. 41-44.
Banerjee, P., Indian J. Biochem. Biophys. vol. 30, 1993, p. 358.

\* cited by examiner

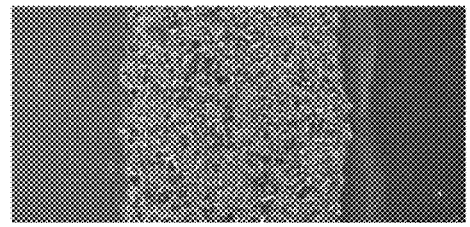
DOTAP – 1 hr
FIG.70
DOTAP – 24 hr
FIG.71    7112
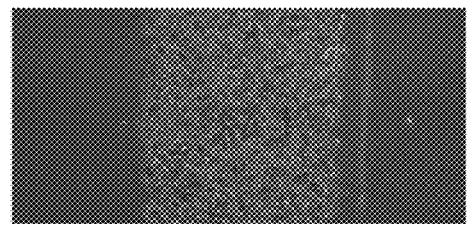
Docetaxel – 1 hr
FIG.72
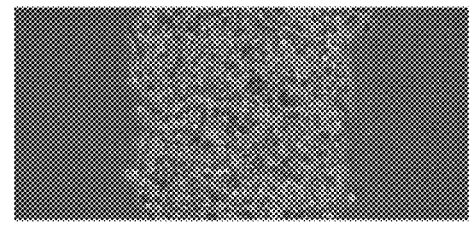
Docetaxel – 24 hr
FIG.73
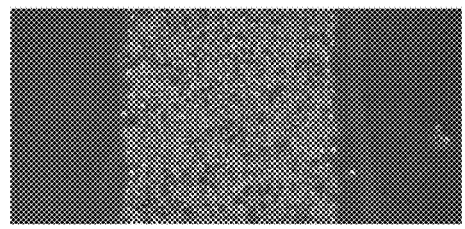
Brefeldin A – 1 hr
FIG.74
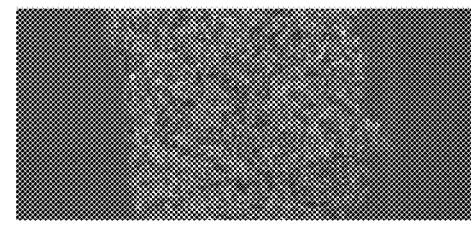
Brefeldin A – 24 hr
FIG.75

EVAPORATIVE EDGE LITHOGRAPHY OF A LIPOSOMAL DRUG MICROARRAY FOR CELL MIGRATION ASSAYS

CROSS-REFERENCE TO RELATED APPLICATIONS

This application claims benefit of priority to U.S. Provisional Patent Application No. 61/841,980, entitled "EVAPORATIVE EDGE LITHOGRAPHY (EEL) OF A LIPOSOMAL DRUG MICROARRAY FOR CELL MIGRATION ASSAYS," filed Jul. 2, 2013, and International Application No. PCT/IB2013/055762, entitled "SCALABLE LIPOSOME MICROARRAY SCREENING" filed Jul. 12, 2013, which in turn claims priority to U.S. Provisional Patent Application No. 61/671,214, entitled "SCALABLE LIPOSOME MICROARRAY SCREENING" filed Jul. 13, 2012. The entire contents and disclosures of these patent applications are incorporated herein by reference in their entirety.

This application makes reference to U.S. Provisional Patent Application No. 61/383,775, entitled "HIGH THROUGHPUT OPTICAL QUALITY CONTROL OF PHOSPHOLIPID MULTILAYER FABRICATION VIA DIP PEN NANOLITHOGRAPHY (DPN)," filed Sep. 17, 2010. U.S. Provisional Patent Application No. 61/387,764, entitled "NOVEL DEVICE FOR DETECTING AND ANALYZING AQUEOUS SAMPLES," filed Sep. 21, 2010. U.S. Provisional Patent Application No. 61/387,550, entitled "LIPID MULTILAYER GRATINGS," filed Sep. 29, 2010. U.S. Provisional Patent Application No. 61/387,556, entitled "LIPID MULTILAYER GRATINGS FOR SEMI-SYNTHETIC QUORUM SENSORS," filed Sep. 29, 2010. U.S. Provisional Patent Application No. 61/451,619, entitled "IRIDESCENT SURFACES AND APPARATUS FOR REAL TIME MEASUREMENT OF LIQUID AND CELLULAR ADHESION," filed Mar. 11, 2011. U.S. Provisional Patent Application No. 61/451,635, entitled "METHODS AND APPARATUS FOR LIPID MULTILAYER PATTERNING," filed Mar. 11, 2011. U.S. Provisional Patent Application No. 61/501,298, entitled "LIPOSOME MICROARRAY SURFACE AND THEIR USE FOR CELL CULTURE SCREENING," filed Jun. 27, 2011. U.S. patent application Ser. No. 13/234,540, entitled "OPTICAL METHOD FOR MEASURING HEIGHT OF FLUORESCENT PHOSPHOLIPID FEATURES FABRICATED VIA DIP-PEN NANOLITHOGRAPHY," filed Sep. 11, 2011. U.S. patent application Ser. No. 13/238,498, entitled "INTEGRATED DEVICE FOR ANALYZING AQUEOUS SAMPLES USING LIPID MULTILAYER," filed Sep. 21, 2011. U.S. patent application Ser. No. 13/248,250, entitled "SEMI-SYNTHETIC QUORUM SENSORS," filed Sep. 29, 2011. U.S. Provisional Patent Application No. 61/570,490, entitled "LIPID MULTILAYER MICROARRAYS FOR IN VITRO LIPOSOMAL DRUG DELIVERY AND SCREENING," filed Dec. 14, 2011. U.S. Provisional Patent Application No. 61/577,834, entitled "HIGH THROUGHPUT SCREENING METHOD AND APPARATUS," filed Dec. 20, 2011. U.S. Provisional Patent Application No. 61/577,910, entitled "NANOSTRUCTURED LIPID MULTILAYER FABRICATION AND DEVICES THEREOF," filed Dec. 20, 2011. U.S. patent application Ser. No. 13/417,650, entitled "IRIDESCENT SURFACES AND APPARATUS FOR REAL TIME MEASUREMENT OF LIQUID AND CELLULAR ADHESION," filed Mar. 12, 2012. U.S. patent application Ser. No. 13/417,588, entitled "METHODS AND APPARATUS FOR LIPID MULTILAYER PATTERNING," filed Mar. 12, 2012. U.S. patent application Ser. No. 13/534,772, entitled "LIPID MULTILAYER MICROARRAYS AND THEIR USE FOR CELL CULTURE SCREENING," filed Jun. 27, 2012. U.S. Provisional Patent Application No. 61/672,505, entitled "SURFACE SUPPORTED LIPOSOME NANOARRAYS AS BIOMIMETIC SENSORS," filed Jul. 17, 2012. International Patent Application No. PCT/IB2013/055884 to Lenhert et al., entitled "SURFACE SUPPORTED LIPOSOME NANOARRAYS AS BIOMIMETIC SENSORS," filed Jul. 17, 2013. The entire disclosure and contents of these patent applications are incorporated herein by reference.

BACKGROUND

Field of the Invention

The present invention relates liposomal microarrays.

Related Art

Current methods for analyzing cellular migration are limited by the number and type of different compounds and dosages that can be tested in parallel.

SUMMARY

According to a first broad aspect, the present invention provides a method comprising the following step: (a) forming one or more arrays of lipid multilayer structures on a substrate by evaporating a solvent from each of a plurality of lipid solutions in respective spaces between pairs of barriers on a substrate to thereby form the lipid multilayer structures along edges of the barriers, wherein each lipid solution of the plurality of lipid solutions comprises the solvent, one or more lipids and one or more drugs, and wherein each lipid multilayer structure of the lipid multilayer structures is a microstructure comprising the one or more lipids and the one or more drugs of one lipid solution of the plurality of lipid solutions.

According to a second broad aspect, the present invention provides a product comprising one or more arrays of lipid multilayer structures, wherein the product is formed by a method comprising the following step: (a) forming the one or more arrays of the lipid multilayer structures on a substrate by evaporating a solvent from each of a plurality of lipid solutions in respective spaces between pairs of barriers on a substrate to thereby form the lipid multilayer structures along edges of the barriers, wherein each lipid solution of the plurality of lipid solutions comprises the solvent and one or more lipids.

According to a third broad aspect, the present invention provides a method comprising the following step: (a) forming one or more arrays of lipid multilayer structures on a substrate by evaporating a solvent from each of a plurality of lipid solutions in respective openings in a stencil on a substrate to thereby form the lipid multilayer structures along respective peripheral edges of the openings, wherein each lipid solution of the plurality of lipid solutions comprises the solvent and, one or more lipids.

According to a fourth broad aspect, the present invention provides a product comprising one or more arrays of lipid multilayer structures, wherein the product is formed by a method comprising the following step: (a) forming one or more arrays of lipid multilayer structures on a substrate by evaporating a solvent from each of a plurality of lipid solutions in respective openings in a stencil on a substrate to thereby form the lipid multilayer structures along respective peripheral edges of the openings, wherein each lipid solution of the plurality of lipid solutions comprises the solvent and one or more drugs.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 70 is a micrograph of a HeLa cell strip (in phase contrast) in contact with a DOTAP only fluorescent lipid film (doped with 1 mol % DOPE-rhodamine), 1 hour after polydimethylsiloxane (PDMS) barriers were removed.

FIG. 71 is a micrograph of the HeLa cell strip of FIG. 70, 24 hours after the PDMS barriers were removed.

FIG. 72 is a micrograph of a HeLa strip incubated with a docetaxel encapsulated fluorescent lipid film, 1 hour after polydimethylsiloxane (PDMS) barriers were removed.

FIG. 73 is a micrograph of the HeLa cell strip of FIG. 72, 24 hours after the PDMS barriers were removed.

FIG. 74 is a micrograph of a HeLa strip incubated with a brefeldin A encapsulated lipid film, 1 hour after polydimethylsiloxane (PDMS) barriers were removed.

FIG. 75 is a micrograph of the HeLa cell strip of FIG. 74, 24 hours after the PDMS barriers were removed.

DETAILED DESCRIPTION OF THE PREFERRED EMBODIMENTS

Definitions

Figure 1:
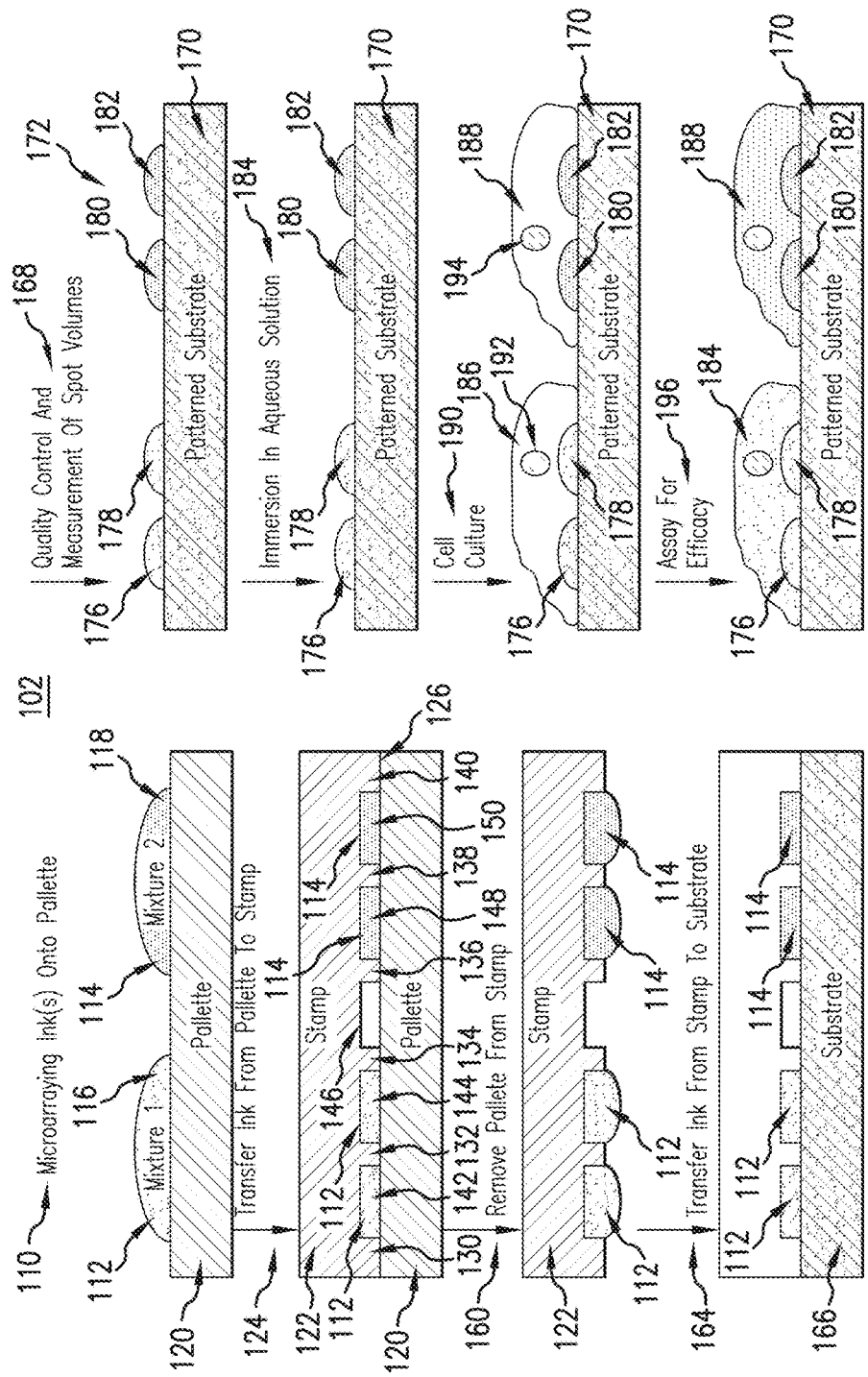
FIG. 1 is a schematic illustration showing the lipid multilayer stamping process used in this present invention.

Where the definition of terms departs from the commonly used meaning of the term, applicant intends to utilize the definitions provided below, unless specifically indicated.

For purposes of the present invention, it should be noted that the singular forms, "a," "an" and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, a value or property is "based" on a particular value, property, the satisfaction of a condition, or other factor, if that value is derived by performing a mathematical calculation or logical decision using that value, property or other factor.

For purposes of the present invention, the term "analyte" refers to the conventional meaning of the term "analyte," i.e., a substance or chemical constituent of a sample that is being detected or measured in a sample. In one embodiment of the present invention, a sample to be analyzed may be an aqueous sample, but other types of samples may also be analyzed using a device of the present invention.

For purposes of the present invention, the term "array" refers to a one-dimensional or two-dimensional set of microstructures and/or cell cultures. An array may be any shape. For example, an array may be a series of microstructures arranged in a line, such as an array of squares. An array may be arranged in a square or rectangular grid. There may be sections of the array that are separated from other sections of the array by spaces. An array may have other shapes. For example, an array may be a series of microstructures arranged in a series of concentric circles, in a series of concentric squares, a series of concentric triangles, a series of curves, etc. The spacing between sections of an array or between microstructures in any array may be regular or may be different between particular sections or between particular pairs of microstructures. The microstructure arrays of the present invention may be composed of microstructures having zero-dimensional, one-dimensional or two-dimensional shapes. The microstructures having two-dimensional shapes may have shapes such as squares, rectangles, circles, parallelograms, pentagons, hexagons, irregular shapes, etc. An array may be a set of pairs of microstructures. An array may be a set of microstructures wherein each microstructure of the set is in the shape of an enclosure.

For purposes of the present invention, the term "away" refers to increasing the distance between two aligned objects. For example, a contact controlling positioning device may be used to move: a stamp away from an ink palette, an ink palette away from a stamp, a stamp away from a substrate, a substrate away from a stamp, etc.

For purposes of the present invention, the term "barrier" refers to a structure that is used to control the flow of a lipid solution on a substrate. In one embodiment, a barrier may be made of an elastomeric material such as polydimethylsiloxane (PDMS), cellophane, polyurethanes, polyimides, and cross-linked Novolac™ resins (a phenol formaldehyde polymer). In other embodiments the barrier may be made of paraffin-based films, photoresists such as SU-8, or an epoxy. Although in the examples of the present invention described below and shown in the drawings, the barriers are rectangular-box shaped, barriers may be any shape such wedge-shaped, oval-shaped, cylindrical-shaped, tubular-shape, hexagonal, triangular-prism-shaped, pentahedron-shaped, star-shaped, etc. Although in the examples described below, the barriers are arranged in pairs, in some embodiments of the present invention the barriers may be isolated from each other allowing a lipid multilayer solution to be deposited along a single edge of the barrier to thereby form a lipid multilayer structure the edge of the barrier when the solvent of the lipid solution evaporates. Also, depending on the shape of a barrier, a lipid solution may deposited around the barrier to form a lipid multilayer structure around the barrier when the solvent of the lipid solution evaporates. For example, if the barrier is a cylinder that is stood on one of its ends on a substrate, such a procedure may be used to form a ring-shaped lipid multilayer structure around the cylinder.

For purposes of the present invention, the term "biomolecule" refers to the conventional meaning of the term biomolecule, i.e., a molecule produced by or found in living cells, e.g., a protein, a carbohydrate, a lipid, a phospholipid, a nucleic acid, etc.

For purposes of the present invention, the term "bound" and the term "bounded" refer to two or more lipid multilayer structures that define a region of a substrate between the two or more lipid multilayer structures by forming at least two "boundaries" between the bound region and an exterior region beyond the bound region. The bound region of the substrate may be filled with cell culture so that the lipid multilayer structures bounding the region also bound the cell culture. The cells may or may not also be present on top of the "boundaries" that bound a region of the substrate. For example, two lipid multilayer structures on two parallel sides of a region may define a region of the two lipid multilayer structures between the two multilayer structures and therefore, the two lipid multilayer structures "bound" the region. The two lipid multilayer structures may also bound a cell culture that fills the region. The fact that a pair of lipid multilayer structures may "bound" a cell culture does not mean that the lipid multilayer structures will prevent the cell culture from migrating across the lipid multilayer structures. For example, in one embodiment of the present invention, a pair of lipid multilayer structures, i.e., "boundaries," are formed along the edges of a pair of barriers of a stencil on a substrate to thereby "bound" a region on the substrate. When a cell culture is deposited in the opening of the substrate, the enclosure will "bound" the cell culture because the walls of the barriers of the stencil prevent the cells of the cell culture from being deposited beyond edges of the barriers. However, once the barriers of the stencil are removed, the cells of the cell culture may migrate beyond the lipid multilayer structures bounding the region of the substrate.

For purposes of the present invention, the term "boundary" refers to one lipid multilayer structure of a pair or a set of lipid multilayer structures that bound a region of a substrate.

For purposes of the present invention, the term "camera" refers to any type of camera or other device that senses light intensity. Examples of cameras include digital cameras, scanners, charged-coupled devices, CMOS sensors, photo-multiplier tubes, analog cameras such as film cameras, etc. A camera may include additional lenses and filters such as the lenses of a microscope apparatus that may be adjusted when the camera is calibrated.

For purposes of the present invention, the term "contacting surface" refers to a surface of a stamp that contacts a surface onto which a pattern comprising lipid ink is to be printed.

For purposes of the present invention, the term "detector" refers to any type of device that detects or measures light. A camera is a type of detector.

For purposes of the present invention, the term "dot" refers to a microstructure that has a zero-dimensional shape.

For purposes of the present invention, the term "drug" refers to a material that may have a biological effect on a cell, including but not limited to small organic molecules, inorganic compounds, polymers such as nucleic acids, peptides, saccharides, or other biologic materials, nanoparticles, etc.

For purposes of the present invention, the term "edge" refers where an edge of a stencil contacts a substrate. When used with respect to a barrier, the term "edge" refers to where the side of a barrier contacts a substrate. When used with respect to an opening in a stencil, the term "edge" refers to where the periphery of the opening contacts a substrate.

For purposes of the present invention, the term "encapsulated" refers to being confined by a lipid multilayer or partitioned within a lipid multilayer structure.

For purposes of the present invention, the term "enclosure" refers to a lipid multilayer structure that has the shape of a closed curve. A lipid multilayer structure in the shape of an enclosure may be formed by using stencil with openings. The stencil is placed on a substrate and a lipid solution having a solvent, one or more lipids and a drug is deposited in the openings of the stencil. When the solvent is evaporated, a lipid multilayer structure in the shape of an enclosure is formed around the edge of each opening where the opening contacts the substrate. An enclosure may be any shape such as circular, oval, square, rectangular, triangular, pentagonal, rectangular, crescent-shaped, star-shaped, lozenge-shaped, etc.

For purposes of the present invention, the term "fluorescence" refers to the conventional meaning of the term fluorescence, i.e., the emission of light by a substance that has absorbed light or other electromagnetic radiation of a different wavelength.

For purposes of the present invention, the term "fluorescent" refers to any material or mixture of materials that exhibits fluorescence.

For purposes of the present invention, the term "fluorescent dye" refers to any substance or additive that is fluorescent or imparts fluorescence to another material. A fluorescent dye may be organic, inorganic, etc.

For purposes of the present invention, the term "fluorescent microstructure" refers to a microstructure that is fluorescent. A fluorescent microstructure may be made of a naturally fluorescent material or may be made of a nonfluorescent material, such as a phospholipid, doped with a fluorescent dye.

For purposes of the present invention, the term "fluorescent nanostructure" refers to a nanostructure that is fluorescent. A fluorescent nanostructure may be made of a naturally fluorescent material or may be made of a nonfluorescent material, such as a phospholipid, doped with a fluorescent dye.

For purposes of the present invention, the term "fluid" refers to a liquid or a gas.

For purposes of the present invention, the term "freezing by dehydration" refers to removal of residual water content, for instance by incubation in an atmosphere with low water content, for instance a vacuum (<50 mbar) or at relative humidity below 40% (at standard temperature and pressure).

For purposes of the present invention, the term "grating" refers to an array of dots, lines, or a 2D shape that are regularly spaced at a distance that causes coherent scattering of incident light.

For purposes of the present invention, the term "groove" refers to an elongated recess in a stamp. A groove is not limited to a linear groove, unless clearly specified otherwise in the description below. The dimensions of a groove may change depending on the depth of the groove. For example, a groove may be wider at the top of the groove than at the bottom of the groove, such as in a V-shaped groove.

For purposes of the present invention, the term "groove pattern" refers to the pattern made by one or more grooves of a stamp.

For purposes of the present invention, the term "height" refers to the maximum thickness of the microstructure on a substrate, i.e., the maximum distance the microstructure projects above the substrate on which it is located.

For purposes of the present invention, the term "iridescent" refers to any structure that scatters light.

For purposes of the present invention, the term "iridescent microstructure" refers to a microstructure that is iridescent.

For purposes of the present invention, the term "iridescent nanostructure" refers to a nanostructure that is iridescent.

For purposes of the present invention, the term "irregular pattern" refers to a pattern of ridges and recesses that are not organized in a specific geometric pattern. For example, ridges and or recesses printed to resemble a picture of a human face, a picture of a leaf, a picture of an ocean wave, etc. are examples of irregular patterns. Using photolithography, almost any type of pattern for recesses and/or ridges may be formed in a stamp of the present invention.

For purposes of the present invention, the term "light," unless specified otherwise, refers to any type of electromagnetic radiation. Although, in the embodiments described below, the light that is incident on the gratings or sensors is visible light, the light that is incident on the gratings or sensors of the present invention may be any type of electromagnetic radiation, including infrared light, ultraviolet light, etc., that may be scattered by a grating or sensor. Although, in the embodiments described below, the light that is scattered from the gratings or sensors and detected by a detector is visible light, the light that is scattered by a grating or sensor of the present invention and detected by a detector of the present invention may be any type of electromagnetic radiation, including infrared light, ultraviolet light, etc. that may be scattered by a grating or sensor.

For purposes of the present invention, the term "light source" refers to a source of incident light that is scattered by a grating or sensor of the present invention. In one embodiment of the present invention, a light source may be part of a device of the present invention. In one embodiment a light source may be light present in the environment of a sensor or grating of the present invention. For example, in one embodiment of the present invention a light source may be part of a device that is separate from the device that includes the sensors and detector of the present invention. A light source may even be the ambient light of a room in which a grating or sensor of the present invention is located. Examples of a light source include a laser, a light-emitting diode (LED), an incandescent light bulb, a compact fluorescent light bulb, a fluorescent light bulb, etc.

For purposes of the present invention, the term "line" refers to a "line" as this term is commonly used in the field of nanolithography to refer to a one-dimensional shape.

For purposes of the present invention, the term "lipid" refers to hydrophobic or amphiphilic molecules, including but not limited to biologically derived lipids such as phospholipids, triacylglycerols, fatty acids, cholesterol, or synthetic lipids such as surfactants, organic solvents, oils, etc.

For purposes of the present invention, the term "lipid ink" refers to any material comprising a lipid applied to a stamp.

For purposes of the present invention, the term "lipid multilayer" refers to a lipid coating that is thicker than one molecule.

For purposes of the present invention, the term "lipid multilayer grating" refers to a grating comprising lipid multilayers.

For purposes of the present invention, the term "lipid multilayer structure" refers to a structure comprising one or more lipid multilayers. A lipid multilayer structure may include a dye such as a fluorescent dye.

For purposes of the present invention, the term "low humidity atmosphere" refers to an atmosphere having a relative humidity of less than 40%.

For purposes of the present invention, the term "lyotropic" refers to the conventional meaning of the term "lyotropic," i.e., a material that forms liquid crystal phases because of the addition of a solvent.

For purposes of the present invention, the term "microfabrication" refers to the design and/or manufacture of microstructures.

For purposes of the present invention, the term "microstructure" refers to a structure having at least one dimension smaller than 1 mm. A nanostructure is one type of microstructure.

For purposes of the present invention, the term "nanofabrication" refers to the design and/or manufacture of nanostructures.

For purposes of the present invention, the term "nanostructure" refers to a structure having at least one dimension on the nanoscale, i.e., a dimension between 0.1 and 100 nm.

For purposes of the present invention, the term "neat lipid ink" refers to a lipid ink consisting of a single pure lipid ink.

For purposes of the present invention, the term "pair of lipid multilayer structures" refers to two nearest neighbor lipid multilayer structures in an array of lipid multilayer structures. In one embodiment of the present invention, a pair of lipid multilayer structures may comprise the same lipid and contain the same drug at the same concentration.

For purposes of the present invention, the term "patterned substrate" refers to a substrate having a patterned array of lipid multilayer structures on at least one surface of the substrate.

For purposes of the present invention, the term "palette" refers to a substrate having one or more lipid inks that are made available to be picked up or drawn into the recesses or other topographical or chemical features of a stamp. The one or more lipid inks may be located in recesses, inkwells, etc. in the palette, or deposited onto a flat palette.

For purposes of the present invention, the term "palette spot" refers to a single spot of lipid link on a palette. A palette spot may be any shape.

For purposes of the present invention, the term "plurality" refers to two or more. So an array of microstructures having a "plurality of heights" is an array of microstructures having two or more heights. However, some of the microstructures in an array having a plurality of heights may have the same height.

For purposes of the present invention, the term "recess" refers to a recess of any size or shape in a stamp. A recess may have any cross-sectional shape such as a line, a rectangle, a square, a circle, an oval, etc. The dimensions of a recess may change depending on the depth of the recess. For example, a recess may be wider at the top of the recess than at the bottom of the recess, such as in a V-shaped recess. An example of a recess is a groove.

For purposes of the present invention, the term "recess pattern" refers to the pattern made by one or more recesses of a stamp.

For purposes of the present invention, the term "regular pattern" refers to a pattern of ridges and recesses organized in a specific geometric pattern. For example, a series of parallel recesses and/or lines is one example of a regular pattern. One or more arrays of ridges and recesses arranged in a square, a circle, an oval, a star, etc. is another example of a regular pattern.

For purposes of the present invention, the term "patterned array" refers to an array arranged in a pattern. A patterned array may comprise a single patterned array of lipid multilayer structures or two or more patterned arrays of lipid multilayer structures. Examples of patterned arrays of lipid multilayer structures are a patterned array of dots, a patterned array of lines, a patterned array of squares, etc.

For purposes of the present invention, the term "printing" refers to depositing a material, such as lipid ink, on a substrate.

For purposes of the present invention, the term "removing" refers to removing two objects from each other by moving one or both objects away from each other. For example, a stamp may be removed from a palette or substrate by moving the stamp away from the palette or substrate, by moving the palette or substrate away from the stamp or by moving both the stamp and the palette or substrate away from each other.

For purposes of the present invention, the term "ridge" refers to any raised structure. A ridge is not limited to a linear ridge, unless clearly specified otherwise in the description below. A ridge may have any cross-sectional shape such as a line, a rectangle, a square, a circle, an oval, etc. The dimensions of a ridge may change depending on the depth of a neighboring groove. For example, a ridge may be wider at the bottom of the ridge than at the top of the ridge, such as in a V-shaped ridge. A ridge may constitute the entire contacting surface of a stamp after recesses have been formed, etched, etc. into the stamp.

For purposes of the present invention, the term "scattering" and the term "light scattering" refer to the scattering of light by deflection of one or more light rays from a straight path due to the interaction of light with a grating or sensor. One type of interaction of light with a grating or sensor that results in scattering is diffraction.

For purposes of the present invention, the term "sensor" and the term "sensor element" are used interchangeably, unless specified otherwise, and refer to a material that may be used to sense the presence of an analyte.

For purposes of the present invention, the term "square" refers to a microstructure that is square in shape, i.e., has a two-dimensional shape wherein all sides are equal.

For purposes of the present invention, the term "stamped spot" refers to an area of a patterned surface of lipid nanostructures that originates from a single palette spot on an ink palette used as a source of lipid ink by stamp in depositing the lipid nanostructure. A stamped spot may be any shape.

For purposes of the present invention, the term "stencil" refers one or more structures placed on a substrate to define the shape of an array of lipid multilayer structures on the substrate using evaporative edge lithography (EEL). A stencil may be one piece or made of several pieces. In one embodiment of the present invention, a stencil may be a single piece with openings in which a lipid solution is deposited. In one embodiment of the present invention, a stencil may be several pieces with each piece including openings in which a lipid solution may be deposited. In one embodiment of the present invention, a stencil may be a set of barriers placed on a substrate in a pattern. In one embodiment, a stencil may be made of an elastomeric material such as polydimethylsiloxane (PMS).

For purposes of the present invention, the term "surface region" refers to a portion of a surface of a substrate between two lipid multilayer structures.

For purposes of the present invention, the term "surround" and the term "surrounded" refer to lipid multilayer structures that surround a region of a substrate or that surround a cell culture in a region of a substrate. For example, lipid multilayer structures that are enclosures may surround a region of a substrate and/or a cell culture in a region of the substrate. The fact that an enclosure may "surround" a cell culture does not mean that the enclosure will prevent the cell culture from migrating across the enclosure. For example, in one embodiment of the present invention, an enclosure comprising a lipid multilayer structure is formed along the edges of an opening in a stencil on a substrate to thereby "surround" a region on the substrate. When a cell culture is deposited in the opening of the substrate, the enclosure will "surround" the cell culture because the walls of the opening of the stencil prevent the cells of the cell culture from being deposited beyond edges of the opening. However, once the stencil is removed, the cells of the cell culture may migrate beyond the enclosure. Also, the when a cell culture is deposited in an opening, some of the cells may be deposited on top of the enclosure.

For purposes of the present invention, the term "topographically structured stamp" refers to a stamp having recesses that form one or more recess patterns. For simplicity, unless specifically indicated otherwise, the term "stamp" refers to a topographically structured stamp.

For purposes of the present invention, the term "toward" refers to decreasing the distance between two aligned objects. For example, a contact controlling positioning device may be used to move: a stamp towards an ink palette, an ink palette towards a stamp, a stamp towards a substrate, a substrate towards a stamp, etc.

Description

Liposomes or vesicles are three-dimensional, self-organized, nanostructured lipid particles that are widely used as drug- and gene-delivery vehicles.[1-7] The use of lipids as delivery vectors for delivery of materials to cells has become a widely studied field due to the potential of utilizing them to deliver both lipophilic and hydrophilic drugs and nutrients through liposomes.[8,9] The efficiency of delivery from solution using cationic phospholipids has been extensively studied making them a prime material for efficient delivery of materials into cells. Liposomes have been found to enhance the efficacy of anticancer drugs. There is evidence that lipid composition affects cellular uptake and the ability for the drug to kill cancer cells.

Lipid multilayer microstructures and nanostructures are a type of nanomaterial that are effectively multilamellar liposomes confined to a surface. This allows analysis and assays developed for lipid bilayers to be applied to multilayered liposome like structures, which are capable of encapsulating materials. One application of these materials is in the fabrication of small molecule microarrays for drug screening, where drugs encapsulated in the lipid multilayer nanostructures can be delivered to cells cultured on these surfaces for screening of drug efficacy in a microarray format.[10]

Microarraying techniques have been very successful in biotechnology for carrying out a large number of experiments on a single surface. Microarrays of different types of lipids have been proposed for molecular screening applications.[11,12] Spotting techniques are typically used to create arrays of lipid bilayers that are composed of different lipid materials on a surface that allows lipid-bilayer formation.[13,14] Methods of fabricating lipid multilayer microarrays include dip-pen nanolithography (DPN),[15,16,17,18] dewetting on a prepatterned surface,[19] and photothermal patterning,[20] microcontact printing,[21] and lipid multilayer stamping.[22] Micro- and nanostructured lipid multilayers on surfaces hold the promise of combining certain properties of solution-based liposomes with surface-based capabilities.

Most microarrays take the approach of covalently linking the molecule to be screened to the surface, or confining the molecules of interest to a two-dimensional lipid bilayer. The liposome microarray technology described here provides a small, yet three-dimensional volume in which encapsulated molecules are dispersed. For drug screening applications, this allows the delivery of candidate molecules to the cell for internalization at concentrations relevant to clinical dosages. Microarray technology, however, has been thoroughly developed for integrating a large number of different multiple materials onto a surface. This approach has been particularly successful for DNA microarrays, where DNA molecules are covalently linked to the surface. Microarray techniques include the use of piezo-based inkjet dispenser systems for depositing molecules like DNA onto substrates and pin based fluid transfer systems. In addition, photolithographic methods have been used for in situ high density DNA microarray fabrication by DNA synthesis on the chip, for instance by companies like Affymetrix® which increase the number of experiments that can be done on these arrays without compromising on the quality of the experiments.[23,24] The use of microfluidics has also seen success in increasing the throughput of biochemical analysis by using aqueous drops dispersed in oil as picoliter reaction vessels to identify new mutants of the enzyme horseradish peroxidase and screening at the rate of ~$10^8$ individual reactions in 10 hours.[25] Microarrays have also been applied to the patterning of antibodies and lipids. Stainless steel pins have been used for printing microarrays of DNA and proteins. Dip-pen nanolithography (DPN) is a method that uses the tip from an AFM to deliver materials to a surface in a direct writing process, and it can fabricate arbitrary structures from a variety of molecular inks.[26-29] The use of masks is not required, and sub-100-nm resolution can be achieved.[29] DPN is also capable of high throughput when carried out with parallel tip arrays.[30,31] Similar approaches to nanosurface and microsurface patterning include soft lithography[32] and polymer pen lithography.[33] Previous work has established the concept of using surface supported multilayers as carriers for lipophilic cancer drugs to cells.[34] The feasibility of delivery of materials to cells from lipid multilayer patterns created with dip-pen nanolithography (DPN) has been established. DPN is a method that uses an atomic force microscope tip to deliver materials to a surface, with lateral resolution well below 1 micron. DPN can be carried out with parallel tip arrays for large area fabrication. Furthermore, multiple materials can be simultaneously delivered to a surface from different tips in parallel arrays, for instance using microfluidic channels to ink the tips, or microarray technology to deliver the different lipid inks to the AFM tips.

When carried out with lipid-based inks, DPN is capable of forming lipid multilayer nanostructures, where the multilayer thickness can be controlled. Multilayer thickness is particularly important for delivery applications because it allows encapsulation of materials such as drug candidates within the multilayers. Although DPN is well suited for prototype fabrication due to its ability to directly write arbitrary patterns, there are currently practical limits to its scalability for multi-material patterning. For instance, for small molecule microarray applications in drug screening, it would be desirable to have hundreds of thousands of different small molecules integrated onto a single surface. The ability for DPN to multiplex has been demonstrated for 24 different lipid inks,[35] but the scalability of that process has yet to be shown.

Lipid multilayer stamping uses a structured polymeric stamp to print lipid multilayer structures onto a surface.[22] It combines several aspects of well-established microfabrication methods in a new approach that is uniquely suited for lipid multilayer nanofabrication. In particular, lipid multilayer stamping combines the lateral patterning capabilities and scalability of microcontact printing[32], with the topographical control of nanoimprint lithography[36] to create nanostructured lipid multilayer arrays. A disadvantage of lipid multilayer stamping is that it requires pre-fabrication of a master, necessitating DPN to identify the optimal stamp geometry. Once that is determined, lipid multilayer stamping is a scalable method capable of mass production of lipid multilayer microarrays.

In one embodiment, the present invention provides the combination of scalable pin-spotting microarray technology with the process of lipid multilayer stamping in order to generate nanostructured lipid multilayer microarrays capable of screening liposomal formulations of a drug, such as the anticancer drug Docetaxel. In order to improve spot uniformity and scalability, an ink palette is used to ink the structured stamp. Since spots composed of lipid nanostructures are used in this technique, the term "stamped spot" refers to an area of the final patterned surface that originated from a single palette spot on the ink palette. The finer structures that make up each of the stamped spots are referred to as nanostructures, as the thickness of these structures is on the order of 10-100 nanometers with the lateral dimensions typically being several micrometers. In order to overcome the limitations of DPN and take advantage of the high throughput capabilities of microarray technology, lipid multilayer stamping may be employed. In this approach, lipids are arrayed onto a structured elastomeric stamp, which is then used to create lipid multilayer patterns. In order to make this invention applicable in a high throughput manner, microarraying techniques have to be adapted to increase the number of different materials that can be printed onto desired substrates using this stamping method.

In one embodiment, the present invention provides a device comprising: a lipid multilayer microarray suitable for screening of liposomal drug formulation on a chip; a method and apparatus for assaying for drug efficacy.

In one embodiment, the present invention provides a combination pin-spotting microarray technology with lipid multilayer stamping.

In one embodiment, the present invention provides a method to quantify cellular uptake of labeled materials.

In one embodiment, the present invention provides a method and apparatus of immersion of the array into a solution by adding the water in an inert atmosphere. For instance, a microwell plate could be sealed to contain an inert gas, and the solution injected into this atmosphere.

In one embodiment, the present invention provides a method and apparatus for simultaneously delivering different lipid-encapsulated materials in arrays.

In one embodiment, the present invention provides a method and apparatus for preventing cross-contamination of lipid-encapsulated materials in arrays.

In one embodiment, the present invention provides a method and apparatus for assaying for cell response to materials delivered from the microarray.

In one embodiment, the present invention provides a method and apparatus for localizing K562 leukemia cells from stamped drug-encapsulated lipid multilayers.

In one embodiment, the present invention provides a method of delivery of anticancer drug to leukemia cells from stamped drug-encapsulated lipid multilayers.

In one embodiment, the present invention provides a method for assaying the efficacy of lipid multilayer delivered drugs to leukemia cells.

In one embodiment, the present invention provides a method and apparatus for monitoring and controlling cell migration using fluorescently labeled lipid multilayers.

FIG. 1 depicts a general overview of a microarraying procedure 102 according to one embodiment of the present invention for creating lipid multilayer patterns that may have a nanometer resolution in height. As shown in step 110 of FIG. 1, a microarrayer (not shown in FIG. 1) deposits lipid inks 112 and 114 as palette spots 116 and 118, respectively on a palette 120. Palette spots 116 and 118 form a microarray on palette 120. After deposition, palette 120 is used to transfer lipid inks 112 and 114 from palette spots 116 and 118, respectively, to a topographically structured polymeric stamp 122, as shown in step 124. Stamp 122 includes a topographically structured surface 126 comprising ridges 130, 132, 134, 136, 138 and 140 and grooves 142, 144, 146, 148 and 150. Lipid ink 112 from palette spot 116 is forced into grooves 142 and 144. Lipid ink 114 from palette spot 118 is forced into grooves 148 and 150. At step 160, ink palette 120 is removed from stamp 122 so that at least some lipid ink 112 of palette spot 116 is retained in grooves 142 and 144 and so that at least some lipid ink 114 of palette spot 118 is retained in grooves 148 and 150. Palette 120 may be removed from stamp 122 by moving palette 120 away from stamp 122, by moving stamp 122 away from palette 120 or by moving palette 120 and stamp 122 away from each other. At step 164 stamp 122 is placed in contact with a substrate 166 to transfer lipid ink 112 in grooves 142 and 144 and lipid ink 114 in grooves 148 and 150 to substrate 166. At step 168, stamp 122 is removed from substrate 166 to form a patterned substrate 170 comprising substrate 166 and a patterned array 172 on substrate 166. Stamp 122 may be removed from substrate 166 by moving stamp 122 away from substrate 166, by moving substrate 166 away from stamp 122 or by moving stamp 122 and substrate 166 away from each other. Patterned array 172 comprises stamped spots 176, 178, 180 and 182. Stamped spots 176, 178, 180 and 182 are each a lipid microstructure. Stamped spot 176 is formed from lipid ink 112 in groove 142. Stamped spot 178 is formed from lipid ink 112 in groove 144. Stamped spot 180 is formed from lipid ink 114 in groove 148. Stamped spot 182 is formed from lipid ink 114 in groove 150. The spot volumes of stamped spots 176, 178, 180 and 182 on patterned substrate 170 are measured for quality control. After measuring stamped spots 176, 178, 180 and 182 for quality control, patterned array 172 of patterned substrate 170 is immersed in an aqueous solution containing cells at step 184 to deposit cells on patterned array 172. Cells 186 and 188 from the aqueous solution are shown deposited on patterned array 172 in step 190. Cells 186 and 188 have respective nuclei 192 and 194. Cells 186 and 188 are then be used to assay for liposomal drug efficacy in step 196.

Although in FIG. 1, the cells are shown being deposited on the patterned substrate by immersing the patterned array in an aqueous solution containing the cells, the cells may be deposited on the patterned substrate by other means. For example, the cells may be to deposit the cells in a dehydrated stated on the patterned substrate.

In one embodiment of the present invention, a cellular assay may involve detection of a cellular response to drug exposure and can include second messenger assays, reporter gene assays, cell proliferation assays, and high content screening. Second messenger assays monitor signal transduction from activated cell-surface receptors that can measure fast transient fluorescent signals. Reporter gene assays monitor cellular responses at the transcription/translation level, which indicate the presence or absence of a gene product that reflects changes in a signal transduction pathway. Cell proliferation assays are quick and easily employed for automation because they measure the overall growth, no growth, or death responses of the cell to external stimuli. Lastly, high content screening analyzes cells using fluorescence based reagents that yield multi-parametric measurements of subcellular events. For example, measurement of apoptosis that provides information such as nuclear size and morphological changes, nuclear DNA content, mitochondrial potential, and actin-cytoskeletal rearrangements during drug-induced programmed cell death.[40]

Figure 2:
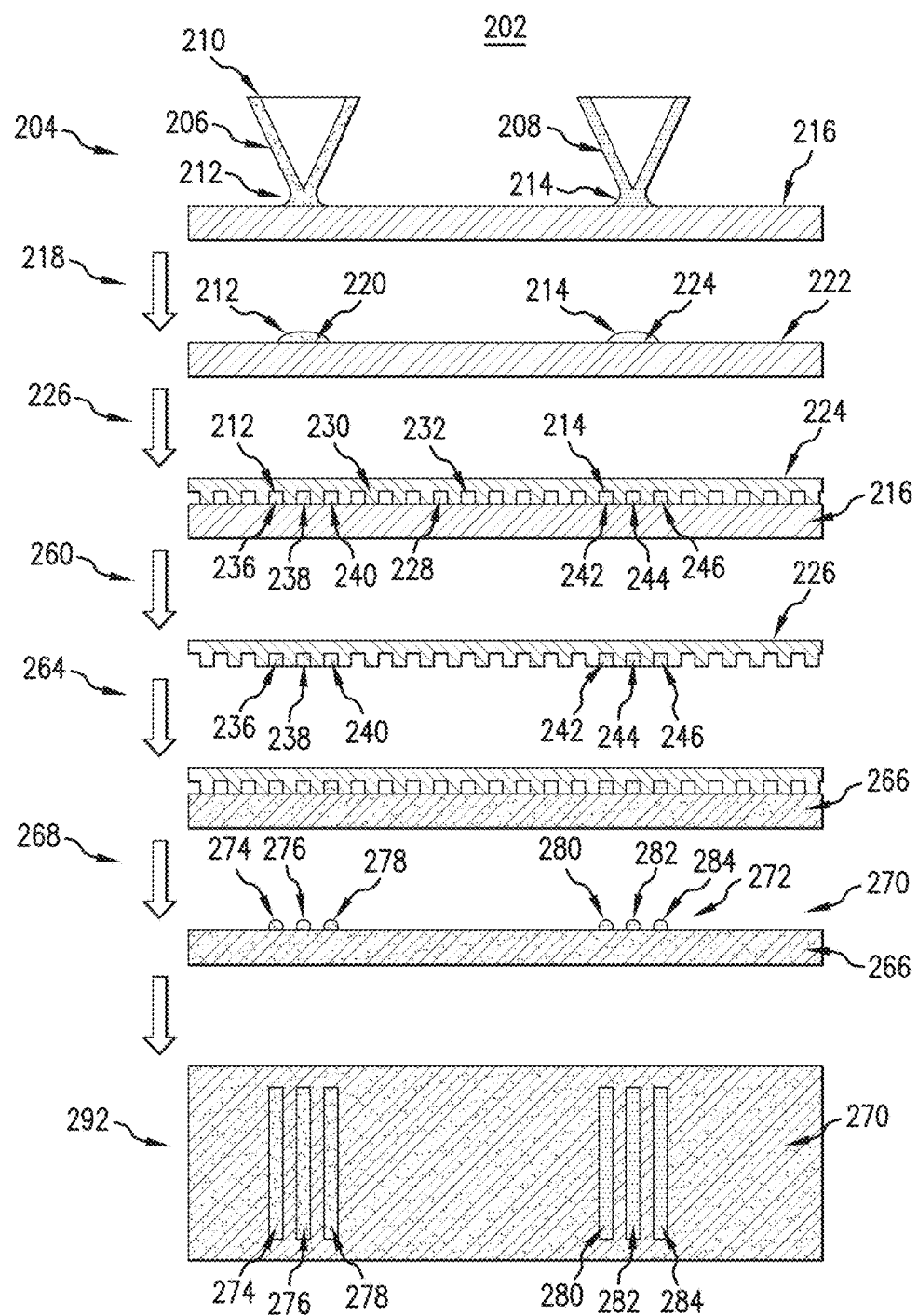
FIG. 2 is a schematic illustration of the process of scalable lipid multilayer stamping.

FIG. 2 depicts a general overview of a microarraying procedure 202 according to one embodiment of the present invention. As shown in step 204 of FIG. 2, tips 206 and 208 of a microarrayer 210 deposit respective lipid inks 212 and 214 on a palette 216. At step 218, microarrayer 210 is removed from palette 216 leaving palette spots 220 and 222 on palette 216. Microarrayer 210 may be removed from palette 216 by moving microarrayer 210 from palette 216, by moving palette 216 away from microarrayer 210 or by moving microarrayer 210 and palette 216 away from each other. Palette spot 220 consists of lipid ink 212. Palette spot 222 consists of lipid ink 214. Palette spots 220 and 222 spots form a microarray on palette 216. After deposition, palette 216 is used to transfer lipid inks 212 and 214 to a topographically structured polymeric stamp 224, as shown in step 226. Stamp 224 includes a topographically structured surface 228 comprising ridges 230 and grooves 232. Lipid ink 212 from palette spot 220 is forced into grooves 236, 238 and 240 of grooves 232. Lipid ink 214 from palette spot 222 is forced into grooves 242, 244 and 246 of grooves 232. At step 260, ink palette 216 is removed from stamp 224 so that at least some lipid ink 212 of palette spot 220 is retained in grooves 236, 238 and 240 and at least some lipid ink 214 of palette spot 222 is retained in grooves 242, 244 and 246. Palette 216 may be removed from stamp 224 by moving palette 216 away from stamp 224, by moving stamp 224 away from palette 216 or by moving palette 216 and stamp 224 away from each other. At step 264 stamp 224 is placed in contact with a substrate 266 to transfer lipid ink 212 in grooves 236, 238 and 240 and lipid ink 114 in grooves 242, 244 and 246 to substrate 266. At step 268, stamp 224 is removed from substrate 266 to form a patterned substrate 270 comprising substrate 266 and a patterned array 272 on substrate 266. Stamp 224 may be removed from substrate 166 by moving stamp 224 away from substrate 266, by moving substrate 266 away from stamp 224 or by moving stamp 224 and substrate 266 away from each other. Patterned array 272 comprises stamped spots 274, 276, 278, 280, 282 and 284. Stamped spots 274, 276, 278, 280, 282 and 284 are each a lipid microstructure. Stamped spot 274 is formed from lipid ink 212 in groove 236. Stamped spot 276 is formed from lipid ink 212 in groove 238. Stamped spot 278 is formed from lipid ink 212 in groove 240. Stamped spot 280 is formed from lipid ink 214 in groove 242. Stamped spot 282 is formed from lipid ink 214 in groove 244. Stamped spot 284 is formed from lipid ink 214 in groove 246. The spot volumes of stamped spots 274, 276, 278, 280, 282 and 284 on patterned substrate 270 are measured for quality control. As can be seen in view 292, spots 274, 276, 278, 280, 282 and 284 are elongated in shape.

Although in FIGS. 1 and 2 for simplicity of illustration all of the lipid ink in each of the spots is shown being forced into the grooves of the stamp, in other embodiments of the present invention, there may be much more lipid ink in the spots than is forced into the grooves of the stamp. For example, by providing more lipid ink in each of the spots of a palette, the palette may be used to print patterned arrays several substrates.

The lipid multilayer structures used in the arrays of the present invention may be microstructures or nanostructures. When cells are deposited on the patterned substrate, it is sometimes important that the stamped spots be smaller than each of the cells, so that the cells can adhere to the patterned substrate. However, for some types of cells, larger spots may be used. For example, suspension cells, such as the K652 cells shown in FIG. 36 may be adhered to patterned substrates having larger spots.

Microarraying lipid inks onto a polymeric ink palette increases the uniformity of lipid deposition from a microarrayer. Microarraying lipid inks on a palette also aids in the eventual deposition of lipids inks on the substrate by ensuring there is no excessive or inadequate ink deposition on the substrate. In addition ink palette with lipid inks arranged in a microarray may be used in order to ink multiple arrays. Microarraying technology enables lipid deposition to be controlled in a way such that creates a known array of multiple different lipid inks (multiplexing).

In addition to forming a microarray using pin spotting as shown in FIG. 2, other types of microarray technology may also be employed to form a microarray of the present invention. For example, a microarray of the present invention may be formed using inkjet printing, dip-pen nanolithography, etc.

In one embodiment of the present invention, each of the spots of the microarray of spots on the palette may be 0.01 to 5000 µm in diameter.

In one embodiment of the present invention, multilayer stamping in the form of 5 micrometer diameter dot patterns allows for sub-micron control of the lipid pattern thickness cross-sectional area.

Figure 3:
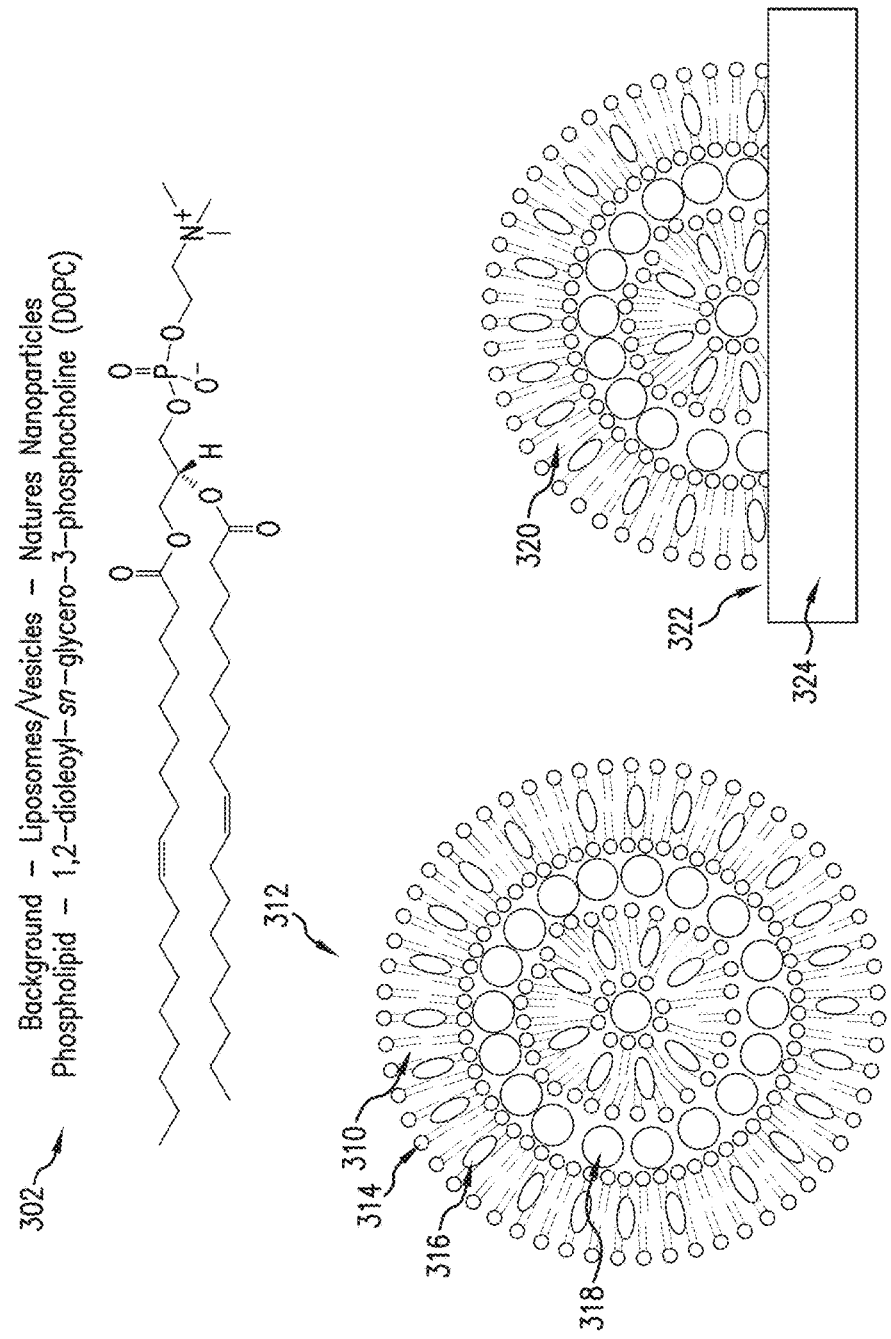
FIG. 3 is a diagram showing chemical and supramolecular structures of liposomes and surface-supported loaded lipid nanostructures and the chemical structure of 1,2-dioleoyl-3-trimethylammoniumpropane (chloride salt) (DOTAP).

FIG. 3 shows chemical and supramolecular structures of liposomes and surface-supported lipid nanostructures. The chemical structure of 1,2-dioleoyl-sn-glycero-3-phosphocholine (DOPC), a typical phospholipid that may be used in lipid microstructure of the present invention, is indicated by arrow 302. FIG. 3 also shows one example of one type of liposome supramolecular structure that self-assembles in water 312, i.e., multilamellar liposome 310 that is comprised of DOPC 314, non-polar drug molecule 316 and polar drug molecule 318. FIG. 3 also shows a surface-supported lipid multilayer liposome 320 on a surface 322 of substrate 324.

FIG. 3 shows one possible supramolecular structure and serves the purpose of comparing the structure of liposomes in solution with surface-supported liposomes or lipid multilayer nanostructures.

Figure 4:
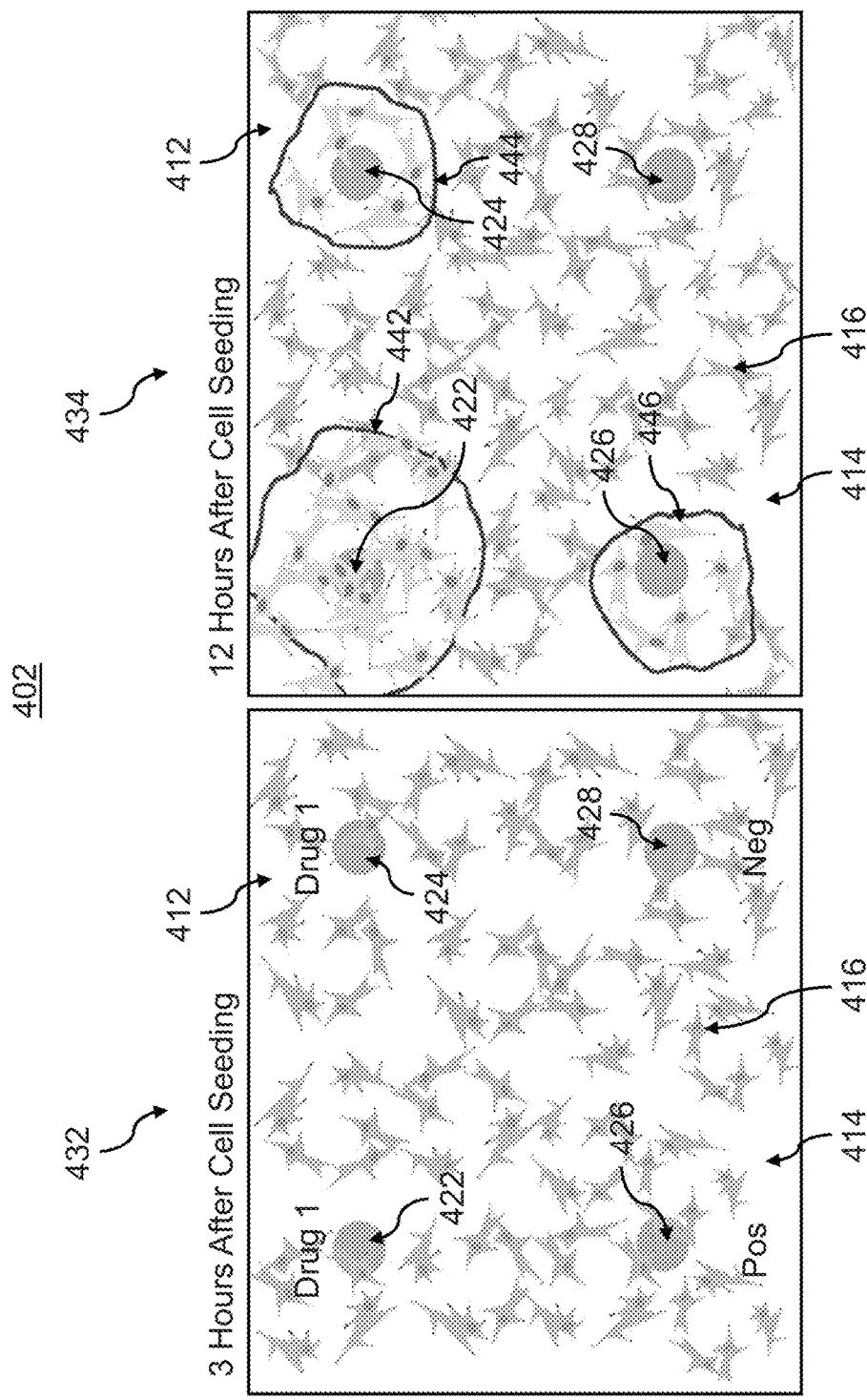
FIG. 4 illustrates an assay for cell migration that measures how far motile cells migrate from spots on a microarray.

FIG. 4 shows expected observation of cells that have been cultured on an array and allowed to migrate from the microarray spots. FIG. 4 shows a migration array assay 402 according to one embodiment of the present invention using an array 412 of spots on a substrate 414. Array 412 is covered with cells 416. Spots 422 and 424 of array 412 contain a drug and a fluorescent material to allow tracking of cell migration. Spot 422 contains a migration enhancing drug. Spot 424 contains a different migration enhancing drug. Spot 426 is a positive control containing a compound known to have positive effects on cell migration. Spot 428 is A negative control known to have negative effects on cell migration. Spots 422, 424, 426 and 428 are on substrate 414 using a microarraying technique of the present invention such as described above and shown in FIGS. 1 and 2. Cells 416 are "seeded," i.e., are deposited on top of spots 422, 424, 426 and 428. Illustration 432 shows array 412 three hours after cell seeding. Illustration 434 shows array 412 twelve hours after cell seeding. Circled region 442 shows the cells that have migrated around spot 422. Circled region 444 shows the cells that have migrated around spot 424. Circled region 446 shows the cells that have migrated around spot 426. No cells have migrated around spot 428. Based on the results show in FIG. 4 it may be determined that drug 1 enhances migration more than the positive control, and drug 2 enhances migration about the same amount as the positive control.

In one embodiment of the present invention, the topographically structured stamp may be a stamp made of polydimethylsiloxane (PDMS). Such a stamp may be made by pouring liquid PDMS over a silicon master. Other materials that may be used for a topographically structured stamp of the present invention include materials such as various types of plastics, various types of rubber, etc.

The patterned substrates of the present invention may be used in a variety of cellular assay methods. In one embodiment, an assay method of the present invention comprises the following steps: (1) Cells are seeded on the array; (2) Cells are allowed to grow; (3) The cells are stained (optional); and (4) Cells are counted and the number of cells on each spot is used as a measure of viability. In other embodiments of the present invention, steps 3 and 4 are replaced by second messenger assays, reporter gene assays, or high content screening methods.

Cell migration is a fundamental biological process important in angiogenesis, wound repair, and cancer metastasis. Current methods to analyze cellular migration are limited by the number and type of different compounds and dosages that can be tested in parallel. In one embodiment, the present invention provides a migration assay that allows for local delivery of multiple different dosages of the lipophilic drug docetaxel to cells in a microarray format. For this purpose, the present invention provides a technique to pattern lipid multilayers on surfaces called evaporative edge lithography (EEL). Carrying out this process with solutions of lipid and drug result in multilayers that can be taken up by adherent HeLa cells cultured on the array. Upon removal of the stencil, migration can be assayed much like a fencing assay, yet in a microarray format. Lipid patterning along the edges is found to be crucial for this assay because cells do not adhere to the lipid multilayer coated surfaces when the entire channels are filled. Our results demonstrate the assays compatibility with the lipophilic drug docetaxel, which was locally delivered to adherent HeLa cells from microarrays at various dosages in a way that allows measurement of cell migration inhibition. Unlike other migration assays, this approach makes it possible to screen different compounds and dosages on the same surface and is suitable for high throughput screening microarrays.

The migration of cells collectively is an important aspect of cancer metastasis,[41,42] angiogenesis,[43,44] wound healing,[45] and organismal development.[46,47] Several in vitro migration assays have been developed to assess the effects of compounds and microenvironmental conditions on the migration of cells in culture.[48,49] Examples include the commonly used wound or "scratch" migration assay,[48,50] removable fencing assays,[51] Boyden chamber assays,[52] biodegradable barriers,[53,54] and microfluidic techniques.[55,57] These methods have the common feature that cells are cultured on a certain part of a two-dimensional substrate or three-dimensional volume and allowed to migrate into a region without cells. The number or speed of individual or collectively migrating cells into the unpopulated regions is then measured. The scratch assay is the most commonly used method because it is simple and cheap.[48] Drawbacks of this assay, however, are inconsistency in the size of scratch areas within the cell culture monolayer and mechanical damage to the edge layer of cells and the substrate surface.[58] In an example of the fencing method of cell migration reported by Lenhert et al., cell growth was initially confined to a 5 mm diameter area for 2 days; the barrier was then removed; images were taken periodically after the cells were allowed to move freely onto uncovered areas of the substrate.[51] A similar assay using the commercially available Oris™ kit uses silicon stoppers as barriers that are placed on the bottom of 96-well microplates. This assay allows formation of precisely sized cell-free areas within the monolayer into which migration can occur without releasing factors from damaged or dead cells.[54] Another method to study cellular migration within the past decade is fabrication of microfluidic technologies in order to develop novel cell-based assays to precisely control multiple environmental factors simultaneously such as biochemical and biomechanical forces.[55,59-62] Huang et al. have used a microfluidic-based migration assay to induce wounds by partially detaching a confluent monolayer using laminar flows in the presence of trypsin.[57] Kwak et al. created a device to record individual HUVEC and NCI-H23 cell migration in real-time using optical microscopy assisted with computer software to collect data on cell size, migration path, distance and speed.[63] Other methods have also been described to track individual cells within a confluent population to demonstrate contact inhibition in Madin-Darby canine kidney (MDCK) epithelial cells or to gather information on individual cell migration in 3D models.[64,65]

Small molecule microarrays are a promising approach to miniaturizing high throughput screening that could allow tens to hundreds of thousands of compounds to be tested on a single cell culture plate.[66] Thousands of compounds have been screened for their effect on cellular migration by automated microscopy of scratch assays and by Boyden chamber assays.[52,67] It has previously been shown that lipid multilayer microarrays with subcellular lateral dimensions can be used as a format for delivery of multiple lipophilic anticancer drugs to adherent cells in a microarray format, and measured cytotoxicity as a readout for efficacy.[50] These arrays are capable of encapsulating drugs or drug candidates in an organic phase and preventing them from leaking into solution, yet allowing uptake by cells. Importantly, lipid multilayer microarrays are compatible with lipophilic compounds, while other drug screening microarrays are either limited to water soluble compounds that diffuse out of a gel into water,[68] or must be covalently linked to the surface and cannot be taken up by the cells.[69] High throughput screening is needed at the early stages of drug discovery and most drug candidates at this stage have low water solubility, which is quantified by a high octanol to water partition coefficient (Log P). In standard high throughput screening, dimethyl sulfoxide (DMSO) is used as solvent to deliver compounds with high Log P values in water,[70] yet DMSO can have undesirable effects on certain cell-based assays.[71,72] More importantly, DMSO cannot be used to deliver lipophilic drugs to cells from microarrays.

Previously, lipid multilayer patterns have been fabricated by dip-pen nanolithography (DPN),[15,16,73] soft lithography (e.g. micro-contact printing),[73,22] photothermal patterning,[20] and capillary assembly.[74] In one embodiment, the present invention provides a microarray-based migration assay that combines fencing with lipid multilayer drug delivery in vitro. For this purpose, the present invention provides a lipid multilayer fabrication method, i.e., edge evaporation lithography (EEL), that is capable of producing linear lipid multilayer nanostructures along the edge of a stencil. This method makes use of capillary assembly onto a pre-patterned surface in a way similar to that carried out by Diguet et al.,[74] with a difference being that EEL uses an edge between a stencil and a surface as a one-dimensional template rather than controlled evaporation on a chemically patterned surface.

In one embodiment, the present invention provides an edge evaporation lithography (EEL) method to fabricate a lipid-based drug delivery microarrays.

In one embodiment of the present invention, such microarrays may be suitable for the investigation of the effect of the antimicrotubule agent docetaxel on HeLa cell migration. Results demonstrate in vitro that docetaxel delivered into the cells locally from surface supported lipid films significantly inhibit cellular migration.

In one embodiment of the present invention, microarrays produced by EEL techniques may be used to study of the effects of poorly water soluble drugs on cell migration, structures and function.

In one embodiment of the present invention, microarrays produced by EEL techniques may be used for in vitro screening of a variety of different drugs for their effects on cells. This migration assay is unique in that multiple different compounds and dosages can be screened on the same surface, suitable for high throughput screening microarrays.

In one embodiment of the present invention, evaporative edge lithography may be used to produce linear lipid multilayer nanostructures along the edge of a stencil. The elastomeric stencil directs the precipitation of lipid and drug solutes (e.g. docetaxel) along an edge resulting in a drug-encapsulated lipid multilayer line that can deliver lipophilic drugs to adherent cells for migration assays. The thickness of these lipid films may be controlled to thereby control the dosage of material that is taken up by cells cultured over these areas. This is advantageous because unlike other migration assays, this approach makes it possible to screen different compounds and dosages on the same surface, with scalability for high throughput screening microarrays to assay for cell migration.

In one embodiment of the present invention, a drug or small molecules encapsulated within the lipid multilayer nanostructures may be delivered to cells only at the edge of the stencil because of the precipitation properties which can be important to selectively affect the migrating cells at the edge from non-migratory cells.

Evaporation induced self-assembly (EISA) is a related technique based on the evaporation of a solution containing precursors to be assembled. EISA has been used previously with lipid membranes.[75,76] In EEL, an elastomeric stencil (a set of barriers) is used to direct the precipitation of lipid and drug solutes along an edge resulting in a drug-encapsulated lipid multilayer line that can deliver lipophilic drugs to adherent cells for migration assays. Unlike other migration assays, this approach makes it possible to screen different compounds and dosages on the same surface, with scalability for high throughput screening microarrays.

Figure 5:
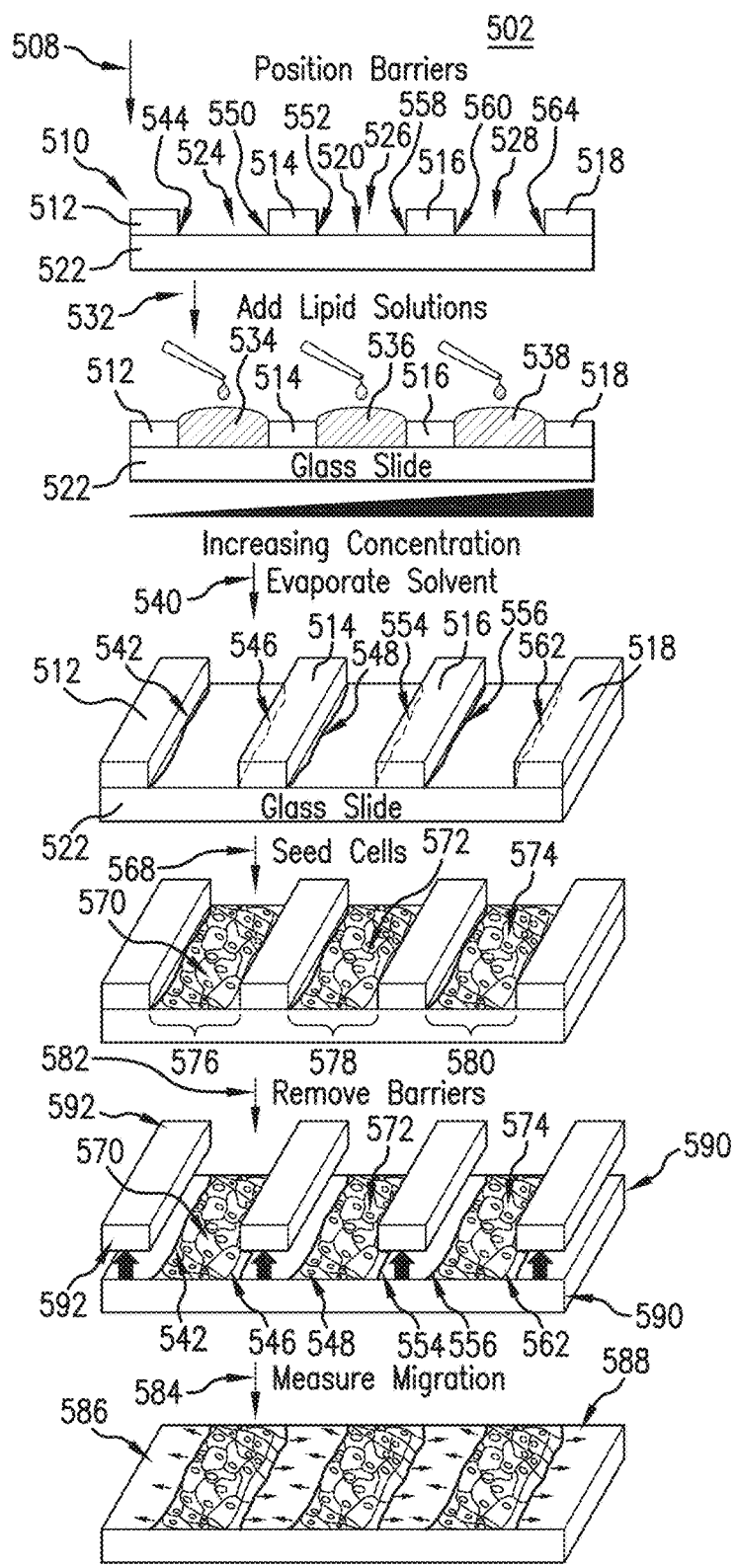
FIG. 5 is a schematic illustration of edge evaporation lithography and its use for microarrayed cell migration assay according to one embodiment of the present invention.

FIG. 5 shows an edge evaporation lithography (EEL) method 502 according to one embodiment of the present invention. At step 508 a stencil 510 comprising polydimethylsiloxane (PMS) barriers 512, 514, 516 and 518 is placed on a surface 520 of a substrate 522 to thereby form a space 524 between barriers 512 and 514, form a space 526 between barriers 514 and 516, and a space 528 between barriers 516 and 518. At step 532 spaces 524, 526 and 528 are filled with lipid solutions 534, 536 and 538, respectively, comprising a solvent containing a lipid mixed with a drug. The drug is present in solutions 534, 536 and 538 at three different concentrations. The concentration of the drug is higher in solution 536 than in solution 534. The concentration of the drug is higher in solution 538 than in solution 536. At step 540, the solvent is evaporated from solutions 534, 536 and 538 to thereby form lipid multilayer structure 542 along edge 544 of barrier 512, lipid multilayer structures 546 and 548 along edges 550 and 552 of barrier 514, lipid multilayer structures 554 and 556 along edges 558 and 560 of barrier 516, and lipid multilayer structure 562 along edge 564 of barrier 518. Lipid multilayer structures 542 and 546 are a pair of lipid multilayer structures having the same drug concentration. Lipid multilayer structures 548 and 554 are a pair of lipid multilayer structures having the same drug concentration. Lipid multilayer structures 556 and 562 form a pair of lipid multilayer structures having the same drug concentration.

At step 568, cell cultures 570, 572 and 574 respectively are seeded on surface regions 576, 578 and 580 of respective spaces 524, 526 and 528. Surface regions 576, 578 and 580 are three portions of surface 520 of substrate 522. Cell cultures 570, 572 and 574 are then cultured to confluence, i.e. to fill respective spaces 524, 526 and 528. At step 582, barriers 512, 514, 516 and 518 are removed. Cell culture 570 is bounded on two sides by a pair of nearest neighbor lipid multilayer structures, i.e., lipid multilayer structures 542 and 546. Cell culture 572 is bounded on two sides by a pair of nearest neighbor lipid multilayer structures, i.e., lipid multilayer structures 548 and 554. Cell culture 574 is bounded on two sides by a pair of nearest neighbor lipid multilayer structures, i.e., lipid multilayer structures 556 and 562.

Once barriers 512, 514, 516 and 518 are removed, cells of respective cell cultures 570, 572 and 574 are free to migrate as shown at step 584 and the migration of the cells of cell cultures 570, 572 and 574 is measured.

Lipid multilayer structures 542, 546, 548, 554, 556 and 562 are each microstructures and together form a microarray 586. Cell cultures 570, 572 and 574 together form an array 588 of cell cultures. Prior to cell migration, each cell culture of array 588 of cell cultures is bounded on two sides by two lipid multilayer structures. Once barriers 512, 514, 516 and 518 are removed, the cells of cell cultures 570, 572 and 574 are free to migrate across lipid multilayer structures 542, 546, 548, 554, 556 and 562.

In FIG. 5, there is sufficient surface adhesion between substrate 522 and lipid solutions 534, 536 and 538 and between barriers 512, 514, 516 and 518 and lipid solutions 534, 536 and 538 so that the lipid solution does not run off edges of 590 of substrate 522 between barriers 512, 514, 516 and 518. Ends 592 of barriers 512, 514, 516 and 518 are approximately flush with edges of substrate 522 in the embodiment shown in FIG. 5. But in some embodiments of the present invention, the ends of the barriers may not extend to the edges of the substrate.

In one embodiment of the present invention, the substrate of FIG. 5 may be a glass slide.

For simplicity of illustration, in FIG. 5, the microarray has three pairs of lipid multilayer structures having the same drug concentration. However, there may be any number of pairs of lipid multilayer structures having the same drug concentration in a microarray.

For simplicity of illustration, in FIG. 5, the microarray consists of three pairs of lipid multilayer structures having the same drug concentration. However, there may be any number of pairs of lipid multilayer structures having the same drug concentration in a microarray.

Figure 6:
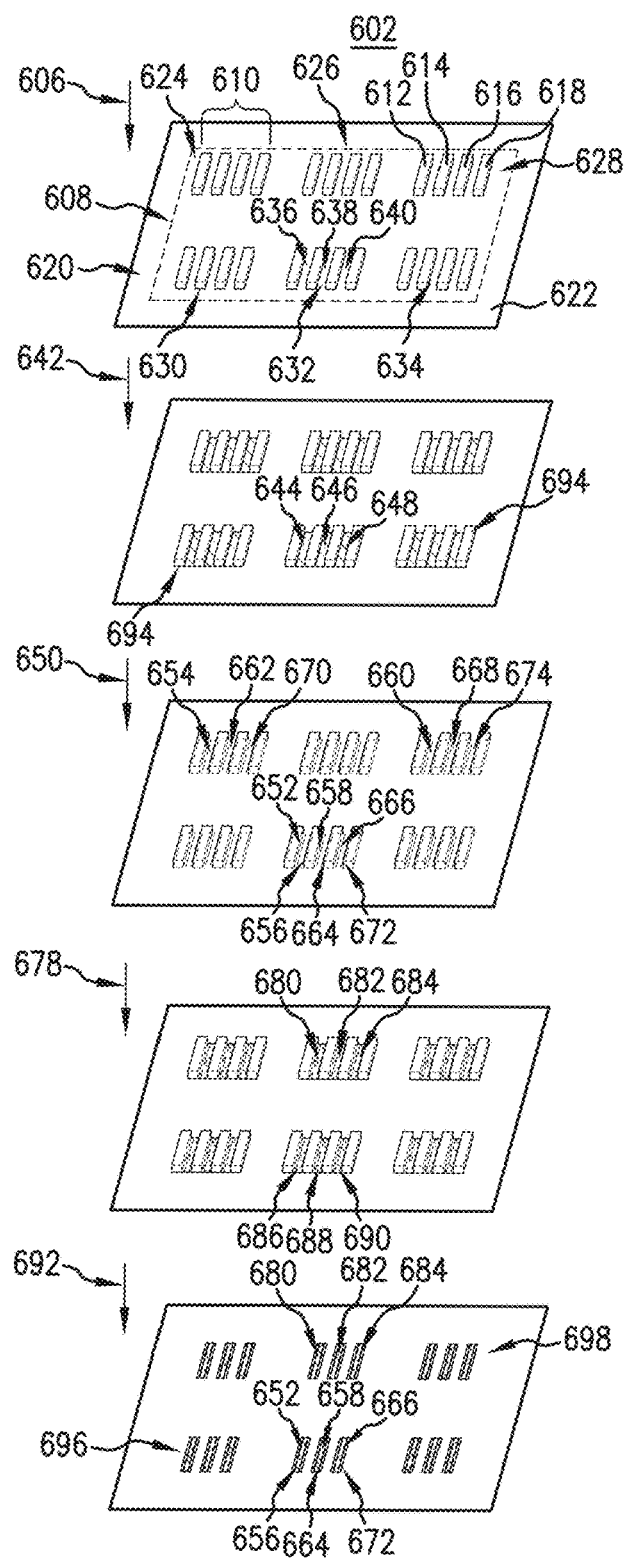
FIG. 6 is a schematic illustration of edge evaporation lithography and its use for microarrayed cell migration assay according to one embodiment of the present invention.

FIG. 6 shows an edge evaporation lithography (EEL) method 602 according to one embodiment of the present invention. At step 606 a stencil 608 comprising six sets 610 of polydimethylsiloxane (PMS) barriers 612, 614, 616 and 618 is formed on a surface 620 of a substrate 622 at six positions, i.e., position 624, position 626, position 628, position 630, position 632 and position 634. Between barriers 612 and 614 is a space 636, between barriers 614 and 616 is a space 638, between barriers 616 and 618 is a space 640. At step 642, spaces 636, 638 and 640 at each of the six positions are filled with lipid solutions 644, 646 and 648, respectively. Lipid solutions 644, 646 and 648 each comprise a solvent containing one or more lipids mixed with a drug. The concentration of the drug is higher is lipid solution 646 than in lipid solution 644 and is higher in 648 than in 646. A different drug is used in lipid solutions 644, 646 and 648 at each of the six positions.

At step 650, the solvent is evaporated from solutions 644, 646 and 648 to thereby form lipid multilayer structure 652 along edge 654 of barrier 612, lipid multilayer structures 656 and 658 along edges 660 and 662 of barrier 614, lipid multilayer structures 664 and 666 along edges 668 and 670 of barrier 616, and lipid multilayer structure 672 along edge 674 of barrier 618. Lipid multilayer structures 652 and 656 are a pair of lipid multilayer structures having the same drug concentration. Lipid multilayer structures 658 and 672 are a pair of lipid multilayer structures having the same drug concentration. Lipid multilayer structures 666 and 672 form a pair of lipid multilayer structures having the same drug concentration.

At step 678, cell cultures 680, 682 and 684, respectively are seeded on surface regions 686, 688 and 690 of respective spaces 636, 638 and 640. Surface regions 686, 688 and 690 are three portions of surface 620 of substrate 622. Cell cultures 680, 682 and 684 are then cultured to confluence, i.e. to fill respective spaces 636, 638 and 640.

At step 692, barriers 612, 614, 616 and 618 are removed at each of the six positions. At each of the six positions, cell culture 680 is bounded on two sides by a pair of nearest neighbor lipid multilayer structures, i.e., lipid multilayer structures 652 and 656. At each of the six positions, cell culture 682 is bounded on two sides by a pair of nearest neighbor lipid multilayer structures, i.e., lipid multilayer structures 658 and 664. At each of the six positions, cell culture 684 is bounded on two sides by a pair of nearest neighbor lipid multilayer structures, i.e., lipid multilayer structures 666 and 672. Once barriers 612, 614, 616 and 618 are removed, the cells of cell cultures 680, 682 and 684 are free to migrate across lipid multilayer structures 652, 656, 658, 664, 666 and 672.

Cells of respective cell cultures 680, 682 and 684 are then allowed to migrate. The migration rates of the cells at each of the six different positions may be measured, thereby allowing six different drugs to be assayed simultaneously.

In FIG. 6, there is sufficient surface adhesion between substrate 622 and lipid solutions 644, 646 and 648 at each of the six positions and between barriers 612, 614, 616 and 618 and lipid solutions lipid solutions 644, 646 and 648 at each of the six positions so that lipid solutions lipid solutions 644, 646 and 648 does not substantially disperse beyond ends 694 of barriers 612, 614, 616 and 618.

Lipid multilayer structures 652, 656, 658, 664, 666 and 672 are each microstructures. Each set of lipid multilayer structures 652, 656, 658, 664, 666 and 672 at each of the six positions on substrate 622 together form a microarray 696. The microarrays 696 at the six positions on substrate 622 together form a microarray of lipid multilayer structures.

Each set of cell cultures 680, 682 and 684 at each of the six positions on substrate 622 together form an array 698 of cell cultures. Prior to cell migration, each cell culture of the array 698 of cell cultures is bounded on two sides by two lipid multilayer structures. The arrays 698 of cell cultures at the six positions on substrate 622 together form an array of cell cultures.

For simplicity of illustration, in FIG. 6, each microarray at each of the six positions three pairs of lipid multilayer structures. However, there may be any number of pairs of lipid multilayer structures at each of the six positions.

Figure 7:
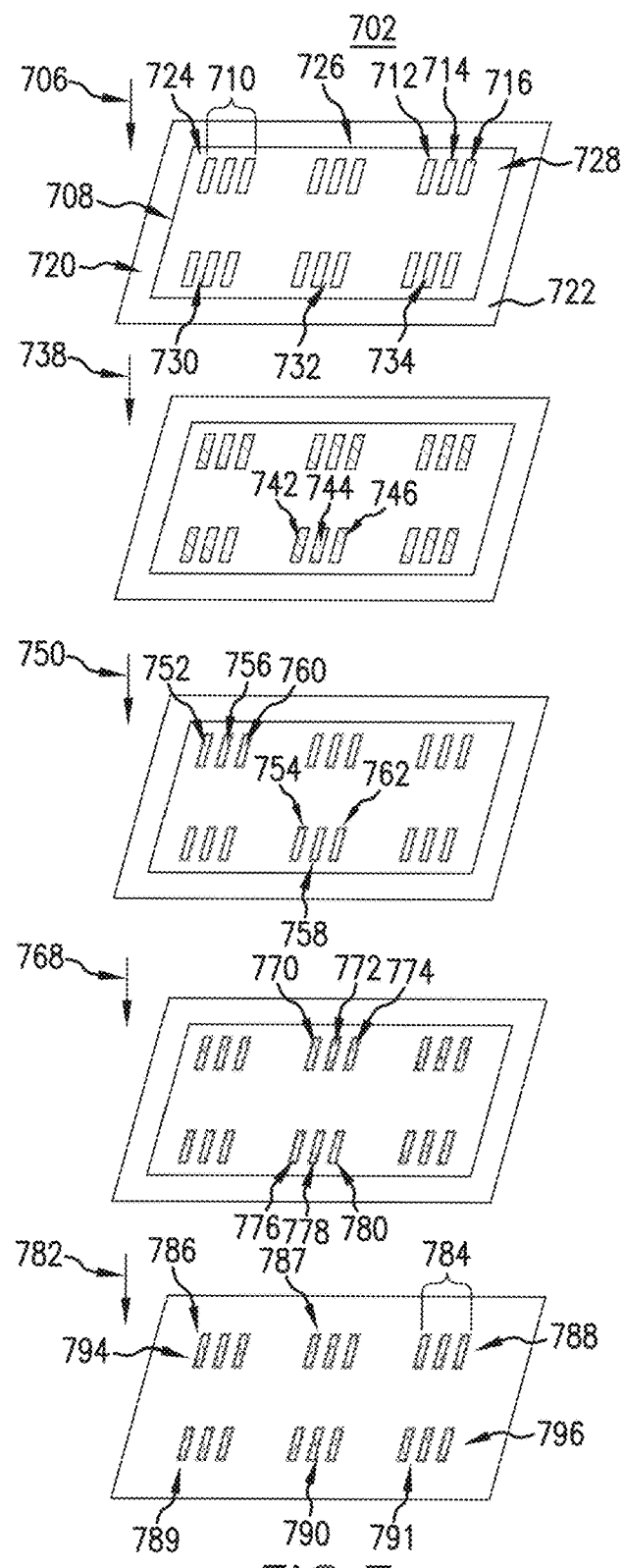
FIG. 7 is a schematic illustration of edge evaporation lithography and its use for microarrayed cell migration assay according to one embodiment of the present invention.

FIG. 7 shows an edge evaporation lithography (EEL) method 702 according to one embodiment of the present invention. At step 706 a stencil 708 comprising six sets 710 of openings 712, 714 and 716 are formed on a surface 720 of a substrate 722. Although for clarity of illustration, stencil 708 is shown as being substantially two-dimensional in FIG. 7, stencil 708 is actually three-dimensional, i.e., has a thickness similar to the way the barriers shown in FIGS. 5 and 6 each have a thickness. Sets 710 of openings 712, 714 and 716 are at six positions on stencil 708, i.e., position 724, position 726, position 728, position 730, position 732 and position 734. At step 738, openings 712, 714 and 716 at each of the six positions are filled with lipid solutions 742, 744 and 746, respectively. Lipid solutions 742, 744 and 746 each comprise a solvent containing one or more lipids mixed with a drug. The concentration of the drug is higher is lipid solution 746 than in lipid solution 744 and is higher in 748 than in 746. A different drug is used in lipid solutions 744, 746 and 748 at each of the six positions.

At step 750, the solvent is evaporated from solutions 744, 746 and 748 to thereby form lipid multilayer structure 752 along peripheral edge 754 of opening 712, lipid multilayer structure 756 along peripheral edge 758 of opening 714, and lipid multilayer structure 760 along peripheral edge 762 of opening 714. Lipid multilayer structures 752, 756 and 760 are each an enclosure.

At step 768, cell cultures 770, 772 and 774, respectively are seeded on surface regions 776, 778 and 780 surrounded by lipid multilayer structures, 752, 756 and 760, respectively. Surface regions 776, 778 and 780 are three portions of surface 720 of substrate 722. Cell cultures 770, 772 and 774 are then cultured to confluence, i.e. to fill surface regions 776, 778 and 780.

At step 782, stencil 708 is removed from substrate 722 to thereby form six arrays 784 of lipid multilayer structures 752, 756 and 760. Each lipid multilayer structure 752 surrounds a cell culture 770, each lipid multilayer structure 756 surrounds a cell culture 772, and each lipid multilayer structure 760 surrounds a cell culture 774. Arrays 784 are at six positions on substrate 722, i.e., positions 786, 787, 788, 789, 790 and 791.

Once stencil 708 is removed from substrate 722, cells of respective cell cultures 770, 772 and 774 are free to migrate across lipid multilayer structures 752, 756 and 760. The migration rates of the cells at each of the six different positions may be measured, thereby allowing six different drugs to be assayed simultaneously.

Lipid multilayer structures 752, 756 and 760 are each microstructures and therefore, arrays 784 are microarrays. Together, the six arrays 784 together form an array 794 of microstructures.

Each set of cell cultures 770, 772 and 774 at each of the six positions on substrate 722 together form an array 796 of cell cultures. The arrays of cell cultures at the six positions on substrate 722 together form an array of cell cultures over substrate 722.

For simplicity of illustration, in FIG. 7, each microarray at each of the six positions three lipid multilayer structures. However, there may be any number of lipid multilayer structures at each of the six positions.

The substrate used in the present invention may be any conventional substrate material used in cellular assays such as glass, functionalized glass, polystyrene, polymethylmethacrylate, etc. In one embodiment the substrate may be tissue culture plastic, i.e. a cell culture microplate.

Suitable solvents for use in the lipid solutions include ethanol.

The lipid solutions and lipid multilayer structures may each contain one lipid or two or more lipids. In one embodiment of the present invention, the lipid multilayer structures may be comprise 1,2-dioleoyl-3-trimethylammoniumpropane (chloride salt) (DOTAP).

The lipid solutions and lipid multilayer microstructures may each contain one drug or two or more drugs.

Using a method of the present invention using multiple microarrays of lipid multilayer structures, such as shown in FIGS. 6 and 7, allows for an increase in the number of tests that may be performed on a microplate. For example, the density is increased from being able to test one compound or concentration per well to 6 tests per square centimeter ($cm^2$), which can be used in standard 24 well cell culture microplates or in any microplate with a larger well area. The total number of tests that can be used in a 24 well microplate is 216 tests (assuming a well diameter of 1.5 cm). This number more than doubles the number of tests that can be performed on the widely used 96 well microplates.

A stencil of the present invention may be formed on a substrate in a variety of ways. For example, a stencil may be formed by replica molding from a master made by photolithography. In this process, the fluid elastomeric precursors are poured over a topographically structured silicon master. A cover can be placed on the silicon to press excess prepolymer out of the way. The prepolymer is cured and the stencil removed from the mask before placement onto the substrate. A stencil may also be stamped onto the substrate.

A stencil may be removed from a substrate by carefully peeling the stencil from one edge. The stencil can be peeled parallel, perpendicular or at an angle relative to the pattern axis.

Lipid solutions may be added to spaces between barriers by pipetting, or robotic spotting techniques such as pin spotting or inkjet printing.

The migration of cells may be measured optically by a microarray scanner, fluorescence or optical microscope, or by the naked eye.

A decrease or increase in the migration of cells beyond lipid multilayer structures bounding the cells indicates an effect of the drug in the lipid multilayer structures on the cells. The distance traveled by the edge of the cells from the starting point provides a measure of cell migration. The effects of different dosages of a drug can also be determined by the effects of lipid microstructures having different dosages of a drug on the migration of cells.

EXAMPLES

Materials and Methods
Chemical Structures

Figure 8:
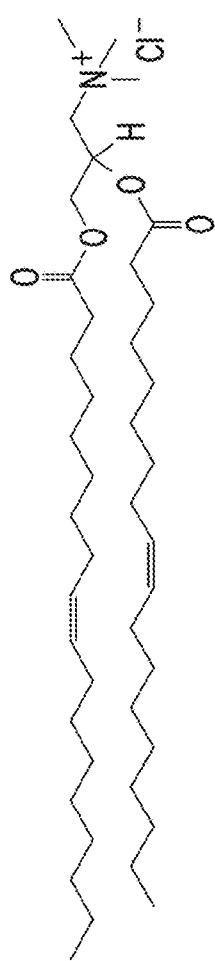
FIG. 8 shows the chemical structure of 1,2-dioleoyl-3-trimethylammonium-propane (chloride salt) (DOTAP).
Figure 9:
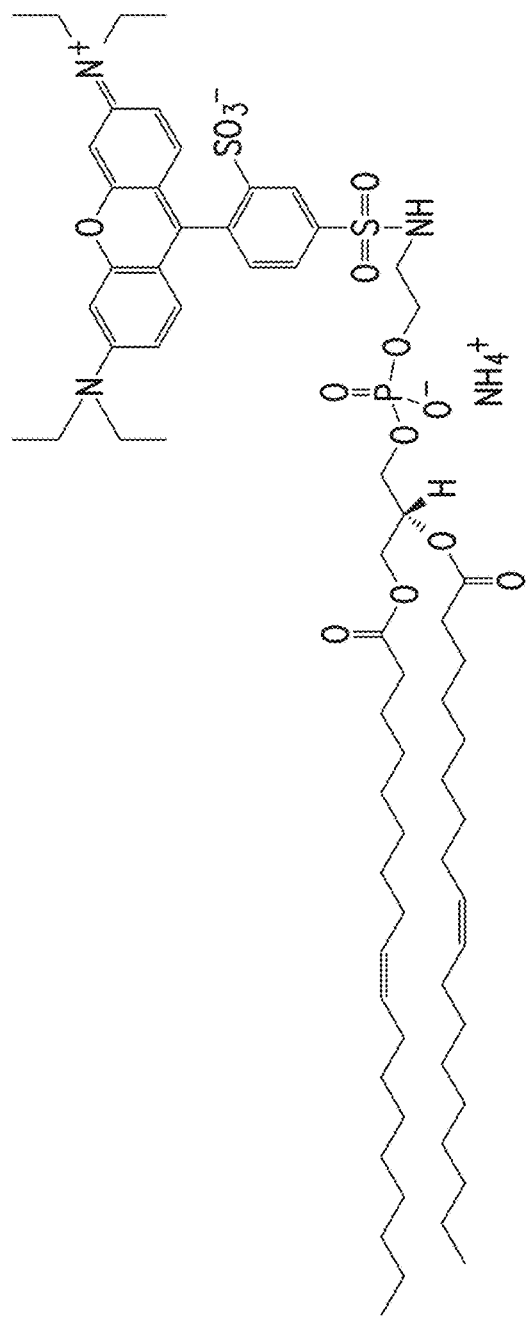
FIG. 9 shows the chemical structure of 1,2-dioleoyl-sn-glycerol-3-phosphoethanolamine-N-(lissamine rhodamine b sulfonyl) (ammonium salt) (DOPE-rhodamine).
Figure 10:
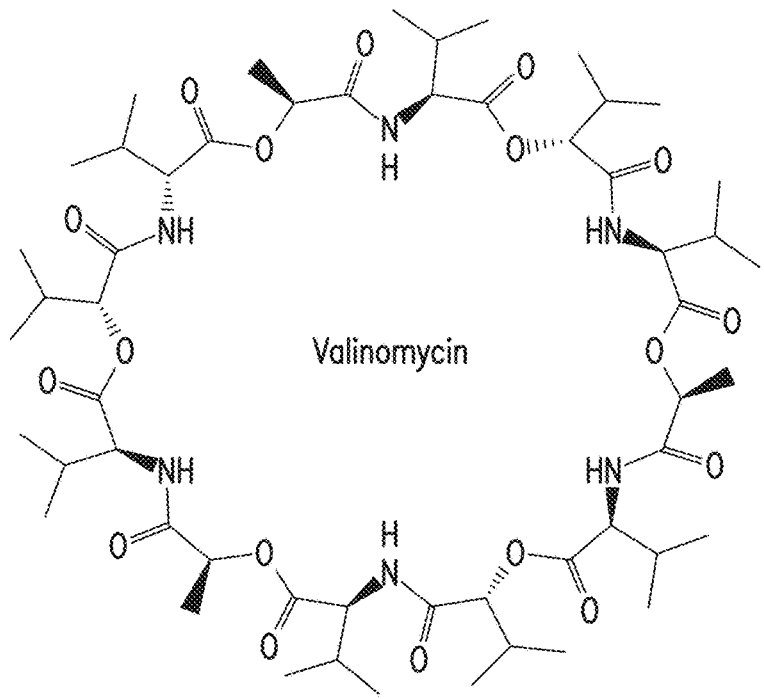
FIG. 10 shows the chemical structure of valinomycin.
Figure 11:
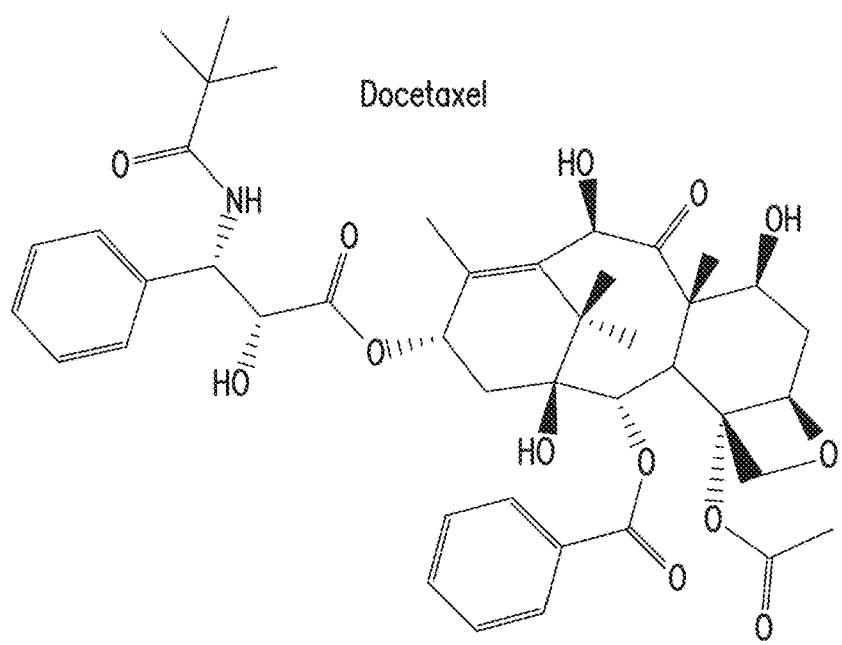
FIG. 11 shows the chemical structure of Taxotere® (docetaxel).

FIG. 8 shows the chemical structure of 1,2-dioleoyl-3-trimethylammonium-propane (chloride salt) (DOTAP). FIG. 9 shows the chemical structure of 1,2-dioleoyl-sn-glycerol-3-phosphoethanolamine-N-(lissamine rhodamine b sulfonyl) (ammonium salt) (DOPE-rhodamine or DOPE-RB). FIG. 10 shows the chemical structure of valinomycin. FIG. 11 shows the chemical structure of Taxotere® (docetaxel). DOTAP, DOPE-rhodamine, valinomycin and docetaxel are used in various examples below.

Liposome Ink Preparation

The lipids used for arraying and screening were 1,2-dioeoyl-snglycero-3-phosphocholine (DOPC), 1,2-dioleoyl-3-trimethylammonium-propane (chloride salt) (DOTAP), 1,2-dioleoyl-sn-glycero-3-phosphoethanolamine-N-lissamine rhodamine B sulfonyl (DOPE-RB). These lipids were purchased from Avanti Polar Lipids, Inc. 1,2-dihexadecanoyl-snglycero-3-phosphoethanolamine (Marina Blue DHPE) was purchased from Invitrogen. Solutions were prepared by mixing chloroform solutions of the different lipids to obtain the desired molar ratios. The chloroform was then evaporated off under a Nitrogen stream, followed by allowing the samples to dry further in the vacuum overnight in order to form a thin film of lipids on the bottom of the glass vials. After drying, water was added to the vials containing the dried lipid material and the samples were then lightly vortexed for 10 seconds and then sonicated for 10 minutes. Further vortexing after sonification was utilized as needed to ensure suspension of lipids in water.

Multiplexing

DOTAP was doped with 1 Mol % rhodamine-PE, Marina Blue DHPE and carboxyfluorescein-PE, respectively and were microarrayed in a 3×3 array pattern onto a PDMS ink pallet. The microarray pins were subjected to various wash times in order to determine the extent of any cross contamination between the two different lipid inks.

Microarraying

The different lipid solutions were microarrayed using a BioRobotics pinspotter model BG600 (Comberton, Cambridge, England) onto the desired substrate of choice, using a 200 micron 4×4 stainless steel solid pin tool.

Multilayer Stamping

DOTAP stamping was inked using the microarraying procedure onto an ink palette. Water was evaporated from the ink palette by leaving the sample in the vacuum overnight. The PDMS stamp was then inked by being placed into firm, uniform contact with the ink pallet. Once the PDMS stamp was inked, it was stamped onto a glass substrate. Uniform, firm pressure was applied to the stamp for ~20 seconds before careful removal from the surface.

Surfaces Used and Sample Preparation

γ-irradiated and Poly-d-lysine-coated Glass bottom Culture Dishes were obtained from MatTek Corporation. No. 1.5 mm, 22×22 mm coverslip substrates not used for cell culture were obtained from VWR and used straight out of the box.

Characterization and Imaging Techniques

A Ti-E epifluorescence inverted microscope (Nikon Instruments, Melville, N.Y.) fitted with a Retiga SRV (QImaging, Canada) CCD camera (1.4 MP, Peltier cooled to −45° C.) was used for fluorescence and brightfield imaging of the lipid nanostructures on glass surfaces. The heights and topography of the lipid prints were measured using tapping mode with a Dimension 3000 AFM (Veeco Instruments, Plainview, N.Y.) and tapping mode AFM cantilevers (#OMCLAC160TS-W2, 7 nm nominal tip radius, 15 µm tip height, 42 N m−1 spring constant, Olympus, Center Valley, Pa.). Noncontact mode AFM imaging is suitable for imaging micro- and nanoscopic fluid droplets.[39]

Miscellaneous Materials

Microarrayer, PDMS stamps (flat PDMS without wells on either surface, 5 µm, 1 µm wells), vacuum desiccators, DOTAP, DOPE, drugs (valinomycin, Taxotere), cells (HEK 293, HeLa, NIH 3T3), humidity chamber.

Stamp Printing

Lipid formulations were printed onto flat PDMS inkpad using the microarrayer with 800 µm spacing between the spots to be used as an inking pad. A PDMS stamp with 5 µm wells was then pressed against the inking pad. This was then placed in a vacuum overnight to remove any residual water from the wells. The stamp was then placed on a plasma-cleaned glass with the patterns against the glass slide and kept in a humidity chamber for 2 hours before being used for stamping.

Multilayer Stamping

The lipid dot pattern arrays were printed by placing the printed face of the inked PDMS stamp onto the substrate (glass) and pressing firmly against the substrate. Discernible patterns were achieved after the first few prints got rid of excess inking on the stamp.

Cell Culture

Introduction of the cells onto the patterned slide was done in a simple glove box with a low nitrogen stream with humidity at 10%. 500,000 cells were seeded into each well of the six-well plates to obtain 70% confluence over the pattern areas. The cells were incubated at 37° C. for 24 hours and 5% $CO_2$. Cells were assayed for viability.

Viability Assays

Cell viability was determined using the BacLight viability assay from Invitrogen®.

Preparation of Glass Coverslips for Patterning

Glass coverslips were prepared by cleaning first with detergent (Palmolive soap) and rinsed thoroughly with deionized water. Next the surfaces were subsequently cleaned with rinses in acetone, 100% ethanol, and deionized ultrapure Milli-Q water. Coverslips were dried with a steady stream of nitrogen gas and allowed to completely dry for at least 30 minutes in a biosafety cabinet.

Edge Evaporation Lithography

Polydimethylsiloxane (PDMS) was cured from the SYLGARD® 184 silicone elastomer kit in a 60° C. oven overnight. PDMS strips of 15 mm long by 1 mm wide were placed between 500-800 µm apart on prepared glass coverslips before addition of lipid mixtures. 1,2-dioleoyl-3-trimethylammonium-propane (chloride salt) (DOTAP) and 1,2- dioleoyl-sn-glycerol-3-phosphoethanolamine-N-(lissamine rhodamine b sulfonyl) (ammonium salt) (DOPE-rhodamine) were purchased from Avanti Polar Lipids. To create lipid only solutions, DOTAP was mixed with 1 molar percent (mol %) DOPE-rhodamine in chloroform and dried overnight in a vacuum pump desiccators at 16 LM 15 Torr 7.4 PSIG to remove solvent. Ethanol (100%) was added to suspend dried lipid powder and 1 μl was deposited in each PDMS channel and the array was dried overnight in a vacuum to remove residual ethanol. A similar procedure was used for docetaxel encapsulated lipid solutions and the drug was dissolved in ethanol prior to adding to the dried lipid powder.

Migration Assay Characterization

The free spaces in between PDMS stencils of the assay that contained lipid material were imaged with a G-2E/C red fluorescence filter. Characterization of the lipid films was performed by averaging the maximum intensity of 10 random cross sections on both edges of the barrier for a total of 20 samples using the freeware analysis software, ImageJ®. The middle of the channels was determined by 10 random cross sectional areas.

General Cell Culture and Staining

HeLa cells (obtained from the American Type Culture Collection and maintained according to the collections guidelines) for all experiments were seeded at $2.5 \times 10^5$ cells/ml and grown to approximately 70% confluence in growth media composed of Dulbecco's Modified Eagle Medium supplemented with 10% Cosmic Calf Serum. Cells were incubated at 37° C. and 5% $CO_2$. Trypsin with EDTA (0.25%) was used for cell detachment and the medium was replaced with fresh growth medium 24 hours before the experiment. Cells were stained for viability 20 minutes prior to imaging with SYTO9 and propidium iodide in Hank's buffered saline solution.

Cell Adhesion Experiments

Lipids were dissolved in ethanol and added to each channel in increasing amounts from 0.2 ng to 20 μg. Tests for cell attachment were performed by seeding HeLa cells into assay channel with varying amounts of lipid films. Cells were allowed to attach for two hours before washing the channels repeatedly 5 times. Prior to counting, cells were incubated with live-cell fluorescent dye (SYTO9, Invitrogen). The number of cells per square micron area ($\mu m^2$) that remained attached was counted manually. Experiments for cell adhesion where performed in three replicates. Values for cell density of each treatment were determined by averaging the number of cells in 5 random 100 $\mu m^2$ areas in a single image captured at a 4× magnification.

Cell Migration Assay of HeLa Cells

The prepared assays on glass coverslips were placed individually wells of a 6-well plate for cell culture. For experiments, cells were seeded onto the prepared patterned glass coverslips by gently pipetting the cell suspension ($2.5 \times 10^5$ cells/ml, 1 ml per coverslip) directly over each PDMS channel to allow cells to settle in them. The same method was used to seed other parts of the slide for use as control areas. Cells were allowed to settle for 1-2 hours before the PDMS barriers were removed to promote cell migration. After barrier removal, the coverslips were washed once with HBSS and replaced with fresh growth media. The cells were incubated over the patterned areas for up to 24 hours. Width of each cell strip was measure by hand with Nikon Elements 4.0 analysis software and the average migration rate for each strip was determined with the following equation:

$$\text{Migration Rate } (\mu m/hr) = (\text{Width}_{T=24\ hrs} - \text{Width}_{T=0\ hrs})/24 hrs.$$

Width is the average width in micrometers (μm) of the cell monolayer measured either at the beginning of the experiment (T=0 hrs) or at the end (T=24 hours).

Microscopy

The images for cell migration were captured on a Nikon Ti Eclipse inverted microscope with 4× or 10× objectives. Images for cell migration were taken after barrier removal and once again 24 hours after incubation period in phase contrast. Fluorescent filters used were B-2E/C and G-2E/C for red and green emitting dyes.

Statistical Analysis

A student t-test was performed to determine statistical significance between means of each sample (p-value <0.05). Error bars in figures are standard error of the mean for n samples. Characterizing the edge lipid films produced a total of n=20 samples and middle lipid film measurements produced n=10 samples. Cell density experiments were performed in triplicates (n=3). All samples for cell migration were taken in triplicate and replicated three times (n=9).

Example 1

Lipid multilayer stamping techniques of the present invention, when combined with microarray technology should allow for the increase in throughput of printing. Coating of PDMS stamps has been done by dipping in a solution of the desired material or by the peeling method where the stamp is put on a drop of the material and peeled off.[7] Using arrays of surface-supported liposomes for small molecule microarray screening is a very novel approach. FIGS. 12, 13, 13, 15, 16 and 17 show an illustration of liposomal structures in solution (state of the art) and on a surface using techniques of the present invention. These structures have similarities to solution based liposomes, which are well established lipid-based drug-delivery systems[37], especially for drugs that may be may be insoluble in water[6]. Fundamental differences include: (1) the ability to test multiple different materials on cells within the same solution by means of the microarray concept and (2) the micro and nanostructure can be readily characterized by optical and atomic force microscopy as the lipids are confined to a surface.

Figure 12:
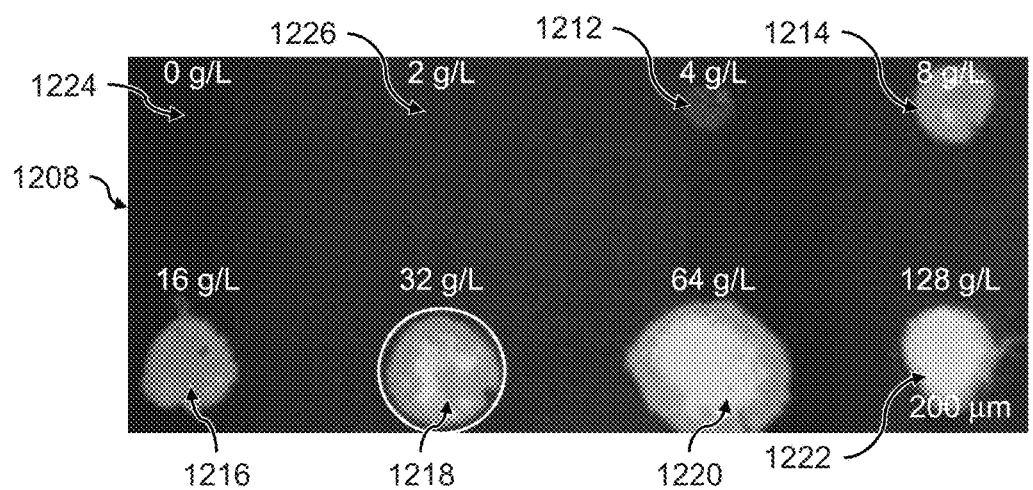
FIG. 12 shows a 4× red fluorescent image of Lipid Dot Patterns created from microarraying and multilayer stamping using a 5 μm well pattern at varying concentrations of DOTAP.

Characterization of lipid patterns were initially carried out with the cationic lipid, 1,2-dioleoyl-3-trimethylammonium-propane (chloride salt) (DOTAP). FIG. 12 shows a 4× red fluorescence image lipid patterning on glass substrate 1208 for a series of DOTAP concentrations doped with 1 Mol % rhodamine. Liposomal concentrations of 4 (1212), 8 (1214), 16 (1216), 32 (1218), 64 (1220) and 128 (1222) g/L provided adequate microarray deposition onto a PDMS ink palette. A control region 1224 includes no DOTAP. A liposomal concentration of 2 g/L (1226) was used, but failed to provide adequate transfer, just like control region 1224. The lipid patterns shown were created on the fourth print. Generally, higher concentrations require more preliminary prints in order to remove excess ink from the PDMS stamp.

Figure 13:
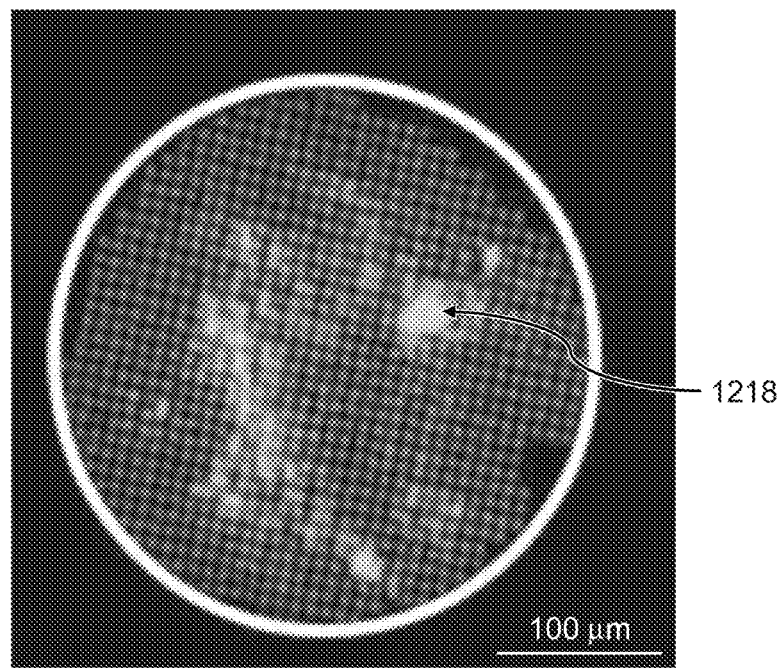
FIG. 13 is a fluorescent image of the lipid dot pattern created from 32 g/L concentration shown in FIG. 11.

FIG. 13 is a panel showing a 10× red fluorescence image of a DOTAP nanopattern created from the liposomal concentration of 32 g/L 1218. Non-uniform regions are shown, as well as uniform dots in the pattern.

Figure 14:
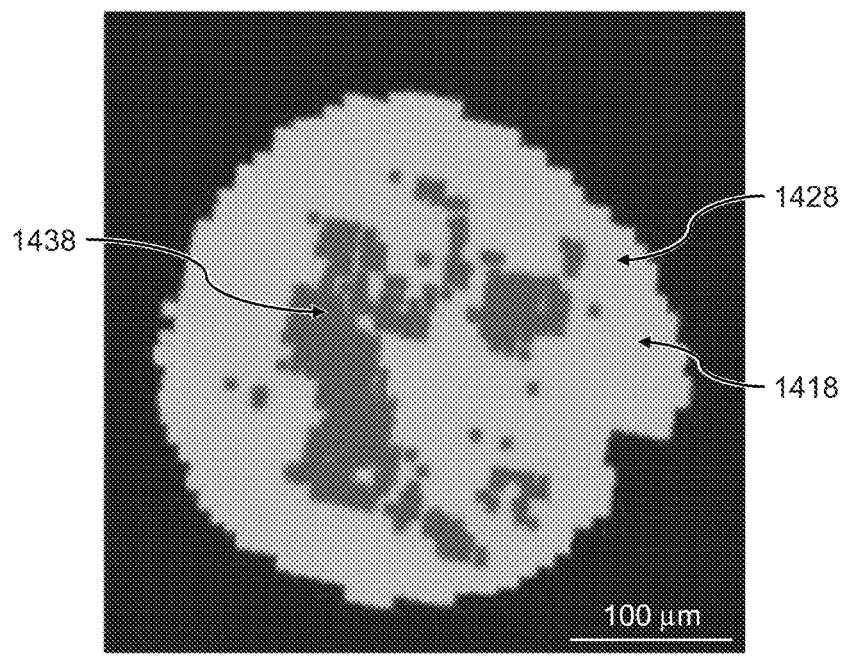
FIG. 14 is an imageJ analysis of thresholded mask regions of the non-uniform regions (colored red) of the pattern and the total area of the pattern (colored green), respectively.

In order to characterize this, an imageJ macro was created to measure the entire area of the lipid pattern and the non-uniform regions as shown in FIG. 14. The macro creates a mask and then dilates the pixels of the pattern to create a total area. Output 1418 is the total area in pixels and a picture, which is shown in FIG. 14 as green. The macro then repeats but first erodes the pixels to erase the uniform regions 1428, then dilates the same amount of times in order to show only non-uniform regions 1438, which in FIG. 14 is red. The inked PDMS stamp will eventually print numerous uniform lipid dot patterns while it is adequately inked.

Figure 15:
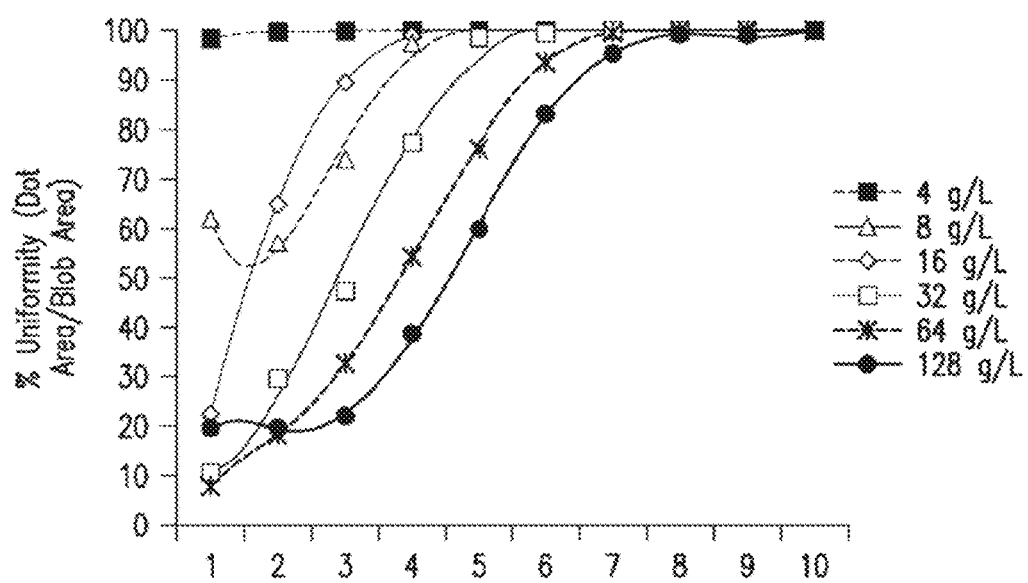
FIG. 15 is a graph showing the uniformity characterization obtained from the analytical technique shown in FIG. 13.

FIG. 15 is a graph showing the increase in uniformity as the number of successive prints increase. The data was obtained by the process shown in FIG. 15 for each print. Percent uniformity of the entire lipid pattern is defined as [1−(non-uniform regions/total area)]×100%.

Figure 16:
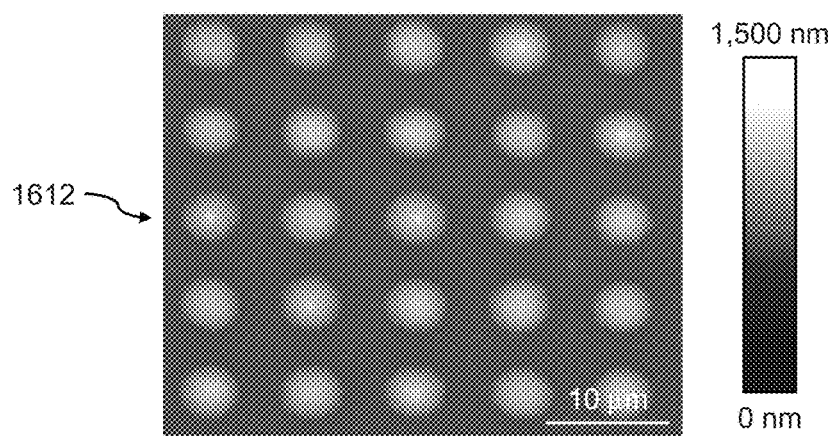
FIG. 16 is an image showing the AFM height profile of 25 lipid dots imaged on glass derived from a liposomal concentration of 16 g/L.

FIG. 16 shows another experiment where the same liposomal concentrations were again microarrayed and stamped onto glass substrate 1612. Each of the lipid patterns were imaged using AFM. A sample of 25 lipid dots from each pattern created from the different liposomal concentrations were imaged and analyzed to determine the height of each dot. FIG. 16 shows an example AFM image of the 16 g/L liposomal concentration.

Figure 17:
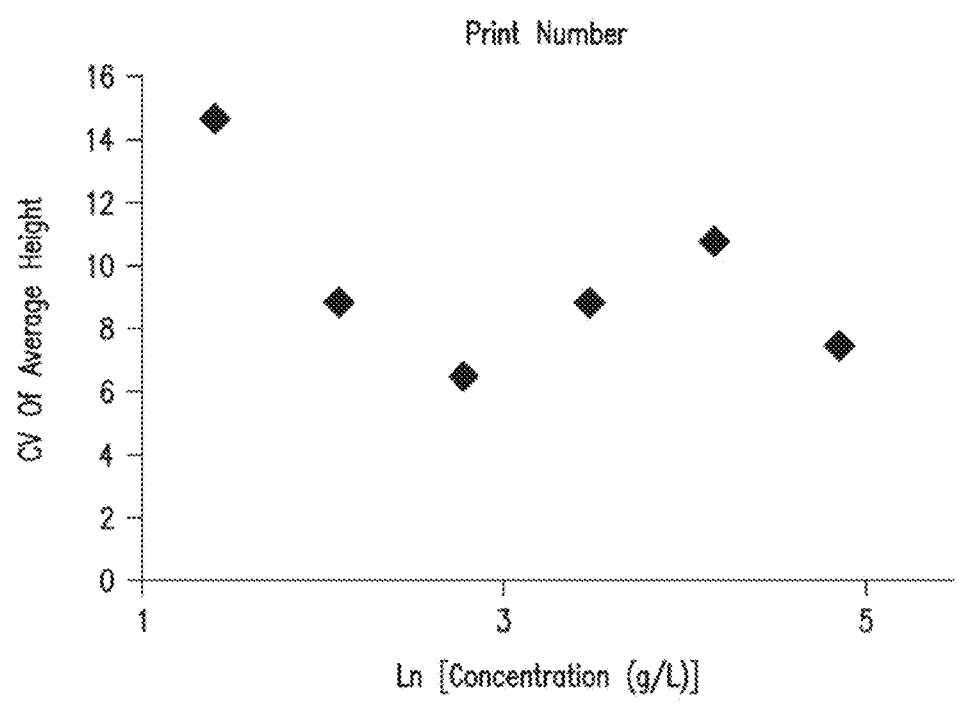
FIG. 17 is a graph showing the average height of lipid dots derived from the series of AFM measurements on glass as shown in FIG. 16.
Figure 18:
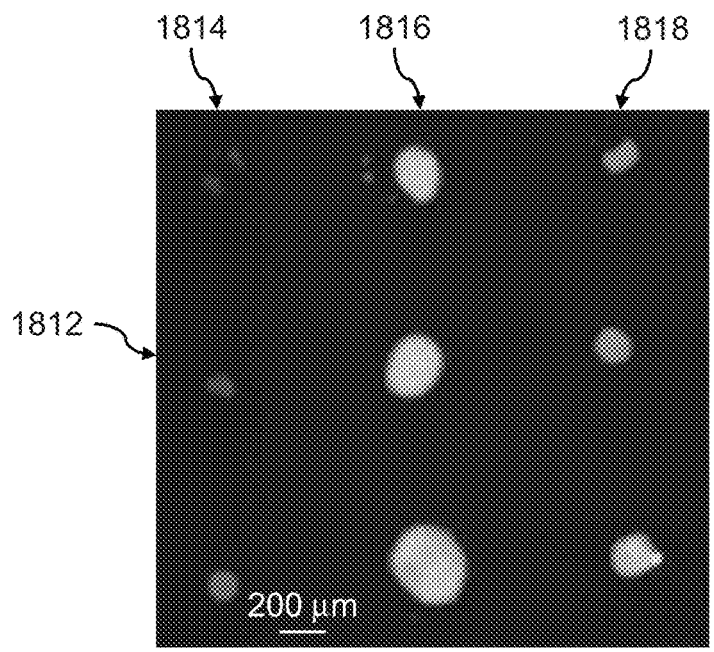
FIG. 18 is an image of a 3×3 ink pallet of DOTAP-doped with 1 Mol % Marina Blue-DHPE, Rhodamine-DOPE and Carboxyfluorescein-DOPE.

Using imageJ, round Regions of Interest were formed around each of the lipid dots and the average intensity was calculated. Using the AFM image height conversion, the average height of each of the 25 lipid dots were found. FIG. 17 shows the CV of the heights, such that CV=standard deviation of average height/mean average height×100% plotted with the concentration of each liposomal concentration from which the surface structures were derived.

Example 2

Figure 19:
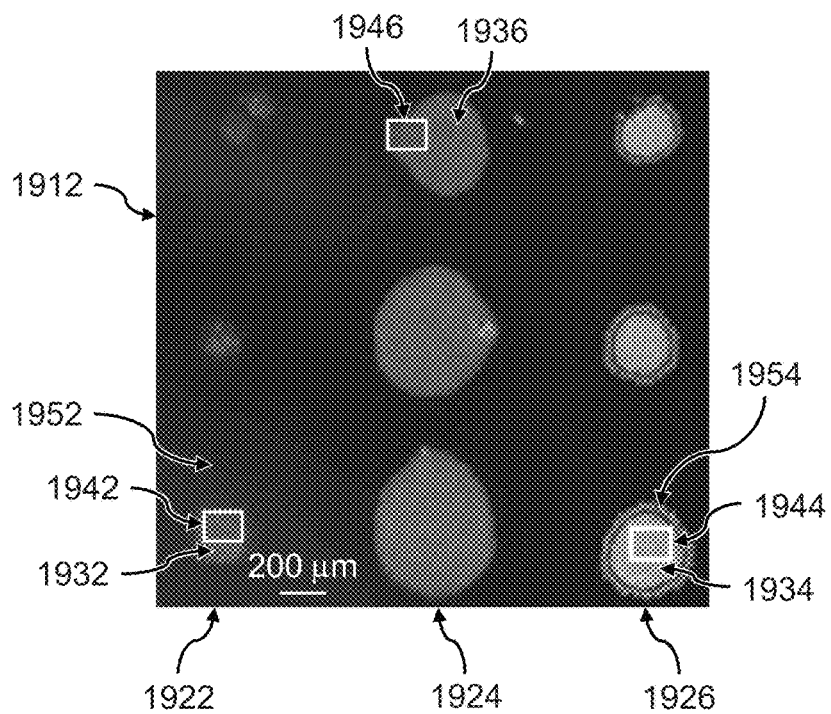
FIG. 19 is a 10× fluorescence stitch image of lipid dot patterns structured from the different lipid inks that were multilayer stamped onto a glass slide.
Figure 20:
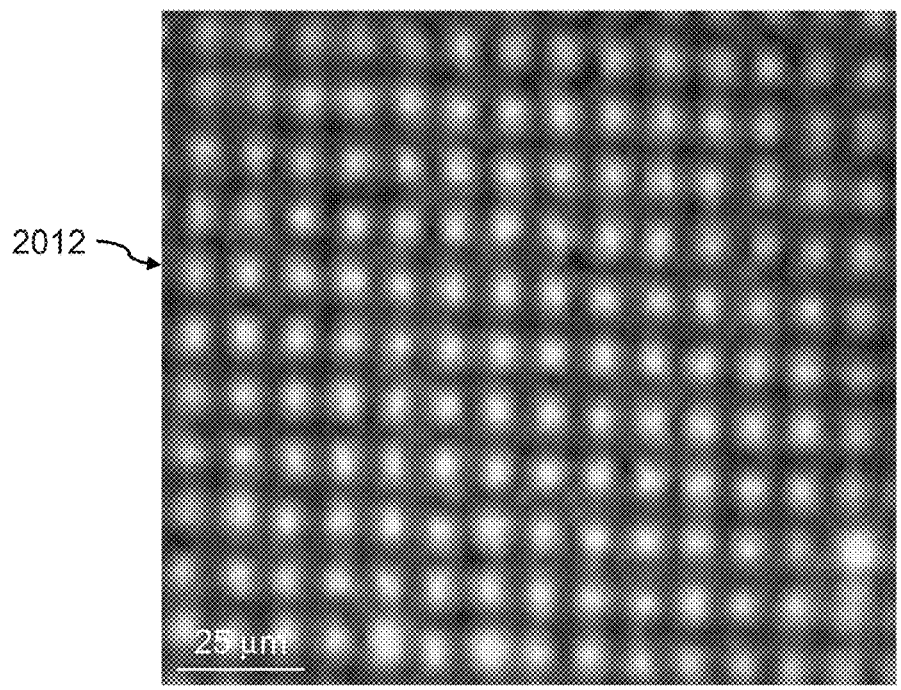
FIG. 20 is a digitally zoomed image of Marina Blue-DHPE doped patterns shown in FIG. 19.
Figure 21:
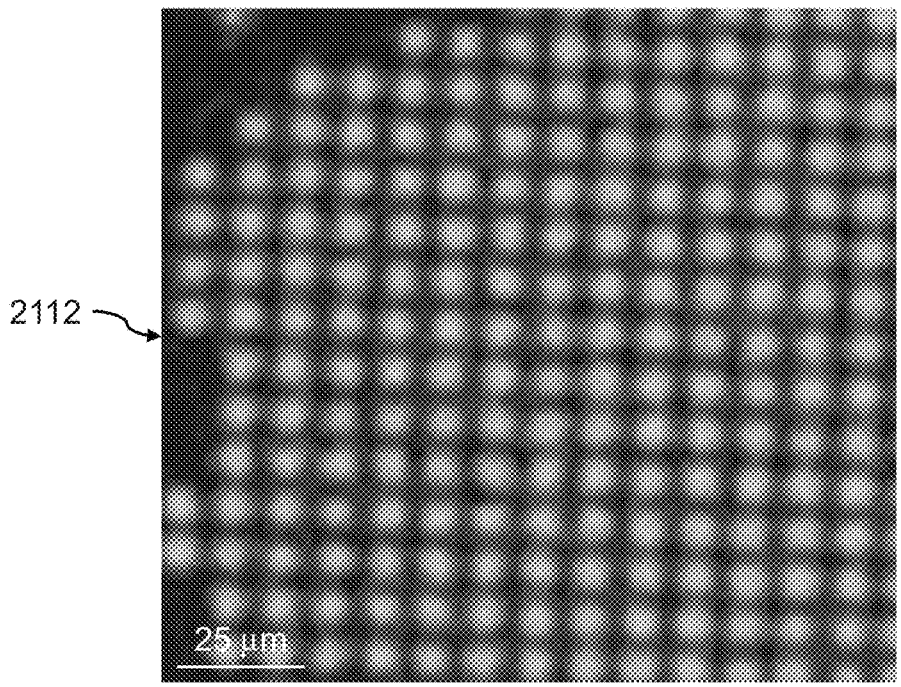
FIG. 21 is a digitally zoomed imaged of Rhodamine-PE doped patterns shown in FIG. 19.
Figure 22:
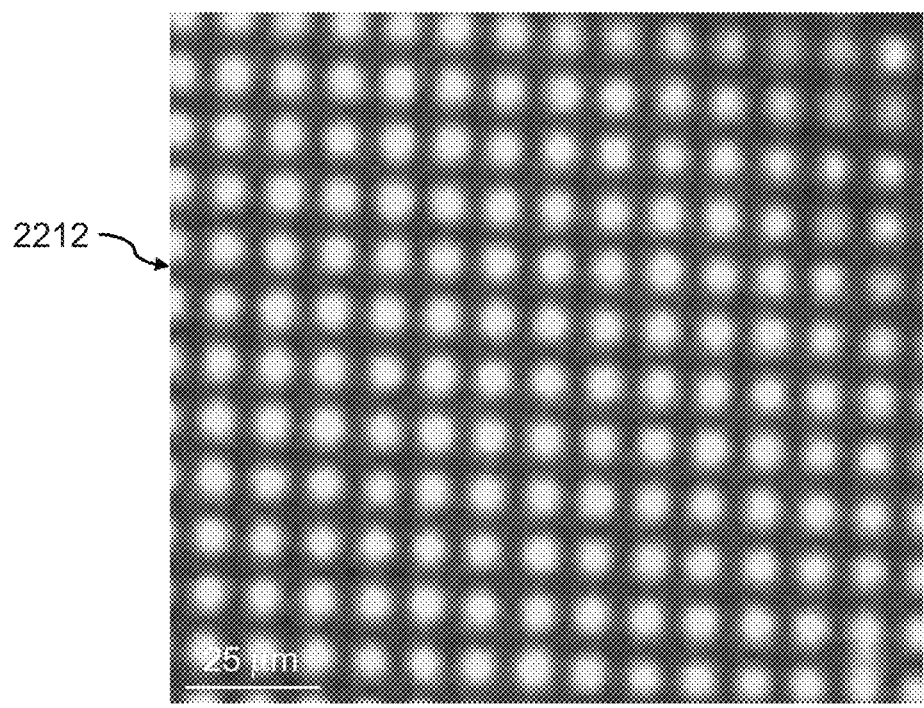
FIG. 22 is a digitally zoomed image of Carboxyfluorescein-PE doped patterns shown in FIG. 19.

FIGS. 18, 19, 20, 21 and 22 represent the multiplexing capabilities of a microarraying process in combination with multilayer stamping according to one embodiment of the present invention. The microarrayer is capable of writing multiple inks onto the same substrate, as shown in panel 1812 of FIG. 18. The three different fluorophores used in the test shown in FIG. 18 were Marina Blue-DHPE (a blue fluorophore), carboxyfluorescein-PE (a green fluorophore) and rhodamine-pe (a red fluorophore), which were used in columns 1814, 1816 and 1818, respectively. With the washing protocol used, there was no cross contamination observed in this sample. Panel 1912 of FIG. 19 shows the ability of multilayer stamping according to one embodiment of the present invention to faithfully produce lipid dot patterns of DOTAP doped with different fluorophores. The fluorophores used in the test in FIG. 19 were Marina Blue-DHPE (column 1922), carboxyfluorescein-PE (column 1924) and rhodamine-PE (column 1926). FIG. 19 shows lipid dot patterns 1932, 1934 and 1936 and white boxed regions 1942, 1944 and 1946. Halos 1952 and 1954 around the blue and green fluorophores, respectively, are spread cationic multilayers that result from the stamping process and subsequent exposure to environmental conditions. Panels 2012, 2112 and 2212 of FIGS. 20, 21 and 22, respectively, show digitally zoomed 4× fluorescence micrographs of the three different lipid dot patterns shown FIG. 19, i.e., lipid dot patterns 1932, 1934 and 1936, respectively. FIGS. 20, 21 and 22 show white boxed regions 1942, 1944 and 1946, respectively, of FIG. 19.

Example 3

Figure 23:
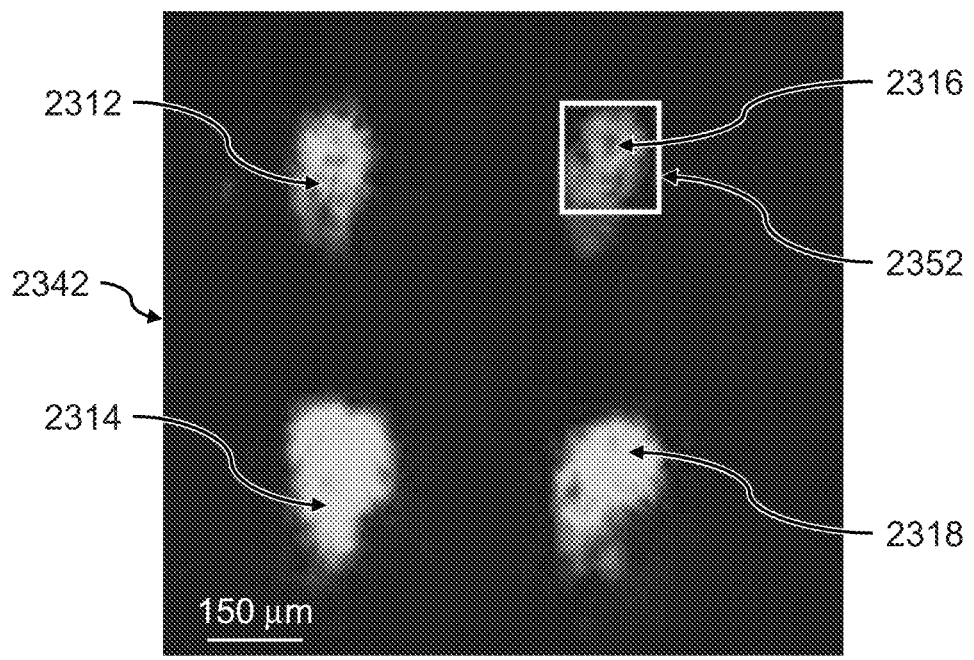
FIG. 23 is a 4×TRITC fluorescence micrograph of patterns of DOTAP multilayers printed onto glass using a 5 μm well stamp.
Figure 24:
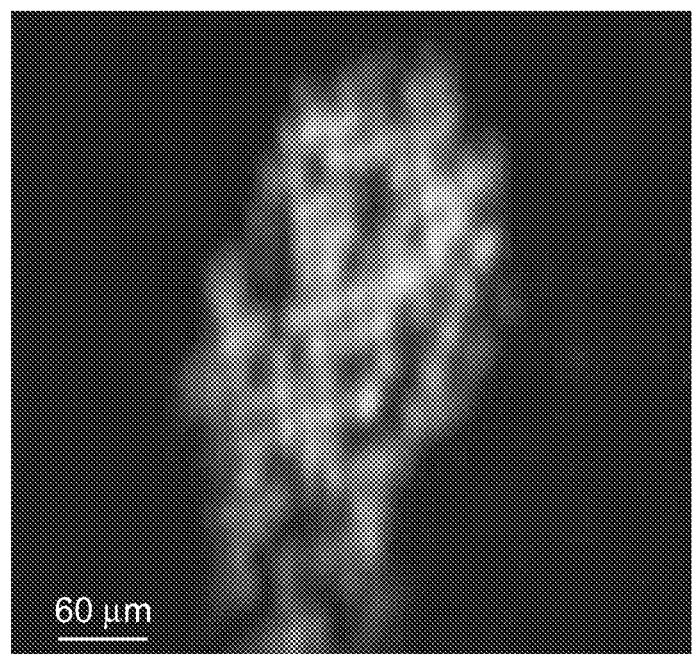
FIG. 24 is an image showing the digital zoom of spot in FIG. 23 indicated with the white square.
Figure 25:
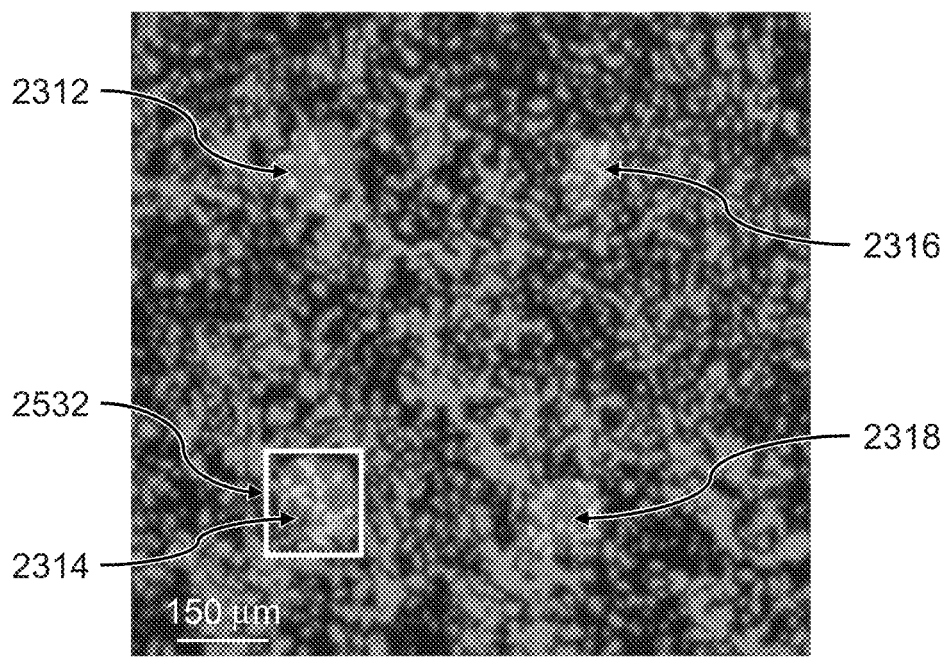
FIG. 25 is a 4× merged fluorescence micrograph of FITC and TRITC images of spots in FIG. 23.
Figure 26:
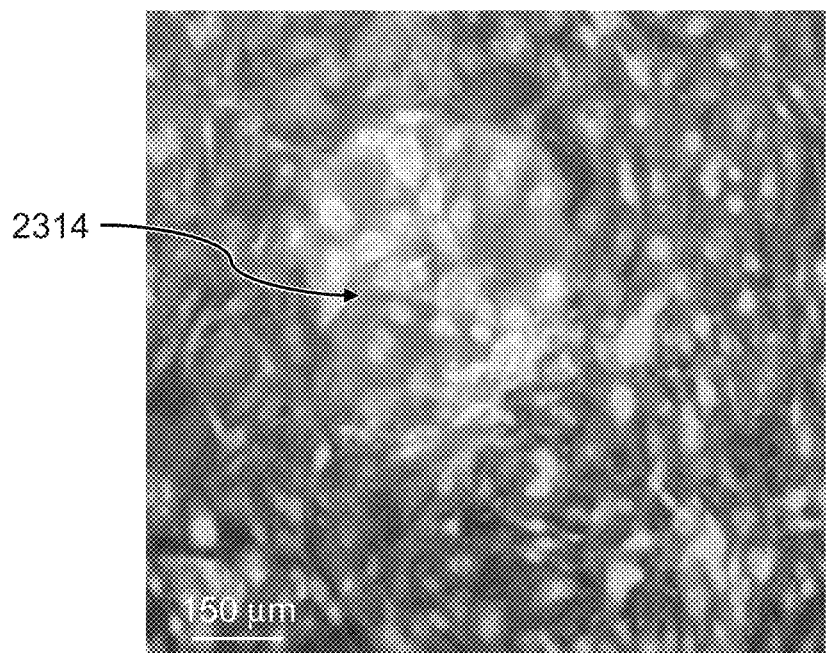
FIG. 26 is a 10× merged fluorescence micrograph of FITC and TRITC images of a spot in a region indicated by a white box in FIG. 25.
Figure 27:
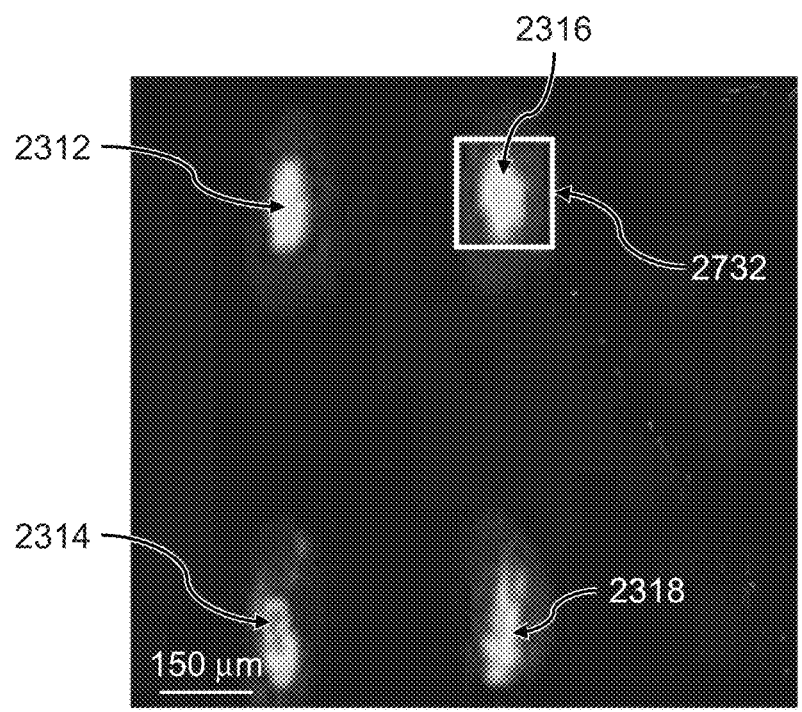
FIG. 27 is a 4×TRITC fluorescence micrograph of patterns of DOTAP multilayers printed directly onto glass using a microarrayer.
Figure 28:
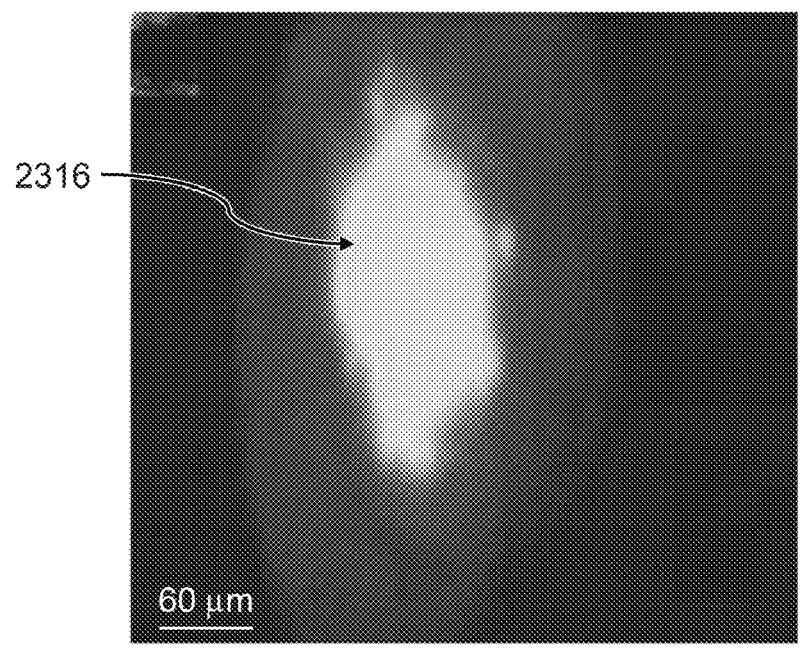
FIG. 28 is an image showing the digital zoom of the spot in indicated with the white square in FIG. 26.
Figure 29:
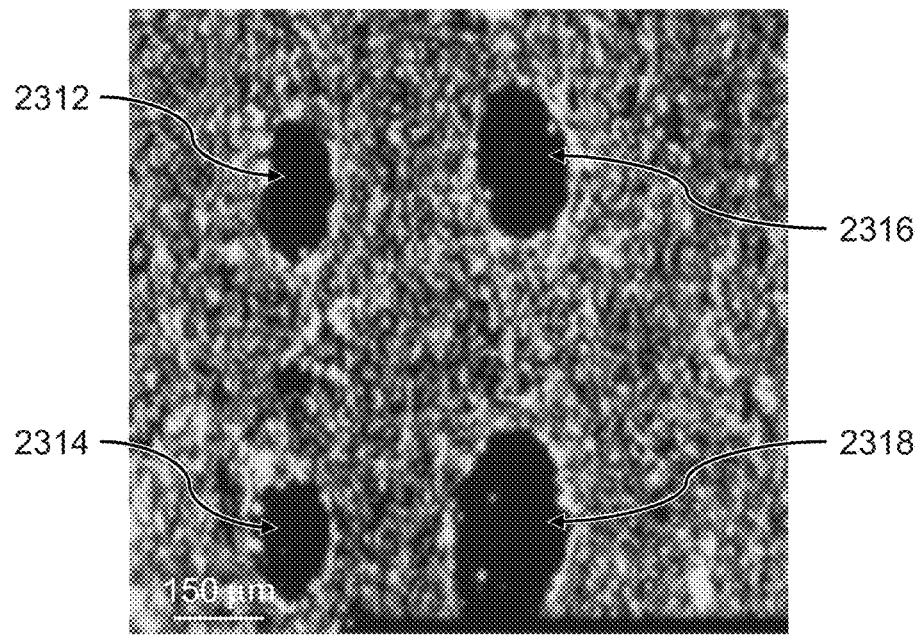
FIG. 29 is a 4× merged fluorescence micrograph of FITC and TRITC images of spots in FIG. 23.
Figure 30:
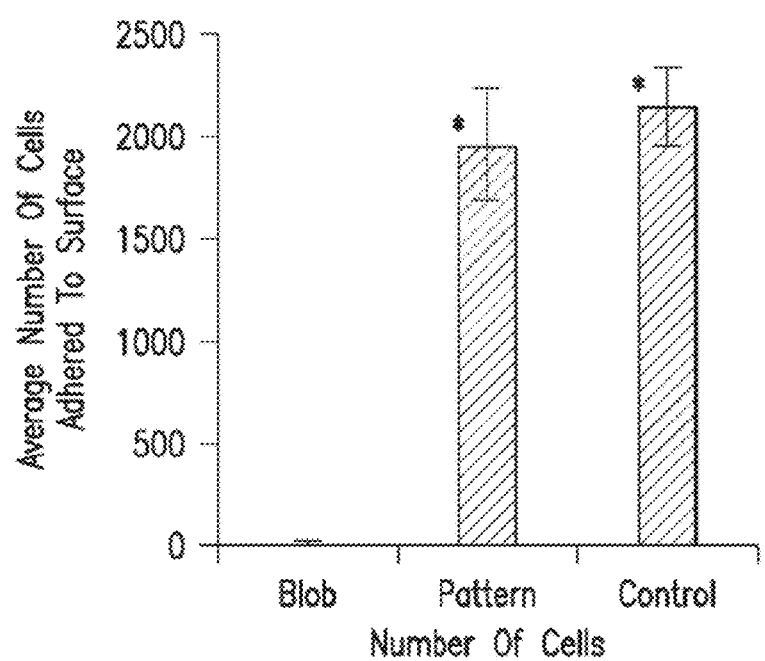
FIG. 30 is a graph showing that cells binding to both the patterned area and the non-patterned area efficiently but not to the areas with the blobs.

FIGS. 23, 24, 25, 26, 27, 28, 29 and 30 show how cells bind to and grow on patterned areas but not on the contiguous lipid multilayers (blobs). FIG. 23 is a 4×TRITC fluorescence micrograph of patterns of DOTAP stamped spots 2312, 2314, 2316 and 2318 printed onto glass 2342 using a 5 μm well stamp. FIG. 23 includes a region 2352 enclosed in white box. FIG. 24 presents the digital zoom of region 2352 of FIG. 23 showing greater detail of stamped spot 2316. FIG. 25 is 4× merged fluorescence micrograph of FITC and TRITC images of stamped spots 2312, 2314, 2316 and 2318. HeLa cells seeded on patterns adhere and grow. FIG. 25 includes a region 2532 enclosed in a white box. FIG. 26 is a 10× merged fluorescence micrograph of FITC and TRITC images of region 2532 of FIG. 25 show greater detail of stamped spot 2314. FIG. 27 is a 4×TRITC fluorescence micrograph of patterns of DOTAP stamped spots 2312, 2314, 2316 and 2318 printed directly onto glass using a microarrayer. FIG. 27 includes a region 2732 enclosed in a white box. FIG. 28 is the digital zoom of region 2732 of FIG. 27 that shows greater details of spot 2316. FIG. 29 is a 4× merged fluorescence micrograph of FITC and TRITC images of spots 2312, 2314, 2316, and 2318 that HeLa cells seeded on. Blobs break off into the media and cells do not grow at areas where blobs were. FIG. 30 is a graph showing that cells binding to both the patterned area and the non-patterned area efficiently but not to the areas with the blobs. All living cells labeled with green Syto 9 cell stain. Lipids doped with rhodamine-PE. Cell numbers obtained from counting all the cells on 80 patterned areas in each well.

The lipids without drugs were printed on glass and the heights measured with an AFM as shown in FIGS. 18, 19, 20, 21 and 22. The printed patterns are spaced out enough to allow for cellular adhesions to form before the lipids spread. Large blobs without these spaces do not allow cells to grow on them and allow for lipid and drug uptake (FIGS. 23, 24, 25, 26, 27, 28, 29 and 30). NIH 3T3 cells plated on the patterns adhered similarly to the control surface without any lipids.

Example 4

Figure 31:
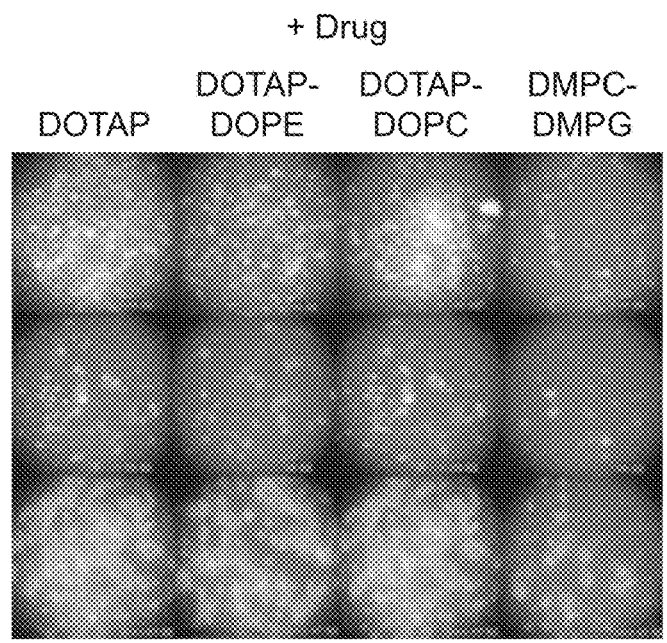
FIG. 31 is an image of cells cultured on the printed liposomes without the drug (docetaxel) and cultured for 79 hrs.
Figure 32:
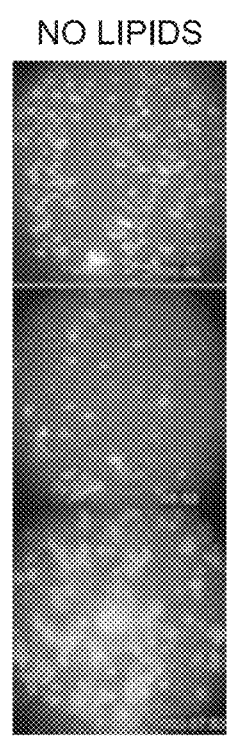
FIG. 32 is an image of cells on an area away from the patterns but in the same dish used as a negative control.

The effect of liposomal composition on the efficacy of docetaxel on HeLa cells is shown in FIGS. 31, 32, 33, 34 and 35. In FIG. 31, cells are cultured on the printed liposomes without the drug (docetaxel) and cultured for 79 hours. FIG. 32 shows cells on an area away from the patterns but in the same dish used as a negative control.

Figure 33:
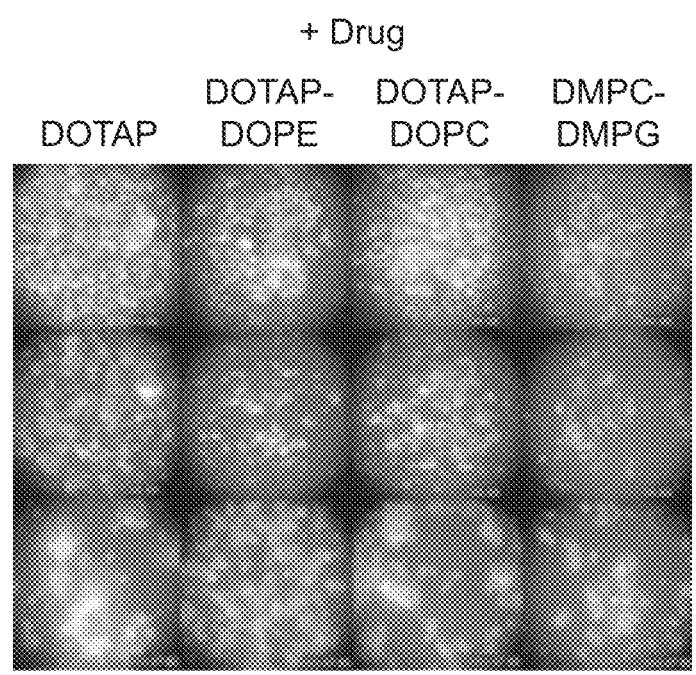
FIG. 33 is an image of cells cultured on the printed liposomes with the drug (docetaxel)) encapsulated and culture for 79 hours.
Figure 34:
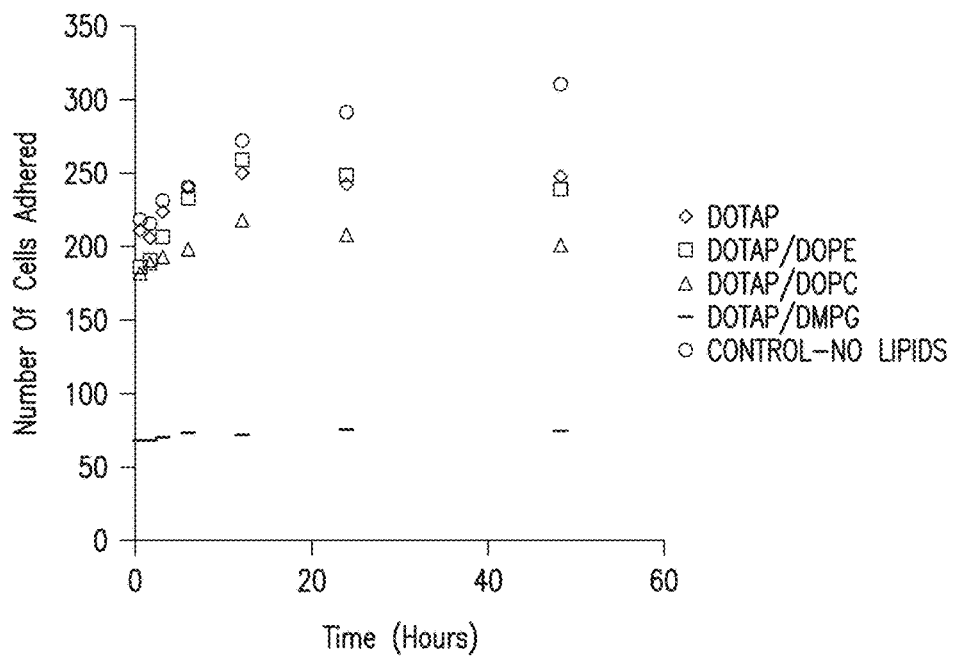
FIG. 34 is a graph showing the adhesion of cells on control lipids (without drug) over 79 hrs.
Figure 35:
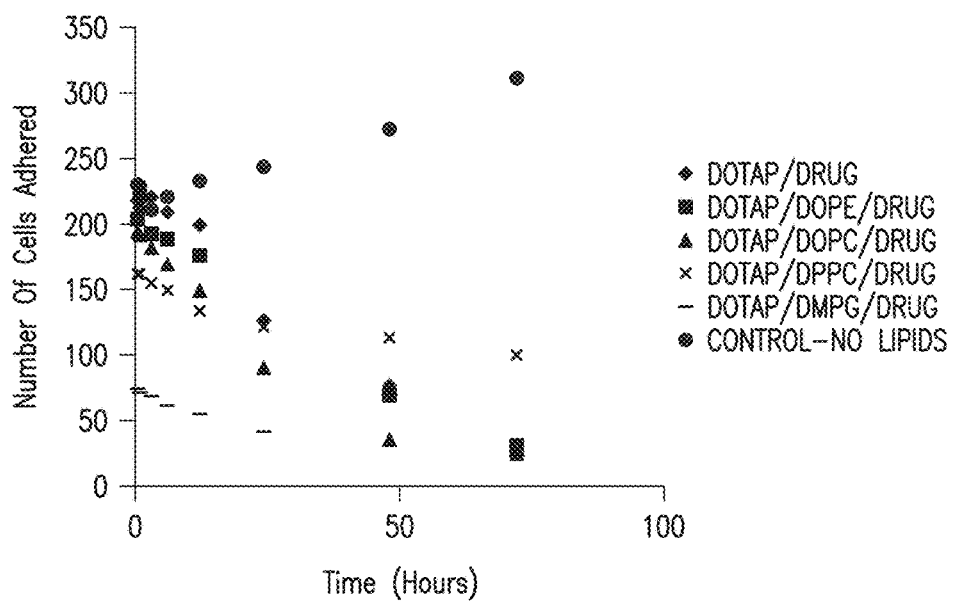
FIG. 35 is a graph showing the adhesion of cells on drug encapsulated lipids over 79 hours as a test for liposomal dependent efficacy of the drug (docetaxel).

FIG. 33 shows drug encapsulated in the first row of pictures in FIGS. 31 and 32 with stamped timepoint 0 represent the cells after 30 minutes in culture during which the microscope was being equilibrated. FIG. 34 is a graph showing adhesion of cells on control lipids (without drug) over 79 hours. FIG. 35 is a graph showing adhesion of cells on drug encapsulated lipids over 79 hours as a test for liposomal dependent efficacy of the drug (docetaxel).

Immersion of the samples under water was done under a nitrogen atmosphere as the only alternative short of in situ printing under water.[38] This was done without destruction of the liposome carrier array for the drugs.

Example 5

Figure 36:
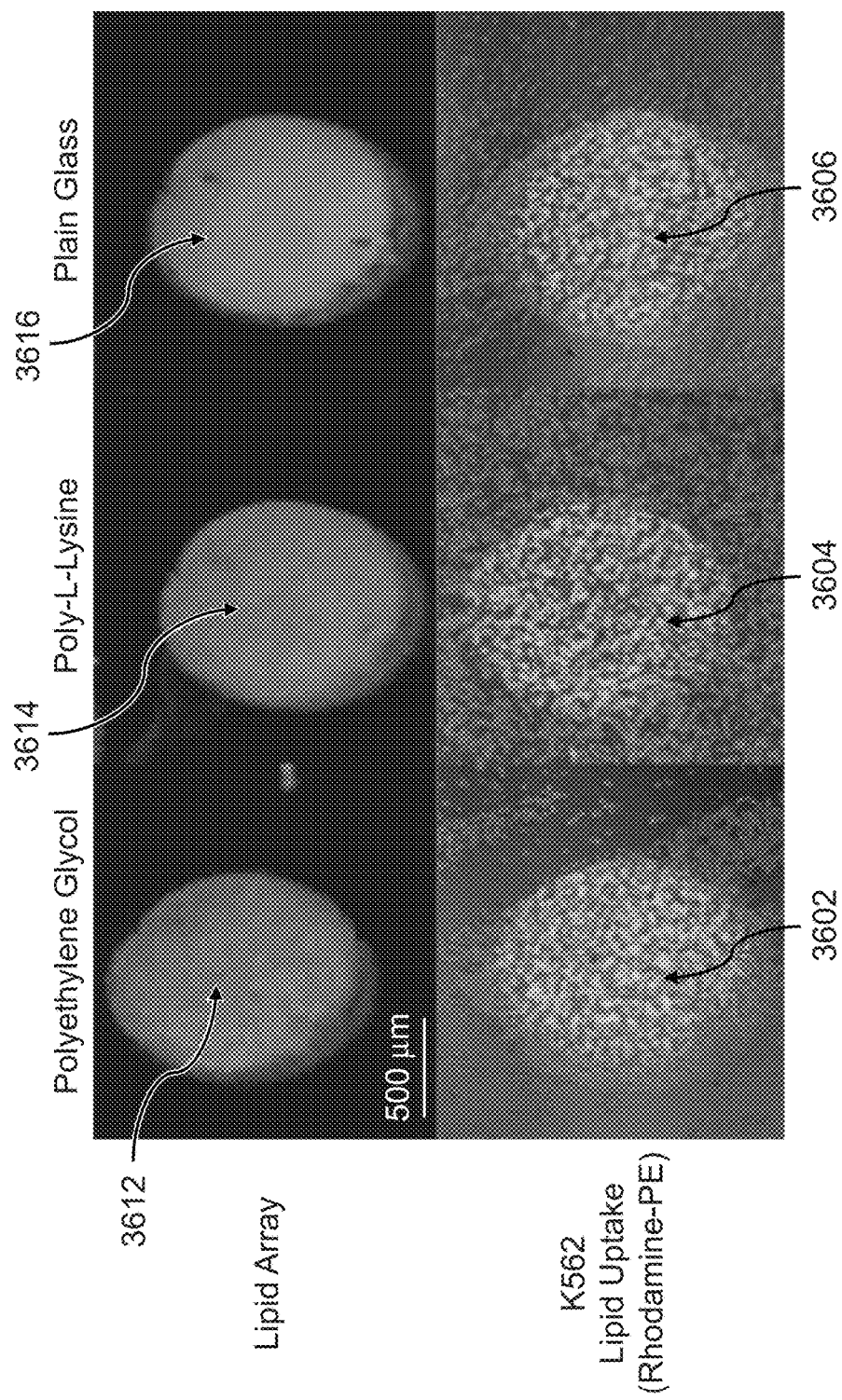
FIG. 36 is a merged image showing the adhesion of bright field and rhodamine of K562 lipid array on (A) Poly Ethylene Glycol, (B) Poly-L Lysine and (C) plain glass.

Cationic liposomes printed using the technique above can be used to localize suspension cells in order to screen them in a high throughput manner. The myeloid leukemic cell model K562 are suspension cells, and so far liposome microarray technology has only been demonstrated on adherent cells. However, FIG. 36 shows that K562 suspension cells can adhere to Poly Ethylene Glycol (PEG) (see image 3602), Poly-L-Lysine (PLL) (see image 3604), and plain glass liposome microarrays in culture (see image 3606). When seeded at 0.5 million cells/mL (250,000 cells/22 mm$^2$) K562 cells were found to adhere to all three substrates evaluated to differing degrees: plain glass, Poly-ethylene Glycol (PEG), and Poly-L-Lysine (PLL). Images 3612, 3614 and 3616 show the liposome microarrays on which the K562 cells of images 3602, 3604 and 3606, respectively, were deposited.

Example 6

Figure 37:
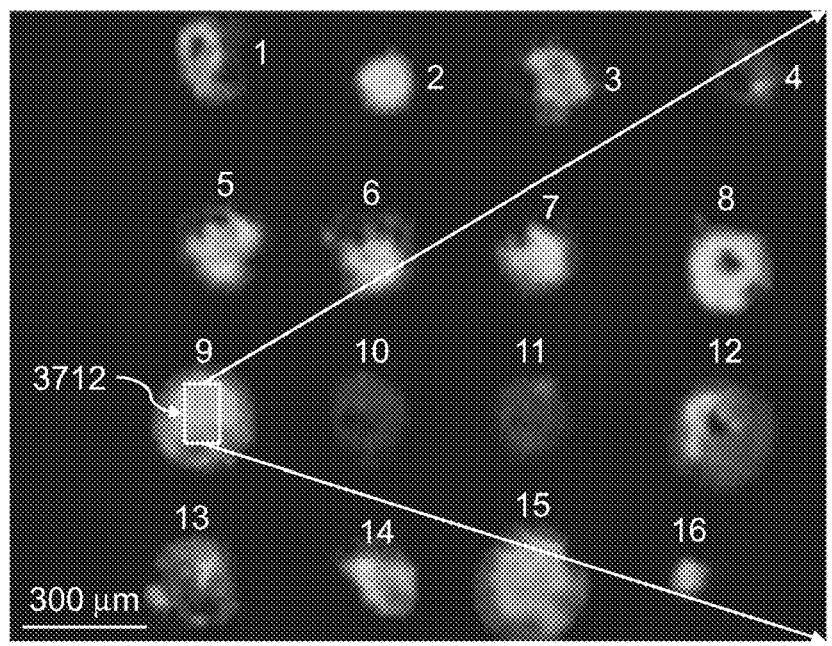
FIG. 37 is a fluorescence micrograph of 4*4 array of lipid formulations on glass in air.
Figure 38:
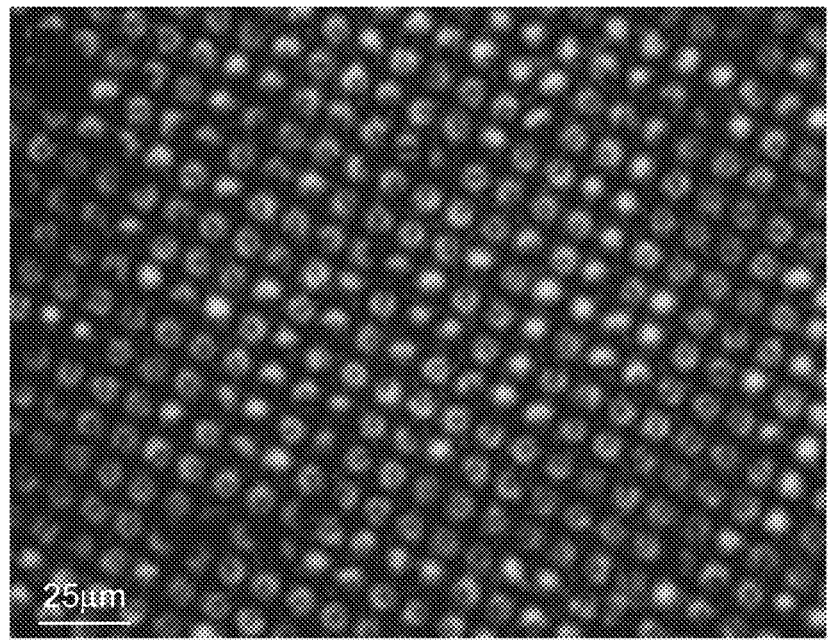
FIG. 38 is a 40× image of the region indicated by a white box in FIG. 32.
Figure 39:
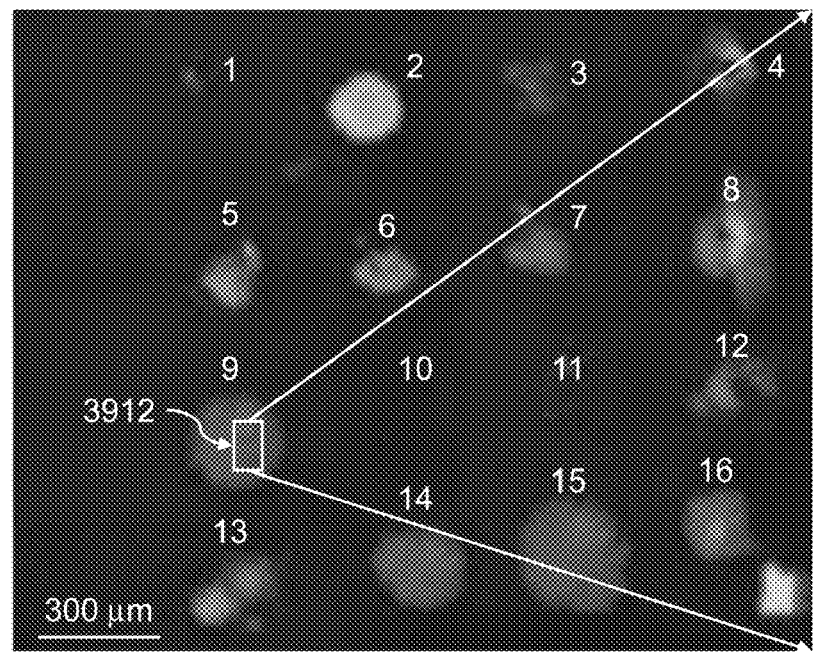
FIG. 39 is an image of arrays stamped onto glass slide and immersed underwater in a nitrogen atmosphere.
Figure 40:
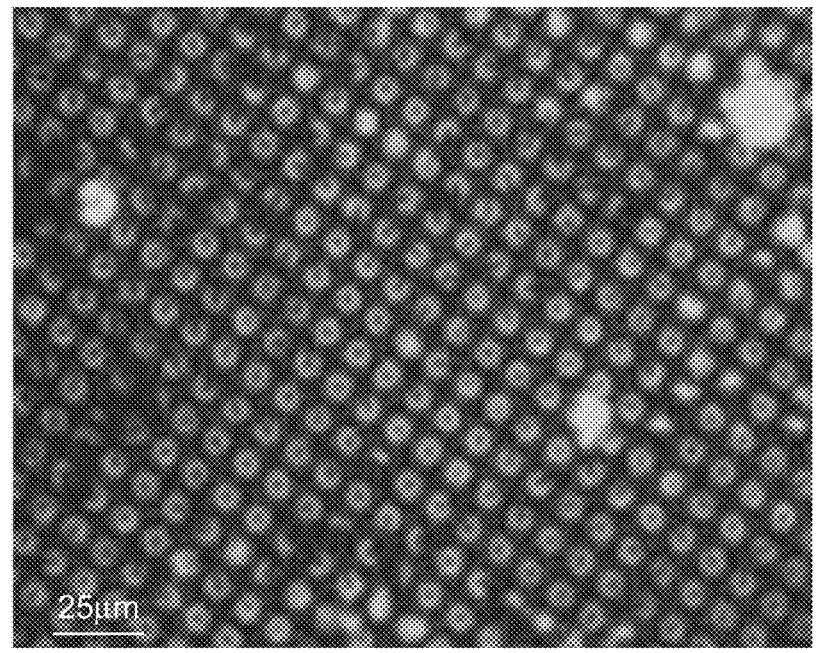
FIG. 40 is a 40× image of the region indicated by a white box in FIG. 39.
Figure 41:
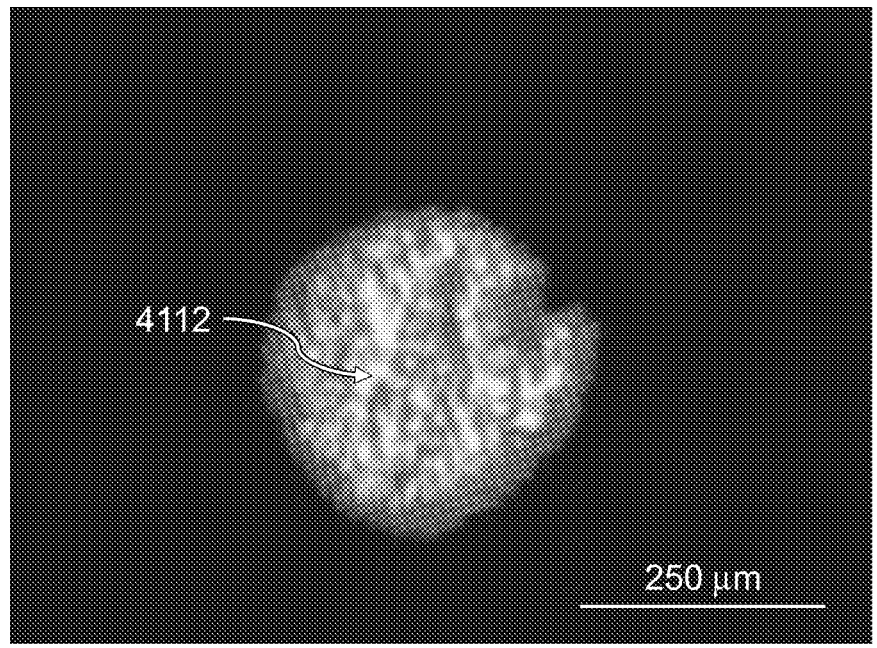
FIG. 41 is an image of spots patterned using scalable lipid multilayer stamping and printed the second time from the same stamp.
Figure 42:
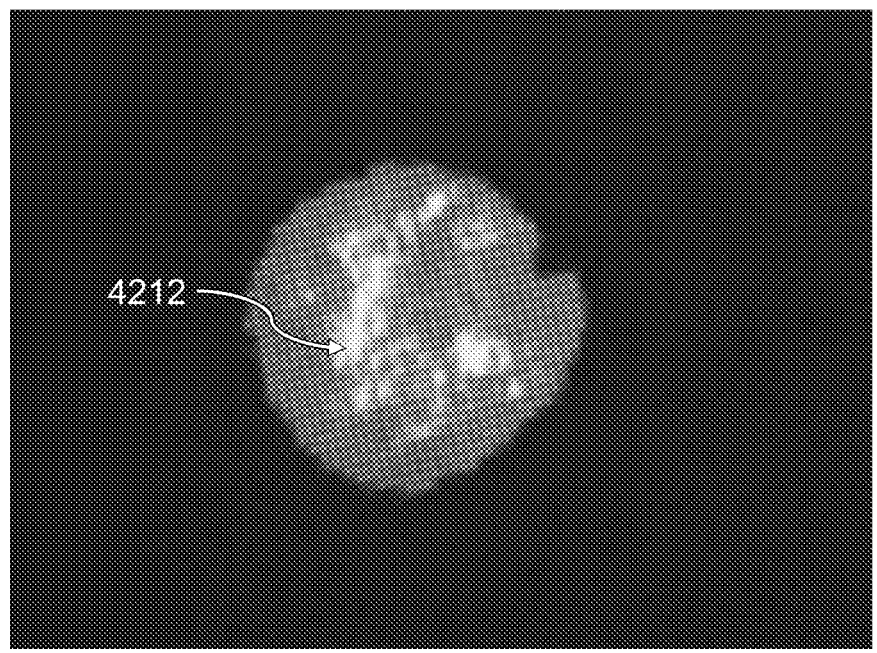
FIG. 42 is an image of spots patterned using scalable lipid multilayer stamping and printed the fourth time from the same stamp.
Figure 43:
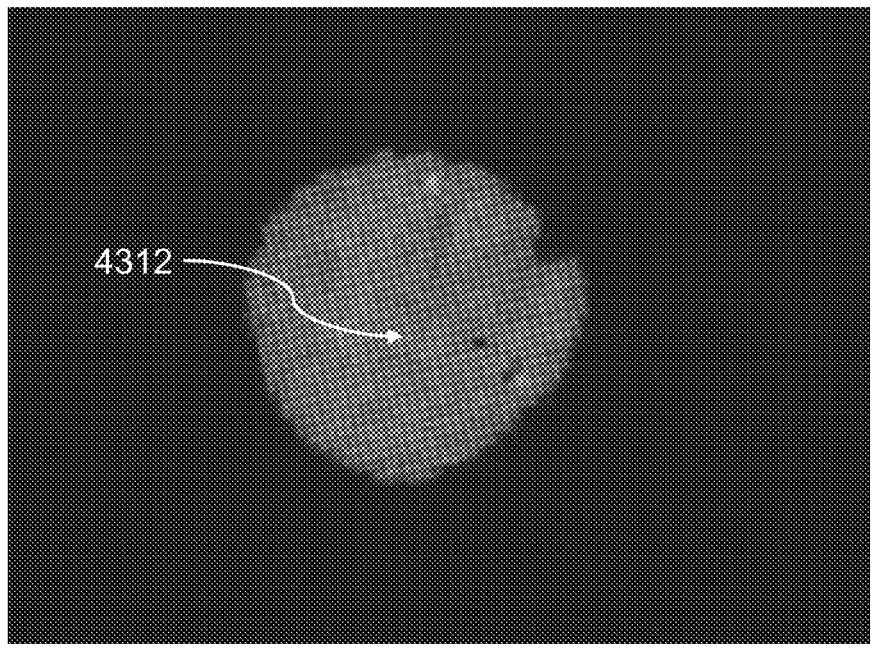
FIG. 43 is an image of spots patterned using scalable lipid multilayer stamping and printed the sixth time from the same stamp.
Figure 44:
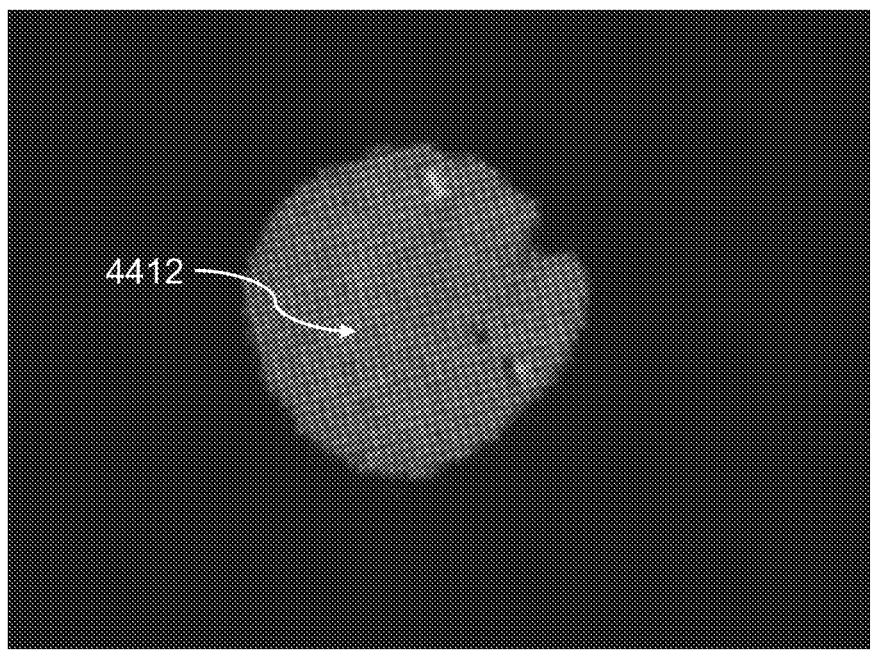
FIG. 44 is an image of spots patterned using scalable lipid multilayer stamping and printed the eighth time from the same stamp.

Patterns are immmersible under water in a nitrogen atmosphere, as depicted in FIGS. 37, 38, 39 and 40. FIG. 37 is a fluorescence micrograph of 4×4 array of lipid formulations 1 through 16 on glass in air. Each spot is numbered, and the compositions are: [1] DOTAP only, [2] DOTAP+Valinomycin (1:1), [3] DOTAP+Valinomycin (2:1), [4] DOTAP+Valinomycin (4:1), [5]—DOTAP+Valinomycin (8:1), [6] DOTAP/DOPE (30:70)+Valinomycin (1:1), [7] DOTAP/DOPE (30:70)+Valinomycin (2:1), [8] DOTAP/DOPE (30:70)+Valinomycin (4:1), [9] DOTAP/DOPE (30:70)+Valinomycin (8:1), [10] DOTAP/Cholesterol (20 mol %)+Valinomycin (1:1), [11] DOTAP/Cholesterol (20 mol %)+Valinomycin (2:1), [12] DOTAP/Cholesterol (20 mol %)+Valinomycin (4:1), [13] DOTAP/Cholesterol (20 mol %)+Valinomycin (8:1), [14] DOTAP/DOPE (30:70)/Cholesterol (20 mol %)+Valinomycin (1:1), [15] DOTAP/DOPE (30:70)/Cholesterol (20 mol %)+Valinomycin (2:1), [16] DOTAP/DOPE (30:70). FIG. 37 includes a region 3712 enclosed in a white box. FIG. 38 is a 40× image of region 3712 of FIG. 37. FIG. 39 shows arrays 1 through 16 stamped onto glass slide and immersed under water in a nitrogen atmosphere. FIG. 39 includes a region 3912 enclosed in a white box. FIG. 40 is a 40× image of region 3912 of FIG. 39.

Example 7

Figure 45:
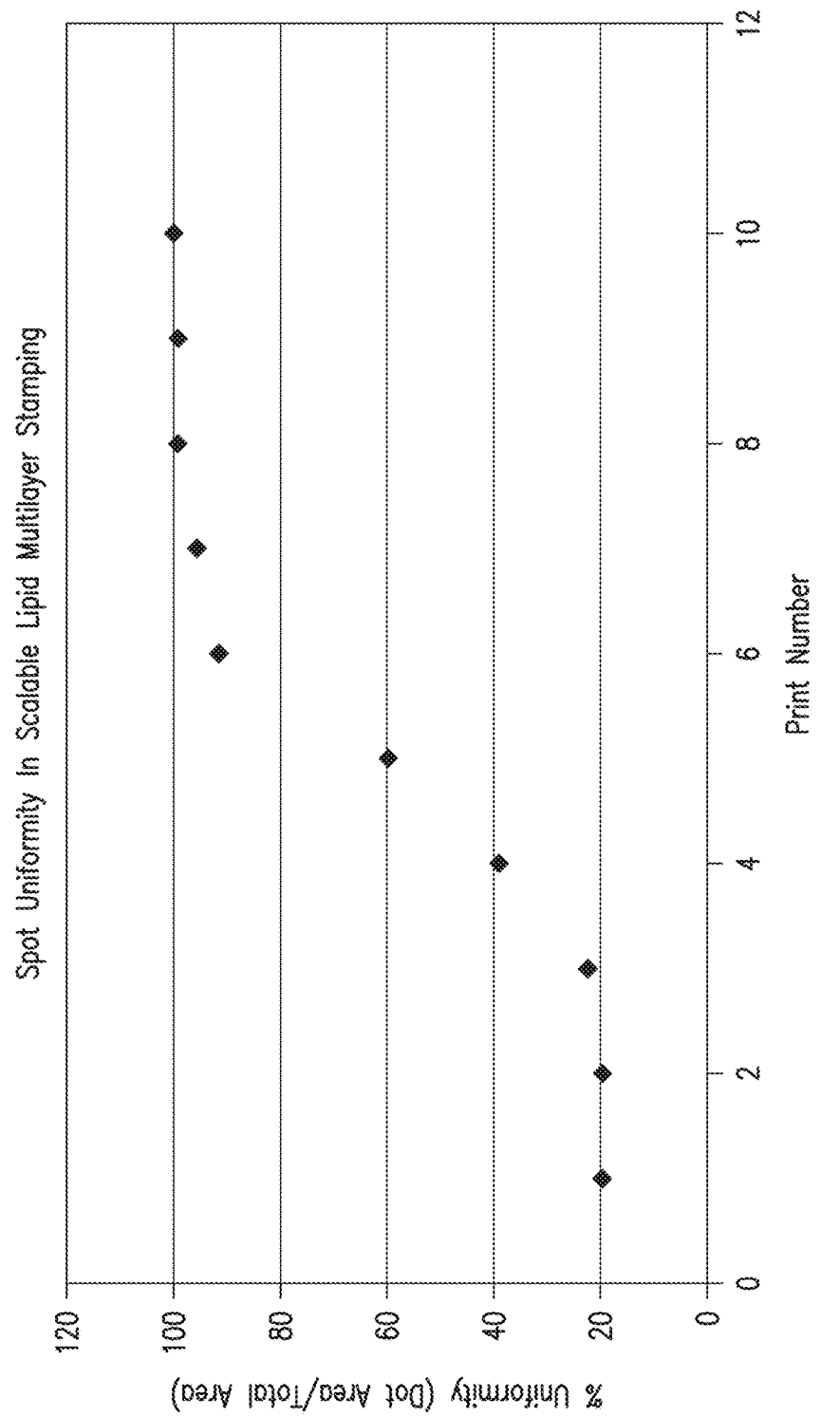
FIG. 45 is a graph showing spot uniformity in scalable lipid multilayer stamping.

FIGS. 41, 42, 43 and 44 are images of spots of print number 2 (spot 4112), 4 (spot 4212), 6 (spot 4312) and 8 (spot 4412) patterned using scalable lipid multilayer stamping, and printed several times from the same stamp. Spots become more uniform as excess ink is removed, as shown in the graph in FIG. 45.

Example 8

Figure 46:
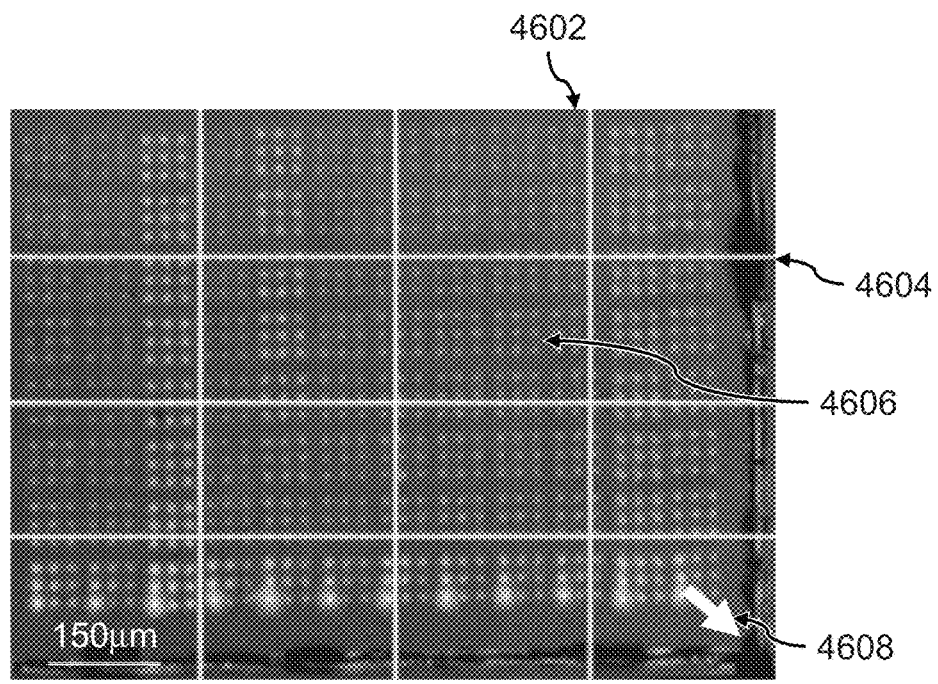
FIG. 46 is a merged image of phase contrast and fluorescent images of a rhodamine-labeled phospholipid DPN pattern before cell culture for a sample.
Figure 47:
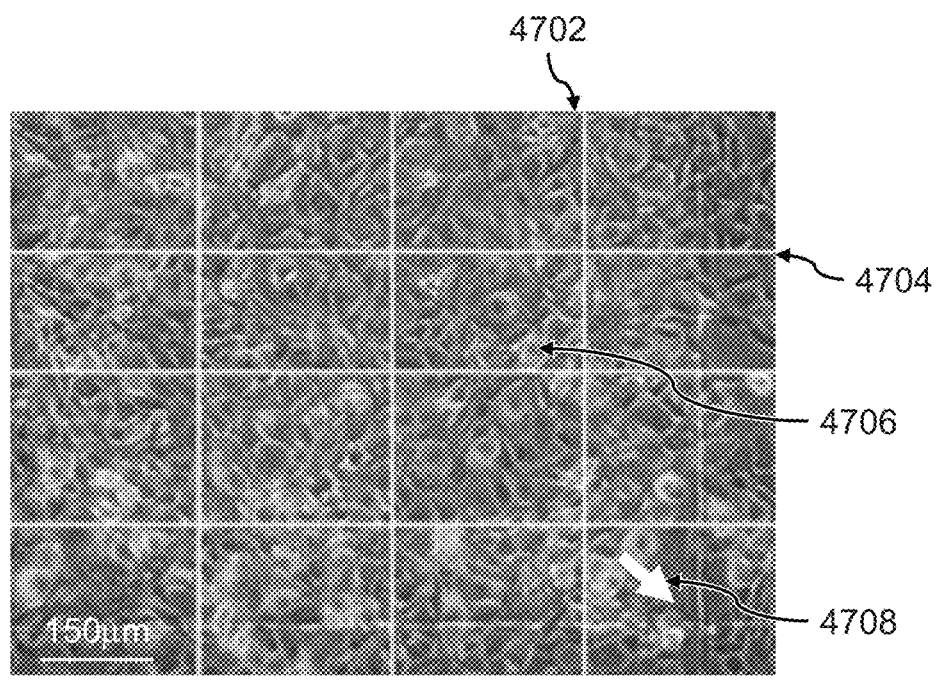
FIG. 47 is an image of cells after incubation over the pattern in FIG. 46 for 18 hours for the sample of FIG. 46.
Figure 48:
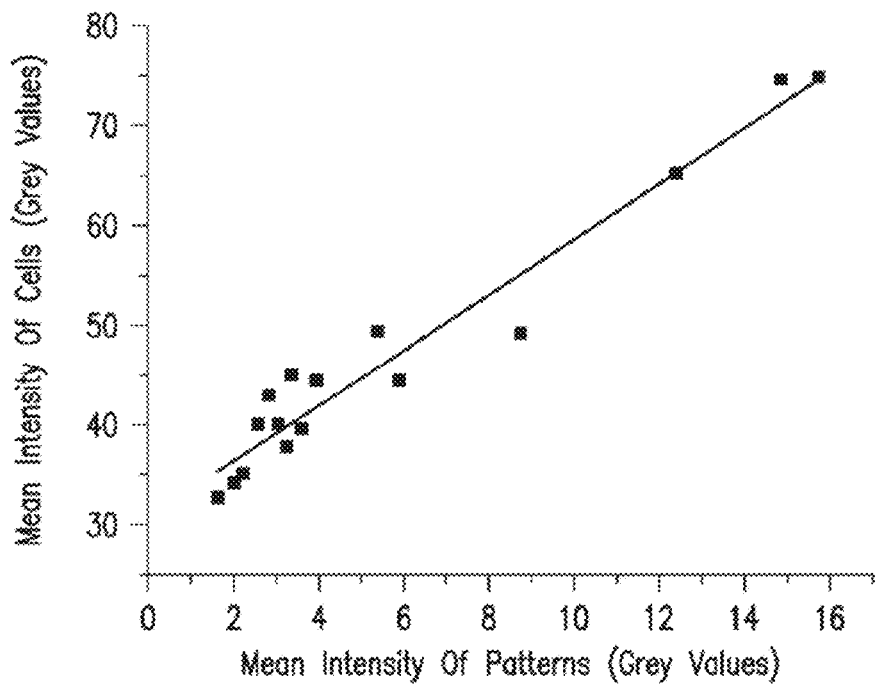
FIG. 48 is a graph showing an analysis of the correlation of intensity of spots with the average intensity of the cells for the sample of FIG. 46.
Figure 49:
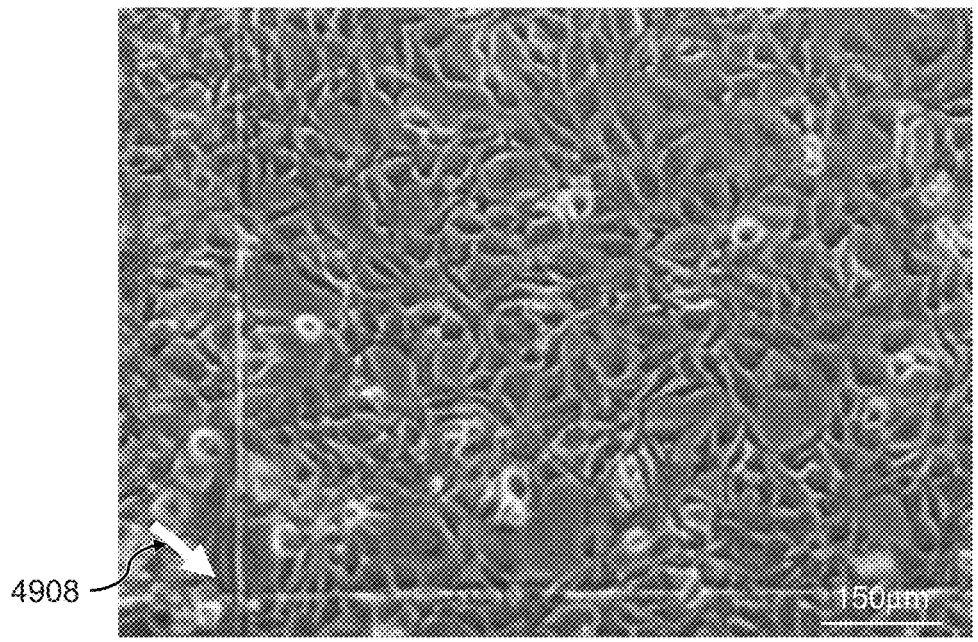
FIG. 49 is an imaging showing cells residing in a region immediately to the right of the region shown FIG. 47.

To demonstrate and quantify lipid uptake by the cells, NIH 3T3 cells are cultured over a rhodamine-doped lipid multilayer pattern for 24 hours. FIGS. 46, 47, 48 and 49 show the uptake of DOPE-rhodamine-labeled DOTAP by NIH 3T3 cells. FIGS. 46, 47 and 49 are all images from the same sample. FIG. 46 is a merged image of phase contrast and fluorescent images of a rhodamine-labeled phospholipid DPN pattern (array) before cell culture. FIG. 47 is an image of cells after incubation over the pattern in FIG. 46 for 18 hours. Fluorescence intensity is used as the indicator of the amount of lipid taken up by the cells. A higher fluorescence in cells indicates higher uptake of lipids. Grid lines 4602 and 4604 in FIG. 46 divide the image of FIG. 46 into equal areas 4606. Also shown in FIG. 46 is an arrow 4608. Grid lines 4702 and 4704 in FIG. 47 divide the images of FIG. 47 into equal areas 4706. Also shown in FIG. 47 is an arrow 4708. Cells were analyzed and compared for fluorescence intensity before and after cell incubation on the patterns. This division provided the highest correlation of the fluorescent intensities of the patterns with those of the cells, suggesting that this area is the average distance the cells migrated during the experiment. FIG. 48 is a graph showing an analysis of the correlation of intensity of dots with the average intensity of the cells. Images are divided into equal areas 4606 of FIG. 46 and equal areas of FIG. 47 for determination of the localization of the cells to their sources of lipids. The linearity of this relation indicates the possibility of obtaining dose-response curves from a single area of an array. The cells over the dots with high fluorescence intensity took up the most lipids and showed the highest intensity. FIG. 49 shows that cells residing in a region immediately to the right of the region shown in FIG. 47 do not fluoresce. Also shown in FIG. 49 is an arrow 4908. The contrast of images has been adjusted in the look-up tables of the NIKON NIS software for viewing purposes only. Arrows 4608, 4708 and 4908 point to common alignment marks that are scratched on the glass coverslip for the sample.

Example 9

FIG. 49 shows an area directly next to that shown in of FIG. 47, indicating that cells next to the spot do not take up lipids.

Figure 50:
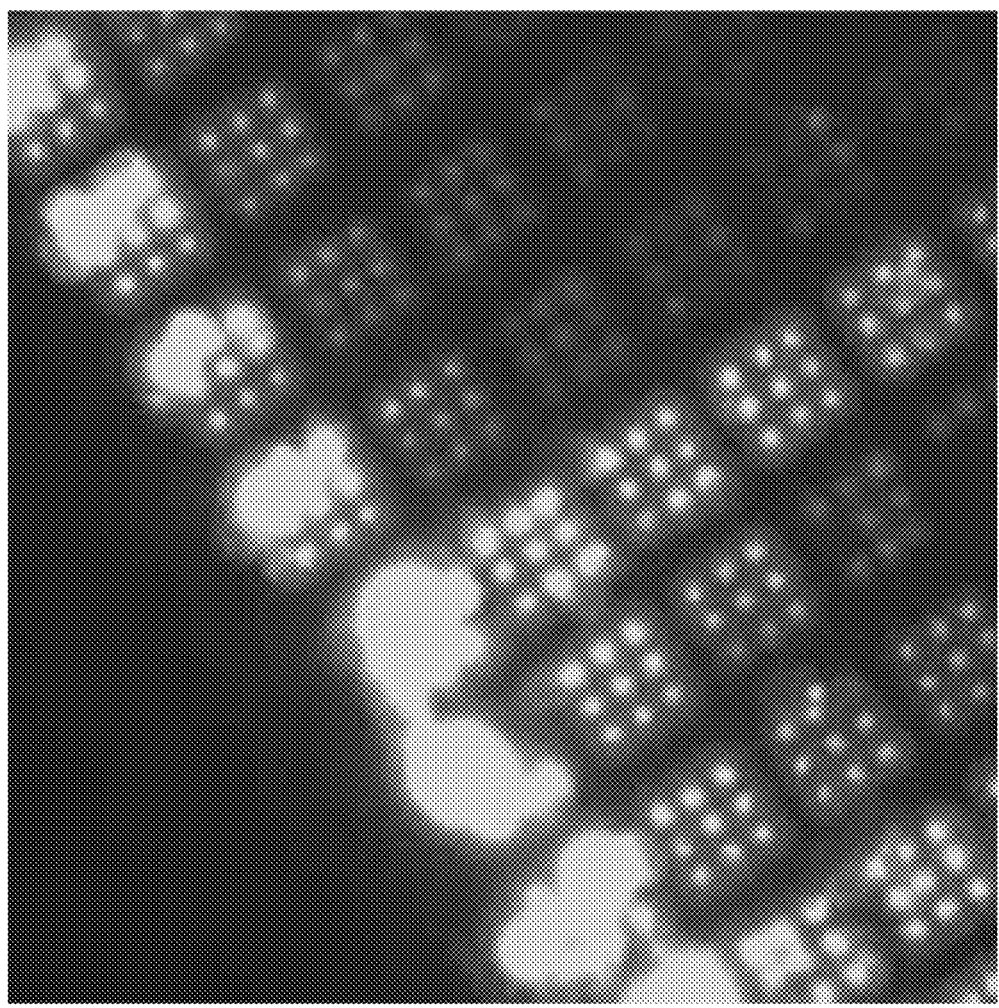
FIG. 50 is a fluorescence micrograph of a lipid multilayer microarray. Live cell imaging revealed cell adhesion to the surface and uptake of the lipids from the array.

FIG. 50 shows a fluorescence micrograph of a lipid multilayer microarray. Live cell imaging revealed cell adhesion to the surface and uptake of the lipids from the array.

Figure 51:
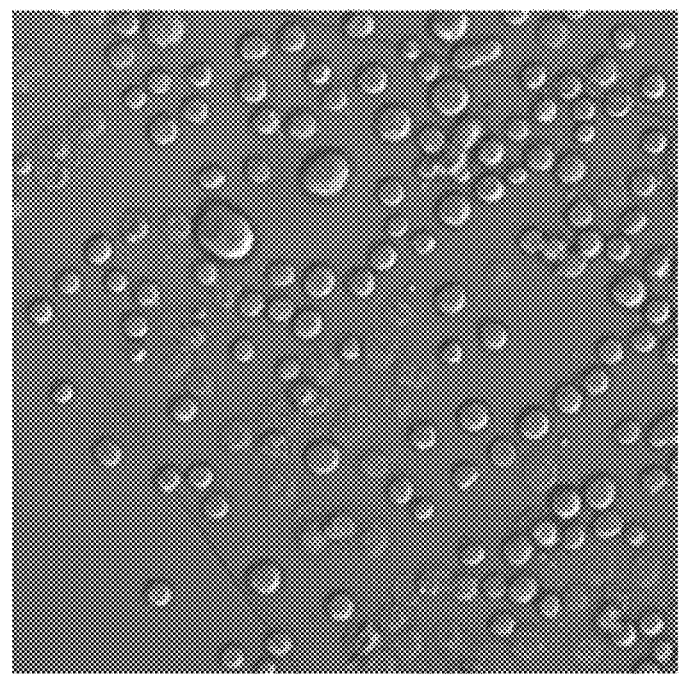
FIG. 51 is a brightfield micrograph of cells cultured over the lipid multilayer microarray.

FIG. 51 shows a brightfield micrograph of cells cultured over the lipid multilayer microarray.

Figure 52:
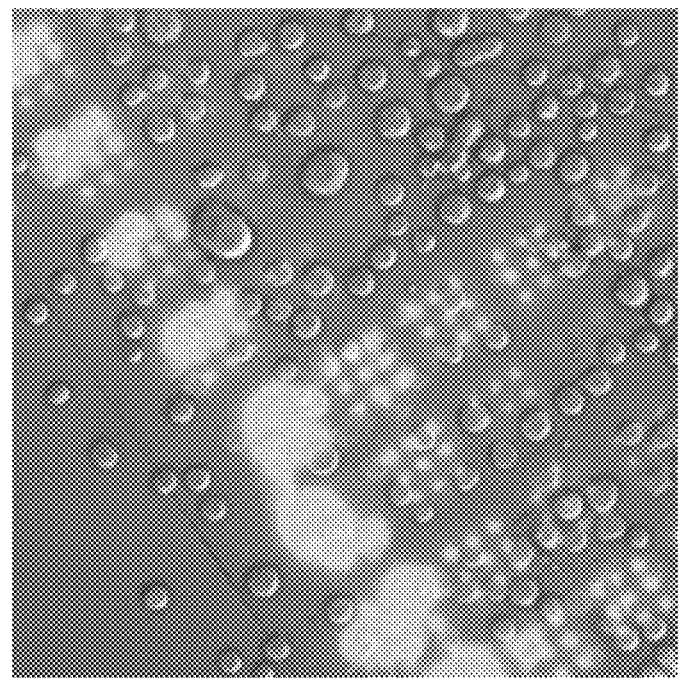
FIG. 52 is an overlay of FIG. 50 and FIG. 51.

FIG. 52 shows is an overlay of FIG. 50 and FIG. 51.

Figure 53:
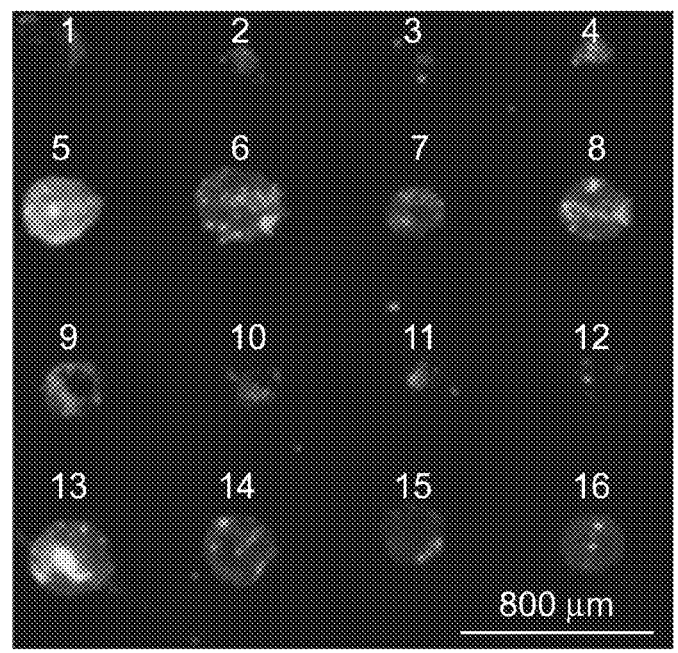
FIG. 53 is a fluorescence micrograph of an array of 16 different lipid mixtures, labeled green with a fluorescently labeled lipid.

FIG. 53 shows a fluorescence micrograph of an array of 16 different lipid mixtures, labeled green with a fluorescently labeled lipid.

Example 10

Figure 54:
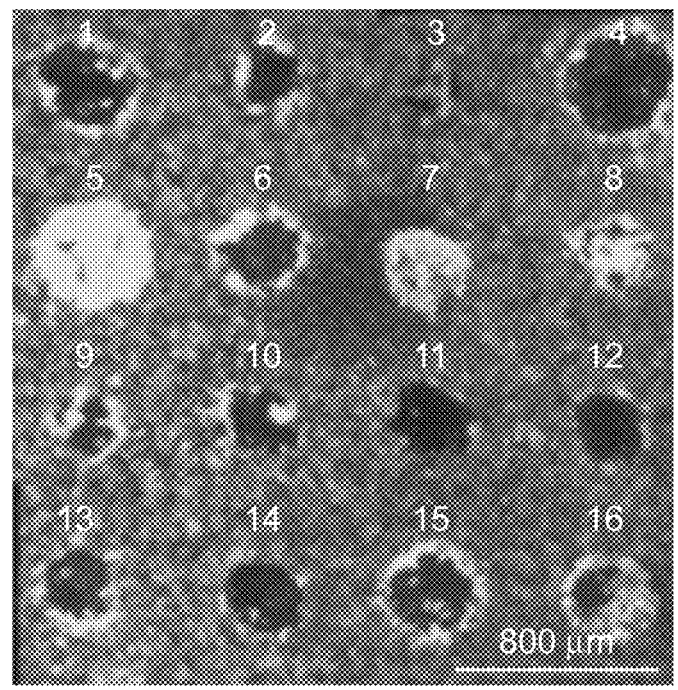
FIG. 54 is a fluorescence micrograph of cells after culture on the array and staining.
Figure 55:
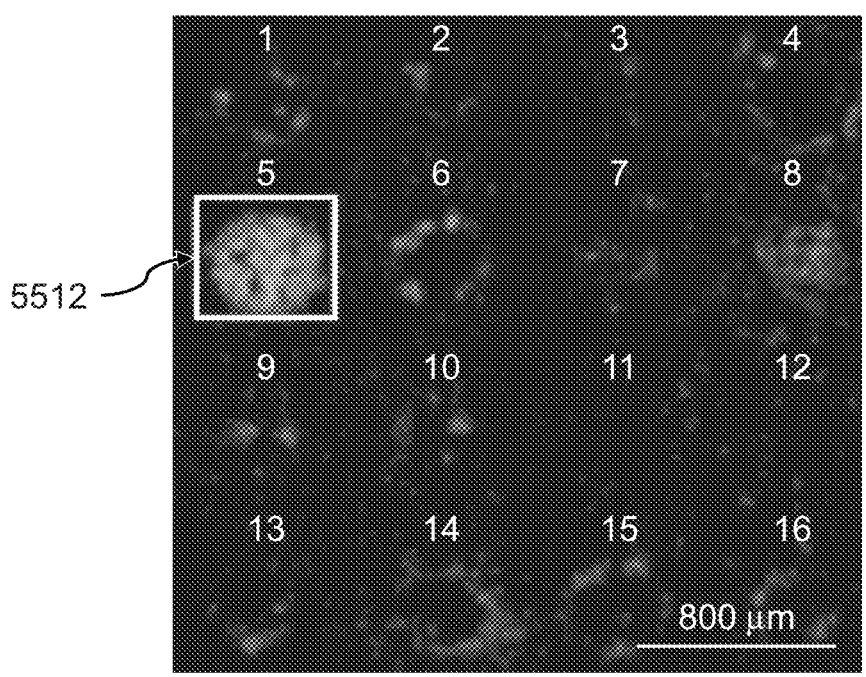
FIG. 55 is an image of the results of experiment where 16 different liposomal drug formulations arrayed onto a PDSM stamp and arrayed onto a glass surface.
Figure 56:
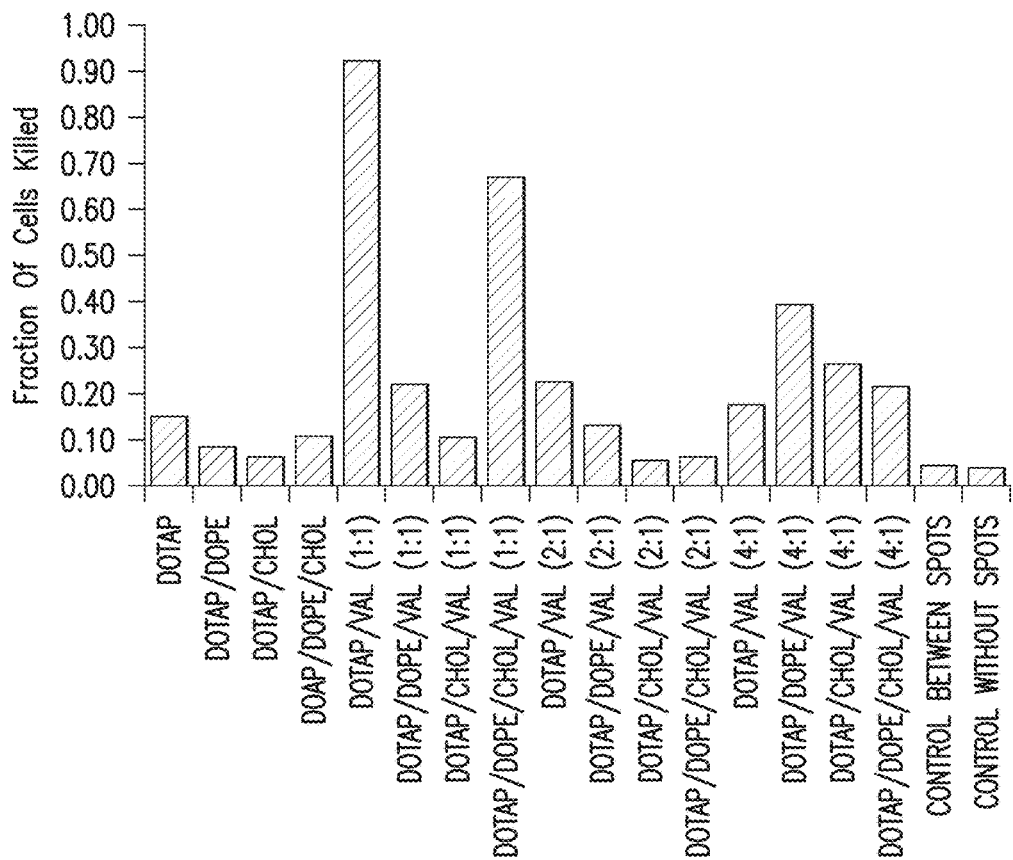
FIG. 56 is a graph showing the fraction of cells killed over each drug pattern area for the efficacy assay of FIG. 55.
Figure 57:
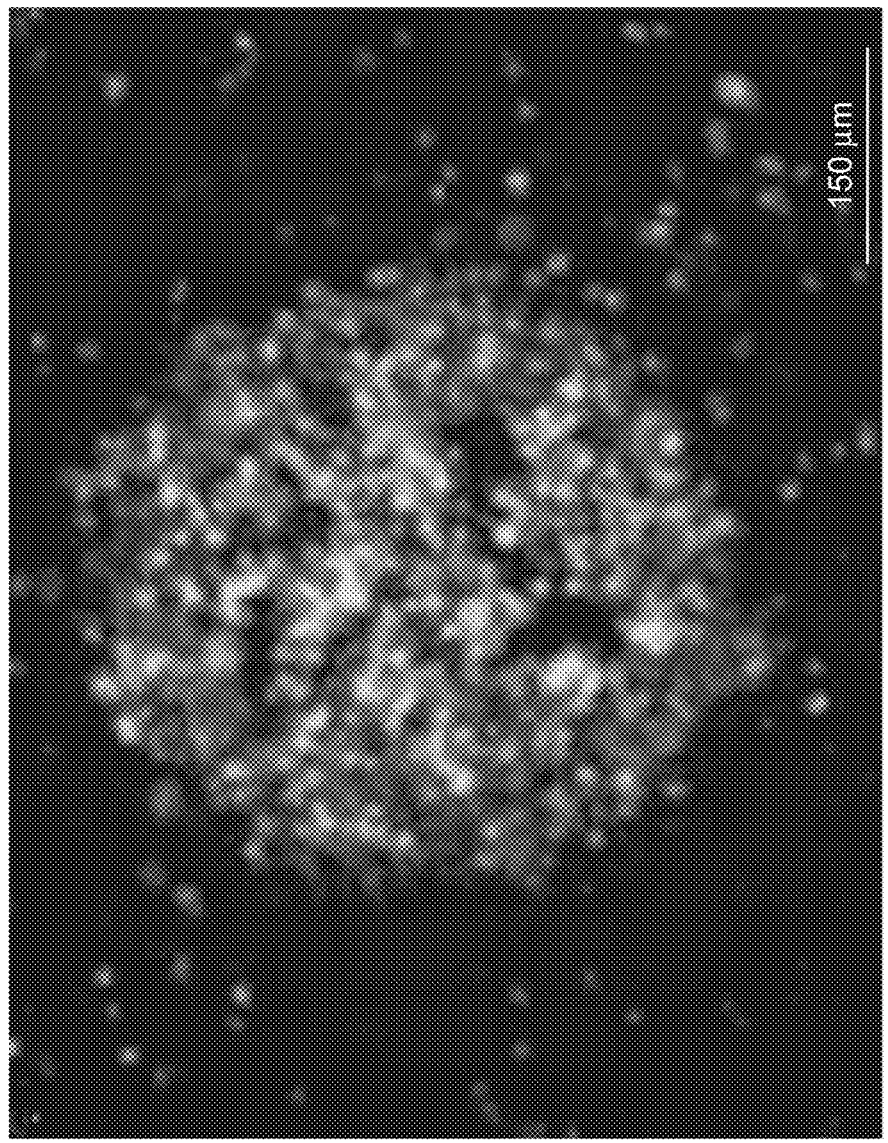
FIG. 57 is an enlarged view of a boxed region of FIG. 55.

Sixteen different liposomal drug formulations were array onto a PDMS stamp and arrayed onto a glass surface as shown in FIG. 53. The sixteen different formulations were: [1] DOTAP only, [2] DOTAP+Valinomycin (1:1), [3] DOTAP+Valinomycin (2:1), [4] DOTAP+Valinomycin (4:1), [5]—DOTAP+Valinomycin (8:1), [6] DOTAP/DOPE (30:70)+Valinomycin (1:1), [7] DOTAP/DOPE (30:70)+Valinomycin (2:1), [8] DOTAP/DOPE (30:70)+Valinomycin (4:1), [9] DOTAP/DOPE (30:70)+Valinomycin (8:1), [10] DOTAP/Cholesterol (20 mol %)+Valinomycin (1:1), [11] DOTAP/Cholesterol (20 mol %)+Valinomycin (2:1), [12] DOTAP/Cholesterol (20 mol %)+Valinomycin (4:1), [13] DOTAP/Cholesterol (20 mol %)+Valinomycin (8:1), [14] DOTAP/DOPE (30:70)/Cholesterol (20 mol %)+Valinomycin (1:1), [15] DOTAP/DOPE (30:70)/Cholesterol (20 mol %)+Valinomycin (2:1), [16] DOTAP/DOPE (30:70), indicated by numbers 1, 2, 3, 4, 5, 6, 7, 8, 9, 10, 11, 12, 13, 14, 15 and 16 respectively in FIGS. 54, 55 and 56. FIG. 54 shows cells cultured on each of the sixteen different formulations. FIG. 55 is an image of the results of the experiment where the 16 different liposomal drug formulations arrayed onto a PDSM stamp and arrayed onto a glass surface. Boxed region 5512 of FIG. 55 shows the results for formulation 5. FIG. 56 is a graph showing the fraction of cells killed over each drug pattern area for the efficacy assay of FIG. 53 as well as for control regions between the sixteen spots and for control regions without spots. FIG. 57 is an enlarged view of boxed region 5512.

Example 11

Characterization of Lipid Films for Cell Migration Assay

Figure 58:
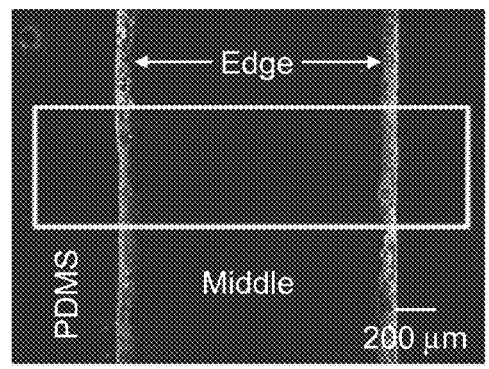
FIG. 58 is a fluorescent image of arrays at start lipid concentration of 2 µg/ml (selection in white used for intensity profile).
Figure 59:
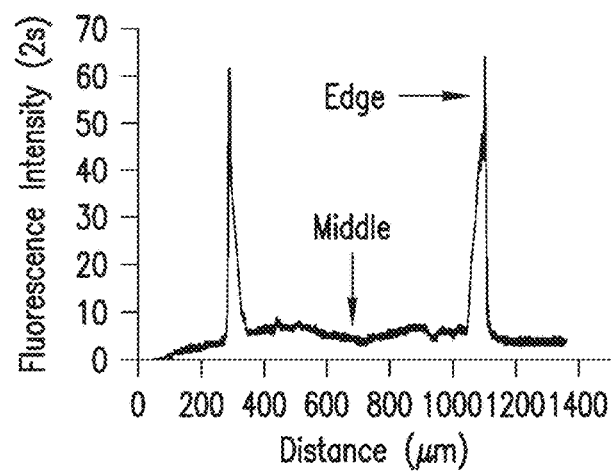
FIG. 59 is a plot profile graph of the vertically average fluorescence intensity profile across the horizontal cross section outlined in FIG. 58.
Figure 60:
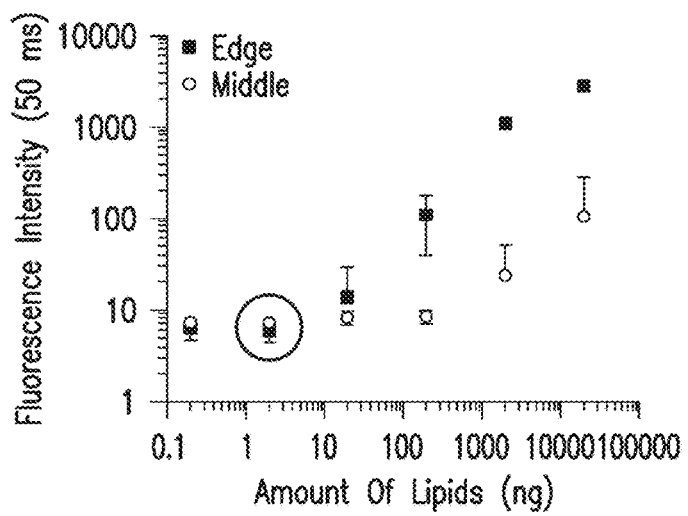
FIG. 60 is a graph of size of patterns calibrated from fluorescence intensity of edge and middle of channel.

The optimal thickness of lipid films was initially determined using fluorescent analysis shown in FIGS. 58, 59 and 60. Previously, it has been shown that fluorescent intensity of DOPE-rhodamine doped lipids is directly correlated to lipid multilayer height or thickness.[18] A proportional relationship was also observed from these lipid films between sensitivity (fluorescence intensity versus camera exposure time) and the amount of lipids added between the PDMS stencils. The thickness of the lipid multilayers can be controlled by the amount of lipids added between the stencils (FIG. 60). The fluorescence data for the edge and middle were taken at different exposure times for imagine. The circled point in FIG. 60 indicates the concentration used in FIGS. 58 and 59 and data is expressed as standard error of the mean. The initial concentration of lipid determined how the lipids dried within the PDMS channels. Adding 200 ng of lipid or higher caused excess lipids to be dried within the middle of the PDMS stencils in addition to thicker multilayers on the edges of the stencil. However, lower amounts of lipid only dried to the edges of the barriers (FIG. 59). This control of multilayer thickness was important when cells were added to the assay.

Example 12

Cell Adhesion on Different Lipid Multilayer Thicknesses

Figure 61:
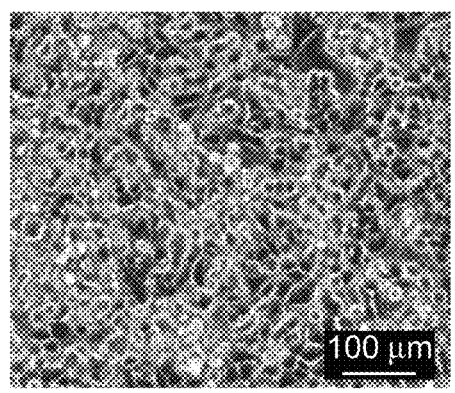
FIG. 61 is a micrograph in phase contrast of adherent HeLa cells in channels created from lipid concentrations of 2 µg/ml.
Figure 62:
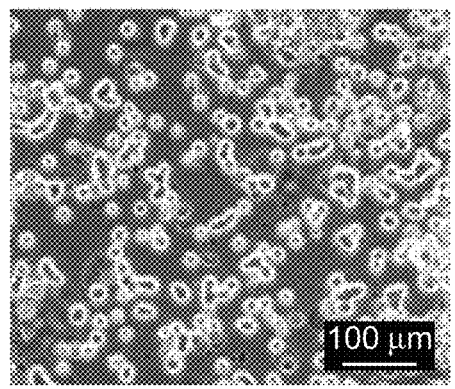
FIG. 62 is a micrograph in phase contrast of HeLa cells poorly spread out and attached on substrate created from lipid concentrations of 20 mg/ml.
Figure 63:
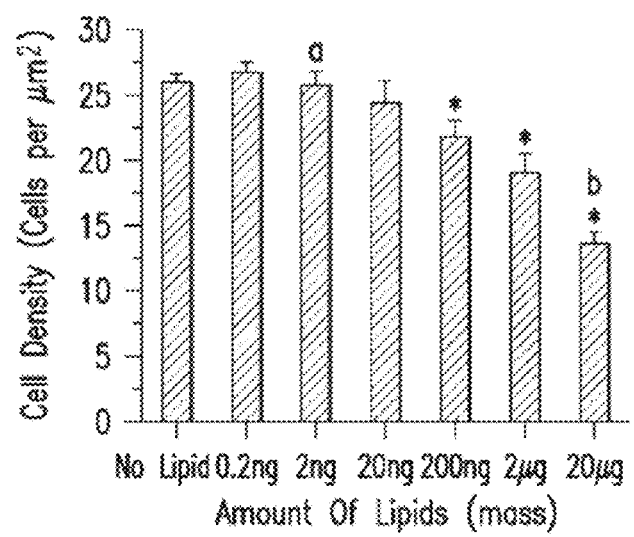
FIG. 63 is a graph of adherent cell density versus lipid concentration solution used to form films in assay channels (concentrations used in FIGS. 61 and 62 are indicated).

The effect of lipid multilayer thickness on cell adhesion was determined in FIGS. 61, 62 and 63. HeLa cells grown on lipid multilayers created from 200 ng of lipids or more exhibited abnormal morphology and appeared dead compared to thinner multilayers (FIGS. 61 and 62). This toxic effect could be from the cationic lipid DOTAP that was used, which can be cytotoxic at high concentrations.[78] Cells were adherent to lipid films created from 20 ng (initial solution with concentration of 20 µg/ml) or lower but began to adhere significantly less ($p<0.05$) at higher concentrations compared to untreated glass (FIG. 63). As shown in FIG. 61, 2 µg/ml is the substrate concentration that is adherent for HeLa cells to spread out and attach. A higher multilayer thickness results in cells looking balled and not spread out leading to apoptosis (FIG. 62). The asterisks represent significant different from control ($p<0.05$). Images and data were collected after 2 hours of incubation and data is expressed as standard error of the mean. These findings corroborate other studies that cells have poor adhesion to certain material surfaces such as lipid bilayers.[77] High concentrations of lipid on the surface could also influence the ability of cells to attach to the surface normally by disrupting the ability of adhesion proteins to interact with the surface. Additionally, higher numbers of dead cells were observed over regions with larger amounts of lipid (data not shown).

Example 13

Cell Migration on Different Lipid Multilayer Thicknesses

Figure 64:
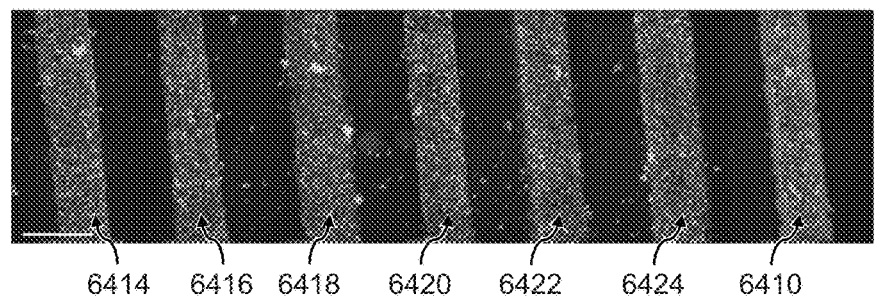
FIG. 64 is an image showing initial HeLa cell epithelial sheets before migration.
Figure 65:
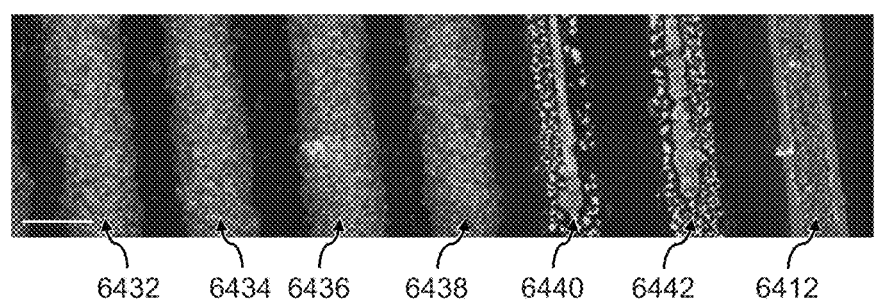
FIG. 65 is an image showing initial HeLa cell epithelial sheets 24 hours after migration.
Figure 66:
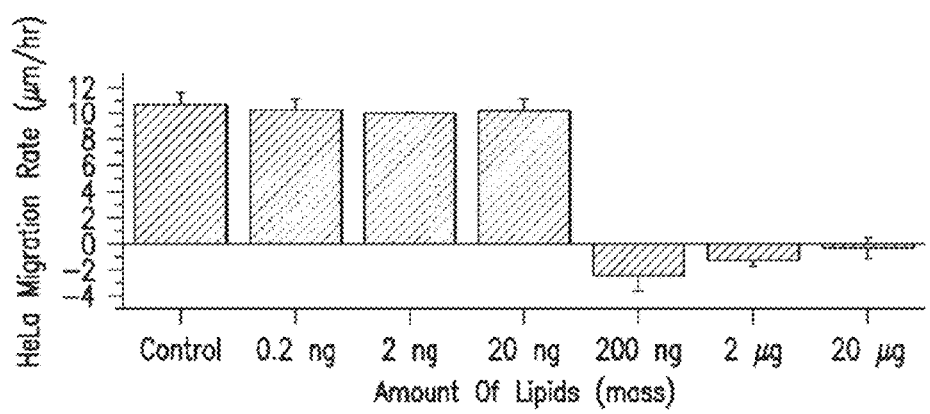
FIG. 66 is a graph showing the average distance of migration edge of HeLa cells over 24 hours at 0, 200 ng/ml, 2 µg/ml, 20 µg/ml, 200 µg/ml, 2 mg/ml, and 20 mg/ml (left to right on graph).

The effect of lipid multilayer thickness on HeLa cell migration was determined in FIGS. 64, 65 and 66. Phase contrast and fluorescent micrographs were taken immediately after PDMS barrier removal and 24 hours after to measure the migration rate over time (FIGS. 64 and 65, respectively). In FIG. 65, lipid spots indicated by arrows 6410 and 6412 are doped with 1 mol percent DOPE-rhodamine and cells indicated by arrows 6414, 6416, 6418, 6420, 6422, 6424, 6432, 6434, 6436, 6438, 6440 and 6442 are stained with SYTO9. Images in FIGS. 64 and 65 are 6×3 stitched micrograph images captured with a motorized stage. The asterisk represents significant difference from control ($p<0.05$) and data is expressed as standard error of the mean. Scale bars are 1000 µm. To visualize the amount of lipid on the surface, rhodamine-DOPE lipid was doped at 1 molar percent with the DOTAP lipid. The cells were stained with SYTO9, a live cell DNA stain. The migration rate of HeLa cells was not significantly ($p<0.05$) affected by lipid thickness in channels created from lipid solutions at a concentration of 20 µg/ml or lower but were significantly hindered at higher concentrations (FIG. 66). Excess lipid on the surface either causes reduced cell attachment or cell death which significantly reduces the ability of the cell strip to migrate. 20 ng of lipid (lipid solution at a concentration of 20 µg/ml in ethanol) was used for all migration assays.

Example 14

Effect of Docetaxel from Lipid Multilayer Films on Cell Migration

Figure 67:
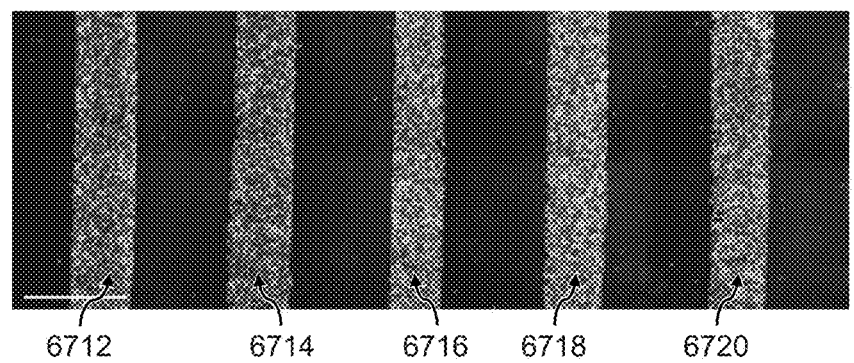
FIG. 67 is a fluorescent micrograph of cells at time 0 hours after contact with lipid encapsulated docetaxel films.
Figure 68:
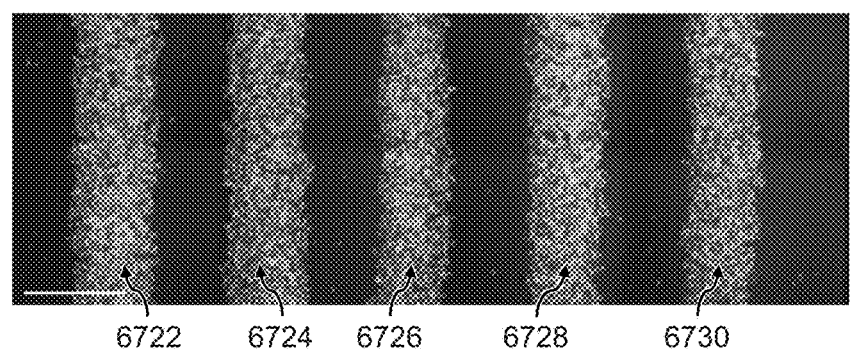
FIG. 68 is a fluorescent micrograph of cells after 24 hours after contact with lipid encapsulated docetaxel films.
Figure 69:
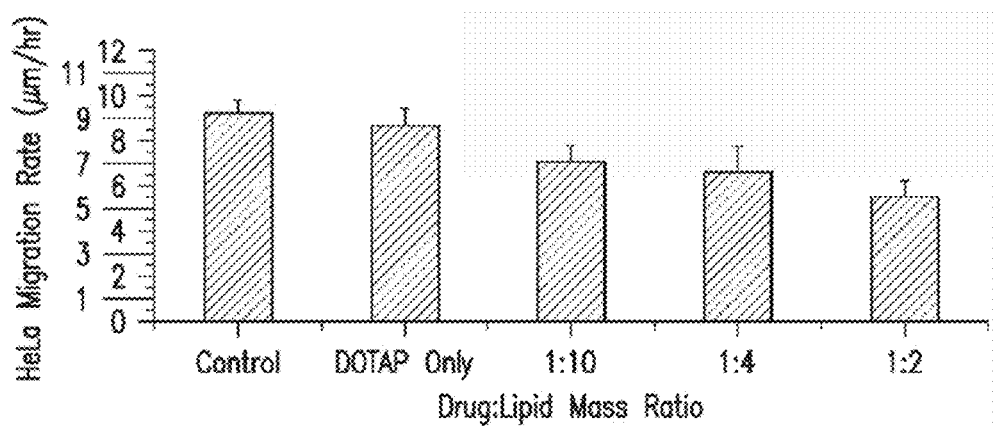
FIG. 69 is a graph of migration rate (in µm/hour) versus drug to lipid ratio (by mass).

A lipid based cell assay is used to investigate the effect of the antimicrotubule drug docetaxel on HeLa cellular migration rate, as shown in FIGS. 67, 68 and 69. Here, the migration assay is tested with docetaxel, a lipophilic drug that is poorly soluble in water (less than 0.025 mg/L) and has a log P of 4.1.[79] Docetaxel was delivered into HeLa cells by encapsulated lipid films. HeLa cell migration is shown to also be inhibited by docetaxel which suggests that docetaxel and other taxol derivatives could be used to target different cell processes for cancer therapies. Three different docetaxel to lipid ratios (by mass) of 1:10, 1:4 and 1:2 significantly ($p<0.05$) reduced collective cell migration compared to control group (FIG. 69). Lipids in FIG. 67 are stained with DOPE-rhodamine. Cell staining dyes used in FIGS. 67 and 68 were SYTO9 DNA stain (6712, 6714, 6716, 6718, 6718, 6720, 6722, 6724, 6726, 6728, and 6730). Images in FIGS. 67 and 68 are 4×3 stitched 4× images captured with a motorized stage. The asterisk represents significant difference from control ($p<0.05$) and data is expressed as standard error of the mean. Scale bars are 1000 µm. In addition, the results indicated that docetaxel delivered by encapsulated lipid films reduced the migration rate of the cells dose-dependently over 24 hours due to disruption of microtubule dynamics by docetaxel (FIG. 69). Docetaxel is most likely influencing many different cell processes such as inhibiting cell division and migration while increased apoptosis. These effects in combination can reduce the ability of a monolayer of cells to migrate across the glass coverslip compared to untreated cells. Therefore, docetaxel should have some inhibitory effect on the ability of HeLa cells to migrate in a coordinated fashion.

One advantage of this lipid-based surface delivery system over other existing assays is that it allows the study of the effects of poorly water soluble compounds such as docetaxel on cell movement following drug delivery into the cells. Different amounts or types of compounds can also be tested at the same time in parallel which leads to a reduced amount time for running separate tests. Another advantage is that uptake of drugs into cells can be facilitated without DMSO, which can be hazardous to work with because it functions as a chemical carrier and easily penetrates the skin along with solubilized compounds. Additionally, this assay requires smaller amounts of drug per assay as compared to a standard scratch migration assay which requires dissolving the drug at certain concentrations in each micro-well. Furthermore, migrating cells on the edge of the barrier region are exposed locally to lipid encapsulated drug compared to proliferating cells in the interior region of monolayer culture.

Example 15

The Effect of Docetaxel and Brefeldin A on HeLa Cell Migration Using Evaporative Edge Lithography (EEL)

A lipid-based cell assay to investigate the effect of the antimicrotubule drug docetaxel and brefeldin A that inhibits intracellular protein transport on HeLa cellular migration rate. The migration assay was tested with two lipophilic drugs: (1) docetaxel, which is poorly soluble in water (less than 0.025 mg/L) and has a log P of 4.1, and (2) brefeldin A that has a log P of 1.61.[79,80] Docetaxel and brefeldin A were delivered into HeLa cells by uptake from encapsulated lipid films.

FIG. 70 shows a merged micrograph of HeLa cell strip (in phase contrast) in contact with a DOTAP only fluorescent lipid film (doped with 1 mol % DOPE-rhodamine), 1 hour after PDMS barriers were removed. FIG. 71 shows the HeLa cell strip of FIG. 70, 24 hours after the PDMS barriers were removed. FIG. 72 is a merged image of a HeLa strip incubated with a docetaxel-encapsulated fluorescent lipid film, 1 hour after PDMS barriers were removed. FIG. 73 shows the HeLa cell strip of FIG. 72, 24 hours after the PDMS barriers were removed. FIG. 74 shows a merged image of HeLa strip incubated with a brefeldin A encapsulated lipid film, hour after PDMS barriers were removed. FIG. 73 shows the HeLa cell strip of FIG. 72, 24 hours after the PDMS barriers were removed. A scale bar 7112 is shown in and is 200 µm.

Figure 76:
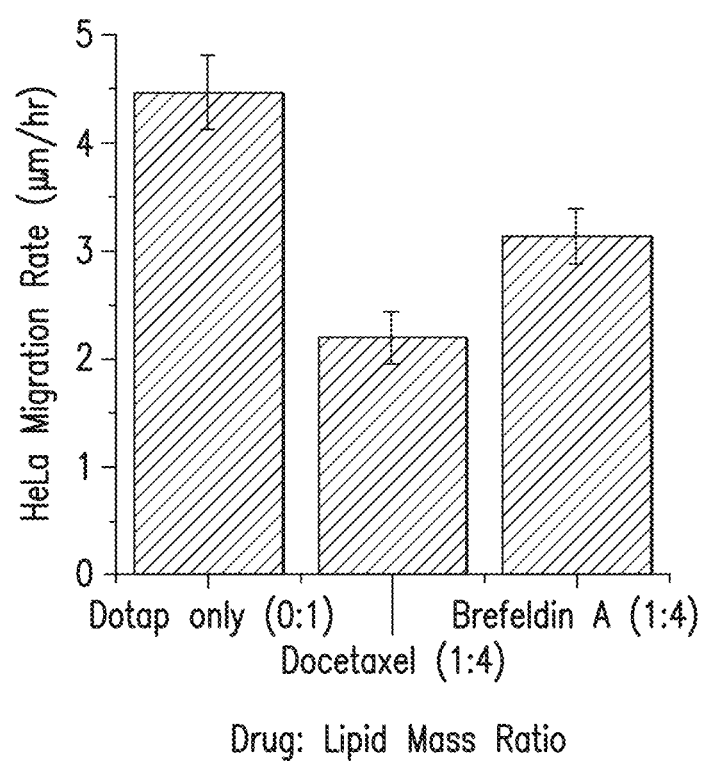
FIG. 76 is a graph of HeLa migration rate (µm/hr) as a function of drug treatment from lipid multilayer films.

As shown in FIGS. 70, 71, 72, 73, 74 and 75, HeLa cell migration is also inhibited by brefeldin A and docetaxel which suggests that docetaxel and other taxol derivatives could be used to target different cell processes for cancer therapies. Additionally, three different docetaxel to lipid ratios (by mass) of 1:10, 1:4 and 1:2 were able to be assayed at once on the same array and were found to significantly ($p<0.05$) reduce collective cell migration compared to control group. Furthermore, these results indicated that docetaxel delivered by encapsulated lipid films reduced the migration rate of the cells dose-dependently over 24 hours due to disruption of microtubule dynamics by docetaxel. Docetaxel is most likely influencing many different cell processes such as inhibiting cell division and migration while increased apoptosis. These effects in combination can reduce the ability of a monolayer of cells to migrate across the glass coverslip compared to untreated cells. Therefore, it is believed that docetaxel should have some inhibitory effect on the ability of HeLa cells to migrate in a coordinated fashion. HeLa migration rate (µm/hr) as a function of drug treatment from lipid multilayer films for these assays is shown in FIG. 76. In FIG. 76, * represents significant difference from DOTAP only control ($p<0.05$). Data for each treatment was performed in triplicate twice (n=6) and is expressed as standard error of the mean.

One advantage of this lipid-based surface delivery system over other existing assays is that it allows the study of the effects of poorly water soluble compounds such as docetaxel on cell movement following drug delivery into the cells. Different amounts or types of compounds can also be tested at the same time in parallel which leads to a reduced amount time for running separate tests. Another advantage is that uptake of drugs into cells can be facilitated without DMSO, which can be hazardous to work with because it functions as a chemical carrier and easily penetrates the skin along with solubilized compounds. Additionally, this assay requires smaller amounts of drug per assay as compared to a standard scratch migration assay which requires dissolving the drug at certain concentrations in each micro-well. Furthermore, migrating cells on the edge of the barrier region are exposed locally to lipid encapsulated drug compared to proliferating cells in the interior region of monolayer culture.

All documents, patents, journal articles and other materials cited in the present application are incorporated herein by reference.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

REFERENCES

The following references are referred to above and are incorporated herein by reference:
1. Barenholz, Y., Gibbes, D., Litman, B. J., Goll, J., Thompson, T. E., and Carlson, F. D., "A simple method for the preparation of homogeneous phospholipid vesicles," *Biochemistry* 16, 2806-10 (1977).
2. Szokam F., and Papahadjopoulos, D., "Comparative properties and methods of preparation of lipid vesicles (liposomes)," *Annu. Rev. Biophys. Bio* 9, 467-508 (1980).
3. Gustafsson, J., Arvidson, G., Karlsson, G., and Almgren, M. "Complexes between cationic liposomes and DNA visualized by Cryo-Tem," *BBA-Biomembranes* 1235, 305-12 (1995).
4. Kwon, C. H., Wheeldon, I., Kachouie, N. N., Lee, S. H., Bae, H., Sant, S., Fukuda, J., Kang, J. W., Khademhosseini, A., "Drug-eluting microarrays for cell-based screening of chemical-induced apoptosis," *Anal. Chem.* 83, 4118-25 (2011).
5. Malam, Y., Loizidou, M., and Seifalian, A. M., "Liposomes and nanoparticles: nanosized vehicles for drug delivery in cancer," *Trends Pharmacol. Sci.* 30, 592-99 (2009).
6. Porter, C. J. H., Trevaskis, N. L., and Charman, W. N., "Lipids and lipid-based formulations:optimizing the oral delivery of lipophilic drugs," *Nat. Rev. Drug Discov.* 6, 231-48 (2007).
7. Torchilin, V. P., "Micellar nanocarriers: pharmaceutical perspectives," *Pharm. Res.* 24, 1-16 (2007).
8. Koren, E., and Torchilin, V. P., "Drug carriers for vascular drug delivery," *IUBMB Life* 63, 586-95 (2011).
9. Gregoriadis, G., "Engineering liposomes for drug delivery: progress and problems," *Trends in Biotechnology* 13, 527-37 (1995).
10. Kusi-Appiah, A. E., Vafai, N., Cranfill, P. J., Davidson, M. W., and Lenhert, S., "Lipid multilayer microarrays for in vitro lipomosomal drug delivery and screening," *Biomaterials* 33, 4187-94 (2012).
11. Majd, S, and Mayer, M., "Hydrogel stamping of arrays of supported lipid bilayers with various lipid compositions for the screening of drug-membrane and protein-membrane interactions," *Angew. Chem. Int. Ed.* 44, 6697-6700 (2005).
12. Moran-Mirabal, J. M., Edel, J. B., Meyer, G. D., Throckmorton, D., Singh, A. K., and Craighead, H. G., "Micrometer-sized supported lipid bilayer arrays for bacterial toxin binding studies through total internal reflection fluorescence microscopy," *Biophys. J.* 89, 296-305 (2005).
13. Deng, Y., Wang, Y., Holtz, B. Li, J., Traaseth, N., Veglia, G., Stottrup, B. J., Elde, R., Pei, D., Guo, A., and Zhu, X. Y., "Fluidic and air-stavle supported lipid bilayer and cell-mimicking microarrays," *J. Am. Chem. Soc.* 130, 6267-71 (2008).

14. Yamazaki, V., Sirenko, O., Schafer, R. J., Nguyen, L., Gutsmann, T., Brade, L., and Groves, J. T., "Cell membrane array fabrication and assay technology," *BMC Biotechnology* 2005, doi: 10.1186/1472-6750-5-18 (2005).
15. Lenhert, S., Brinkmann, F., Laue, T., Walheim, S., Vannahme, C., Klinkhammer, S., Xu, M., Sekula, S., Mappes, T., Schimmel, T., and Fuchs, H., "Lipid multilayer gratings," *Nat. Nanotechnol.* 5, 275-79 (2010).
16. Lenhert, S., Sun, P., Wang, Y. H., Fuchs, H., and Mirkin, C. A., "Massively parallel dip-pen nanolithography of heterogeneous supported phospholipid multilayer patterns," *Small* 3, 71-75 (2007).
17. Sekula, S., Fuchs, J., Weg-Remers, S., Nagel, P., Schuppler, S., Fragala, J., Theilacker, N., Franzreb, M., Wingren, C., Ellmark, P., Borrebaeck, C. A. K., Mirkin, C. A., Fuchs, H., and Lenhert, S., "Multiplexed lipid dip-pen nanolithography on subcellular scales for the templating of functional proteins and cell culture," *Small* 4, 1785-93 (2008).
18. Nafday, O. A., and Lenhert, S. "High-throughput optical quality control of lipid multilayers fabricated by dip-pen nanolithography," *Nanotechnology* 22, doi:225301 (2011).
19. Perino-Gallice, L., Fragneto, G., Mennicker, U., Salditt, T., and Rieutord, F., "Dewetting of solid-supported multilamellar lipid layers," *Eur. Phys. J. E* 8, 275-82 (2002).
20. Mathieu, M. Schunk, D., Franzka, S., Mayer, C., and Hartmann, N., "Temporal stability of photothermally fabricated micropatterns in supported phospholipid multilayers," *J. Vac. Sci. Technol. A* 28, 953-57 (2010).
21. Perl, A., Reinhoudt, D. N., and Huskens, J., "Microcontact printing: limitations and achievements," *Adv. Mater.* 21, 2257-68 (2009).
22. Nafday, O. A., Lowry, T. W., and Lenhert, S., "Multifunctional lipid multilayer stamping," *Small* 8, 1021-28 (2012).
23. Heller, M. J., "DNA microarray technology: devices, systems, and applications," *Annu. Rev. Biomed. Eng.* 4, 129-53 (2002).
24. Howbrook, D. N., van der Valk, A. M., O'Shaughnessy, M. C., Sarker, D. K., Baker, S. C., and Lloyd, A. W., "Developments in microarray technologies," *Drug Discov. Today* 15, 648-51 (2003).
25. Eteshola, E., and Leckband, D., "Development and characterization of an ELISA assay in PDMS microfluidic channels," *Sens. Actuator B-Chem.* 72, 129-33 (2001).
26. Braunschweig, A. B., Huo, F. W., and Mirkin, C. A., "Molecular printing," *Nat. Chem.* 1, 353-58 (2009).
27. Salaita, K., Wang, Y. H., and Mirkin, C. A., "Applications of dip-pen nanolithography," *Nat. Nanotechnol.* 2, 145-55 (2007).
28. Ginger, D. S., Zhang, H., and Mirkin, C. A., "The evolution of dip-pen nanolithography," *Angew. Chem. Int. Ed.* 43, 30-45 (2004).
29. Piner, R. D., Zhu, J., Xu, F., Hong, S. H., and Mirkin, C. A., "Dip-pen" nanolithography," *Science* 283, 661-63
30. Salaita, K., Wang, Y. H., Fragala, J., Vega, R. A., Liu, C., Mirkin, C. A. "Massively parallel dip-pen nanolithography with 55000-pen two-dimensional arrays," *Angew. Chem. Int. Ed.* 45, 7220-23 (2006).
31. Zhang, M., Bullen, D., Chung, S. W., Hong, S., Ryu, K. S., Fanm Z. F., and Mirkin, C. A., and Liu, C., "A MEMS nanoplotter with high density parallel dip-pen nanolithography probe arrays," *Nanotechnology* 13, 212-17 (2002).
32. Xia, Y. N., and Whitesides, G. M., "Soft lithography," *Annu. Rev. Mater. Sci.* 28, 153-84 (1998).
33. Huo, F., Zheng, Z, Zheng, G, Giam, L., Zhang, H., and Mirkin, C. A., "Polymer pen lithography," *Science* 321 1658-60 (2008).
34. Kusi-Appiah, A., Vafai, N., Cranfill, P. J., Davidson, M. W. & Lenhert, S., "Lipid multilayer microarrays for in vitro liposomal drug delivery and screening," *Biomaterials* 33(16) 4187-94 (2012).
35. Jang, J. W., Smetana, A., and Stiles, P., "Multi-ink pattern generation by dip-pen nanolithography," *Scanning* 32, 24-29 (2010).
36. Chou, S. Y., Krauss, P. R., and Renstrom, P. J., "Imprint lithography with 25-nanometer resolution," *Science* 272, 85-87 (1996).
37. Torchilin, V. P., "Recent advances with liposomes as pharmaceutical carriers," *Nat. Rev. Drug Discov.* 4, 145-60 (2005).
38. Lenhert, S., Mirkin C. A., and Fuchs, H., "In situ lipid dip-pen nanolithography under water," *Scanning* 32, 15-23 (2010).
39. Mendez-Vilas, A., Jodar-Reyes, A. B., and Gonzalez-Martin, M. L., "Ultrasmall liquid droplets on solid surfaces: production, imaging, and relevance for current wetting research," *Small* 5, 1366-90 (2009).
40. Szymanski, P., Markowicz, M. and Mikiciuk-Olasik, E. "Adaptation of High-Throughput Screening in Drug Discovery-Toxicological Screening Tests," *International Journal of Molecular Sciences* 13, 427-452 (2012).
41. Sampieri, K. and Fodde, R., "Cancer stem cells and metastasis," *Seminars in Cancer Biology.*, 22, 187-193 (2012).
42. Brabletz, T., Jung, A., Spaderna, S., Hlubek F., and Kirchner, T., "Opinion: migrating cancer stem cells—an integrated concept of malignant tumour progression." *Nature Reviews Cancer*, 5, 744-749 (2005).
43. Eilken, H. M. and Adams, R. H., "Dynamics of endothelial cell behavior in sprouting angiogenesis," *Current Opinion in Cell Biology*, 22, 617-625 (2010).
44. Griffloen, A. W. and Molema, G., "Anti-angiogenesis: making the tumor vulnerable to the immune system," *Pharmacoogy Review.*, 52, 237-268 (2000).
45. Witte, M. B. and Barbul, A., "General principles of wound healing," The Surgical Clinics of North America., 77, 509-+(1997).
46. Aman, A. and Piotrowski, T. "Cell migration during morphogenesis," *Developmental Biology*, 341, 20-33 (2010).
47. Weijer, C. J. "Collective cell migration in development," *Journal of Cell Science.*, 122, 3215-3223 (2009).
48. Liang, C. C., Park, A. Y. and Guan, J. L., "In vitro scratch assay: a convenient and inexpensive method for analysis of cell imgration in vitro," *Nature Protocols.*, 2, 329-333 (2007).
49. Valster, A., Tran, N. L., Nakada, M., Berens, M. E., Chan A. Y. and Symons, M., "Cell migration and invasion assays," *Methods*, 37, 208-215 (2005).
50. van Horssen, R. and ten Hagen, T. L. M., "Crossing barriers: The new dimension of 2D cell migration assays," *Journal of Cellular Physiology.*, 226, 288-290 (2011).
51. Lenhert, S., Meier, M. B., Meyer, U., Chi, L. F. and Wiesmann, H. P., "Osteoblast alignment, elongation and migration on grooved polystyrene surfaces patterned by Langmuir-Blodgett lithography," *Biomaterials*, 26, 563-570 (2005).
52. Shin, K. D., Lee, M. Y., Shin, D. S., Lee, S., Son, K. H., Koh, S. Paik, Y. K., Kwon B. M. and Han, D. C., "Blocking tumor cell migration and invasion with biphenyl isoxazole derivative KRIBB3, a synthetic molecule that inhibits Hsp27 phosphorylation," *Journal of Biological Chemistry.*, 280, 41439-41448 (2005).
53. Gough, W., Hulkower, K. I., Lynch, R., McGlynn, P., Uhlik, M., Yan, L. and Lee, J. A, "A quantitative, facile, and high-throughput image-based cell migration method is a robust alternative to the scratch assay," *Journal of Biomolecular Screening,* 16, 155-163 (2011).
54. Attoub, S., Hassan, A. H., Vanhoecke, B., Iratni, R., Takahashi, T. Gaben, A.-M., Bracke, M., Awad, S., John, A., Kamalboor, H. A., Al Sultan, M. A. Arafat, K. Gespach, C. and Petroianu, G., "Inhibition of cell survival, invasion, tumor growth and histone deactylase activity by the dietary flavonoid luteolin in human epitholioid cancer cells," European Journal of Pharmacology, 651, 18-25 (2011).
55. Chung, S., Sudo, R., Mack, P. J., Wan, C. R., Vickerman, V. and Kamm, R. D., "Cell migration into scaffolds under co-culture conditions in a microfluidic platform," Lab on a Chip, 9, 269-275 (2009).
56. Conant, C. G., Nevill, J. T., Schwartz, M. and Ionescu-Zanetti, C., "Wound healing assays in well-plate coupled microfluidic devices with controlled parallel flow," Journal of the Association for Laboratory Automation, 15, 52-57 (2010).
57. Huang, X. W., Li, L., Tu, Q., Wang, J. C., Liu, W. M., Wang, X. Q., Ren, L. and Wang, J. Y., "On-chip cell migration assay for quantifying the effect of ethanol on MCF7 human breast cancer cells," Microfluid Nanofluid, 10, 1333-1341 (2011).
58. Poujade, M., Grasland-Mongrain, E., Hertzog, A, Jouanneau, J., Chavrier, P., Ladoux, B., Buguin, A. and Silberzan, P. "Collective migration of an epithelial monolayer in response to a model wound," Proceedings of the National Academy of Sciences of the United States of America, 104, 15988-15993 (2007).
59. Wang, L., Zhu, J., Deng, C., Xing, W. L. and Cheng, J., "An automatic and quantitative on-chip cell migration assay using self-assembled monolayers combined with real-time cellular impedance sensing," Lab on a Chip, 8, 872-878 (2008).
60. Kim, B. J. and Wu, M. M., "Microfluidics for mammalian cell chemotaxis," Annals of Biomedical Engineering, 40, 1316-1327 (2012).
61. Liu, T. J., Lin, B. C. and Qin, J. H., "Carcinoma-associated fibroblasts promoted tumor spheroid invasion on a microfluidic 3D co-culture device," Lab on a Chip, 2010, 10, 1671-1677.
62. Wang, Z., Kim, M.-C., Marquez, M. and Thorsen, T., "High-density microfludic arrays for cell cytotoxicvity analysis," Lab on a Chip, 7, 740-745 (2007).
63. Kwak, Y. H., Hong, S. M. and Park, S. S., "A single cell tracking system in real-time," Cellular Immunology, 265, 44-49 (2010).
64. Puliafito, A., Hufnagel, L., Neveu, P., Streichan, S., Sigal, A., Fygenson, D. K. and Shraiman, B. I. "Collective and single cell behavior in epithelial contact inhibition," Proceedings of the National Academy Sciences of the United States of America, 109, 739-744 (2012).
65. Adanja, I., Megalizzi, V., Debeir, O., and Decaestecker, C. "A new method to address unmet needs for extracting individual cell migration features from a large number of cells embedded in 3D volumes," PLoS One, 6 (2011).
66. Diaz-Mochon, J. J., Tourniaire, G. and Bradley, M., "Microarray platforms for enzymatic and cell-based assays," Chemical Society Reviews, 36, 449-457 (2007).
67. Yarrow, J. C., Totsukawa, G., Charras, G. T. and Mitchison, T. J. "Screening for cell migration inhibitors via automated microscopy reveals a Rho-kinase inhibitor," Chemistry & Biology, 12, 385-395 (2005).
68. Bailey, S. N., Sabatini D. M. and Stockwell, B. R., "Microarrays of small molecules embedded in biodegradable polymers for use in mammalian cell-based screens," Proceedings of the National Academy Sciences of the United States of America, 101, 16144-16149 (2004).
69. Tourniaire, G., Collins, J., Campbell, S., Mizomoto, H. Ogawa, S., Thaburet, J. F. and Bradley, M. "Polymer microarrays for cellular adhesion," Chemical Communications, 2118-2120 (2006).
70. Balakin, K. V., Savchuk, N. P. and Tetko, I. V., "Inh silico approaches of aqueous and DMSO solubility of drug-like compounds: trends, problems and solutions," *Current Medicinal Chemistry,* 13, 223-241 (2006).
71. Jacob, S. W. and Herschler, R. "Pharmacology of DMSO," Cryobiology, 23, 14-27 (1986).
72. Grein, T. A., Freimark, D., Weber, C., Hudel, K., Wallrapp, C. and Czermak, P., "Alternatives to dimethylsulfoxide for serum-free cryopreservation of human mesenchymal stem cells," International Journal of Artificial Organs, 2010, 33, 370-380.
73. Majd, S. and Mayer, M., "Generating arrays with high content and minimal consumption of functional membrane proteins," Journal of American Chemical Society, 130, 16060-16064 (2008).
74. Diguet, A., Le Berre, M., Chen, Y. and Baigl, D., "Preparation of phospholipid multilayer patterns of controlled size and thickness by capillary assembly on a microstructured substrate," Small, 5, 1661-1666 (2009).
75. Brinker, C. J., Lu, Y. F., Sellinger, A. and Fan, H. Y., "Evaporation-induced self-assembly: Nanostructures made easy," Advanced Materials, 11, 579-+(1999).
76. Yuan, B., Xing, L. L., Zhang, Y. D., Lu, Y., Mai, Z. H. and Li, M., "Self-assembly of highly oriented lamellar nanoparticle-phospholipid nanocomposites on solid surfaces," *Journal of American Chemical Society,* 129, 11332-+(2007).
77. Groves, J. T., Mahal, L. K. and Bertozzi, C. R. Langmuir, "Control of cell adhesion and growth with micropatterned supported lipid membranes," 17, 5129-5133 (2001).
78. Tang, F. and Hughes, J. A., "Synthesis of a single-tailed cationic lipid and investigation of its transfection," *Journal of Controlled Release,* 62, 345-358 (1999).
79. Fayad, W., Rickardson, L., Haglund, C., Olofsson, M. H., D'Arcy, P., Larsson, R., Linder, S. and Fryknas, M., "Identification of agents that induce apoptosis oif multicellular tumour spheroids: enrichment for mitotic inhibitors with hydrophobic properties," *Chemical Biology and Drug Design,* 78, 547-557 (2011).
80. J.-W. Zhu, H. Nagasawa, F. Nagura, S. B. Mohamad, Y. Uto, K. Ohkura and H. Hori, *Bioorg. Med. Chem.,* 8, 455-463 (2000).

What is claimed is:

1. A method of creating one or more arrays of lipid multilayer structures by edge evaporation lithography (EEL), the steps of EEL comprising:
  (a) placing a stencil having openings on a surface of a substrate thereby forming barriers and spaces between the barriers on the substrate;
  (b) adding a plurality of lipid solutions to the spaces between the barriers, each lipid solution of the plurality of lipid solutions comprising a solvent and one or more lipids,
  (c) forming one or more arrays of lipid multilayer structures on the substrate by evaporating the solvent from each of the plurality of lipid solutions in the spaces between the barriers on the substrate thereby forming the lipid multilayer structures only along edges of the barriers and forming surface regions between the lipid multilayer structures, wherein the surface regions do not contain lipid multilayer structures; and (d) removing the stencil from the substrate to form one or more arrays of lipid multilayer structures on the substrate that correspond to an outline of the edges of the barriers, wherein there are no lipid multilayer structures on the substrate previously occupied by the barriers.

2. The method of claim 1, wherein each lipid solution of the plurality of lipid solutions further comprises one or more drugs, and wherein each lipid multilayer structure of the lipid multilayer structures is a microstructure comprising the one or more lipids and the one or more drugs of one lipid solution of the plurality of lipid solutions.

3. The method of claim 2, the method further comprising depositing cell cultures in the surface regions between the lipid multilayer structures after conducting step (c) and prior to removing the stencil from the substrate such that cells adhere to the surface regions between the lipid multilayer structures.

4. The method of claim 2, wherein two or more of the plurality of lipid solutions comprise different concentrations of a drug.

5. The method of claim 2, wherein a first array of one or more arrays of lipid multilayer structures comprises lipid multilayer structures comprising a first drug and wherein a second array of the one or more arrays comprises lipid microstructures comprising a second drug different from the first drug.

6. The method of claim 1, wherein the barriers comprise polydimethylsiloxane (PDMS).

7. The method of claim 1, wherein the lipid multilayer structures comprise 1,2-dioleoyl-3-trimethylammoniumpropane (chloride salt) (DOTAP).

8. The method of claim 1, wherein the solvent in each of the plurality of lipid solutions comprises ethanol.

* * * * *